US012735491B2

(12) United States Patent
Curnock et al.

(10) Patent No.: US 12,735,491 B2
(45) Date of Patent: Sep. 15, 2026

(54) MULTI-DOMAIN CD1a ANTAGONIST/PD-1 AGONIST ANTIBODY MOLECULES

(71) Applicant: Immunocore Limited, Abingdon (GB)

(72) Inventors: Adam Curnock, Abingdon (GB); David Overton, Abingdon (GB)

(73) Assignee: Immunocore Limited, Abingdon (GB)

( * ) Notice: Subject to any disclaimer, the term of this patent is extended or adjusted under 35 U.S.C. 154(b) by 0 days.

(21) Appl. No.: 19/011,114

(22) Filed: Jan. 6, 2025

(65) Prior Publication Data

US 2025/0333513 A1 Oct. 30, 2025

Related U.S. Application Data

(60) Provisional application No. 63/716,619, filed on Nov. 5, 2024, provisional application No. 63/618,230, filed on Jan. 5, 2024.

(51) Int. Cl.

| | |
|---|---|
| ***C07K 16/28*** | (2006.01) |
| ***A61P 37/04*** | (2006.01) |
| ***C07K 16/46*** | (2006.01) |
| ***G01N 33/68*** | (2006.01) |

(52) U.S. Cl.

CPC .......... *C07K 16/2833* (2013.01); *A61P 37/04* (2018.01); *C07K 16/2818* (2013.01); *C07K 16/468* (2013.01); *G01N 33/6854* (2013.01); *C07K 2317/24* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01); *G01N 2333/70521* (2013.01); *G01N 2333/70596* (2013.01)

(58) Field of Classification Search

CPC ............ C07K 16/2833; C07K 16/2818; C07K 16/468; C07K 2317/24; C07K 2317/31; C07K 2317/565; C07K 2317/567; C07K 2317/569; C07K 2317/76; C07K 2317/92; C07K 2317/94; C07K 2317/53; C07K 2317/622; C07K 2317/64; C07K 2317/73; C07K 2317/75; A61P 37/04; A61P 37/00; G01N 33/6854; G01N 2333/70521; G01N 2333/70596

See application file for complete search history.

(56) References Cited

U.S. PATENT DOCUMENTS

| | | | |
|---|---|---|---|
| 2021/0206856 A1 | 7/2021 | Higginson-Scott et al. | |
| 2021/0363216 A1 | 11/2021 | Bossi et al. | |
| 2022/0112291 A1* | 4/2022 | Winau | A61P 37/00 |

FOREIGN PATENT DOCUMENTS

| | | | |
|---|---|---|---|
| WO | 2010/029434 A1 | 3/2010 | |
| WO | 2011/110621 A1 | 9/2011 | |
| WO | WO-2017158176 A1 * | 9/2017 | C07K 16/38 |
| WO | 2018/024237 A1 | 2/2018 | |
| WO | 2020/157211 A1 | 8/2020 | |
| WO | 2024/223842 A1 | 10/2024 | |

OTHER PUBLICATIONS

Almagro et al., Front. Immunol. 2018; 8:1751 (Year: 2018).*
Chiu ML et al., Antibodies 2019 8, 55, 1-80 (Year: 2019).*
Noël et al. "Global analysis of VHHs framework regions with a structural alphabet." Biochimie 131 (2016): 11-19 (Year: 2016).*
Kim, Ji Hyung, et al. "CD1a on Langerhans cells controls inflammatory skin disease." Nature immunology 17.10 (2016): 1159-1166 (Year: 2016).*
Hardman, Clare S., et al. "CD1a promotes systemic manifestations of skin inflammation." Nature Communications 13.1 (2022):7535 (Year: 2022).*
Agata et al., "Expression of the PD-1 antigen on the surface of stimulated mouse T and B lymphocytes," Int Immunol 8:765-772 (1996).
Curnock et al., "Cell-targeted PD-1 agonists that mimic PD-L1 are potent T cell inhibitors," JCI Insight 6(20): e152468 (2021).
Dong et al., "B7-H1, a third member of the B7 family, co-stimulates T-cell proliferation and interleukin-10 secretion," Nat Med 5:1365-1369 (1999).
Freeman et al., "Engagement of the PD-1 immunoinhibitory receptor by a novel B7 family member leads to negative regulation of lymphocyte activation," J Exp Med 192:1027-1034 (2000).
International Search Report and Written Opinion issued in PCT/IB2025/050090, dated Apr. 11, 2025.
Keir et al., "PD-1 and its ligands in tolerance and immunity," Annu Rev Immunol 26:677-704 (2008).
Latchman et al., "PD-L2 is a second ligand for PD-1 and inhibits T cell activation," Nat Immunol 2:261-268 (2001).
Okazaki et al., "PD-1 and PD-1 ligands: from discovery to clinical application," Int Immunol 19:813-824 (2007).
Otsuka et al., "Differentiation of Langerhans Cells from Monocytes and Their Specific Function in Inducing IL-22-Specific Th Cells," J. Immunol 201(10): 3006-3016 (2018).
Paluch et al., "Immune Checkpoints as Therapeutic Targets in Autoimmunity," Front Immunol 9:2306 (2018).
Ravetch et al., "Fc receptors," Annu. Rev. Immunol. 9:457-492 (1991).
Schmitt et al., "Cyclosporin in the treatment of patients with atopic eczema—a systematic review and meta-analysis," J Eur Acad Dermatol Venereol 21(5):606-619 (2007).
Sulea, "Humanization of Camelid Single-Domain Antibodies," Methods in Molecular Biology 2446:299-312 (2022).

(Continued)

*Primary Examiner* — Gregory S Emch
*Assistant Examiner* — Kathleen Cunningchen
(74) *Attorney, Agent, or Firm* — MEDLER FERRO WOODHOUSE & MILLS PLLC

(57) ABSTRACT

The present disclosure provides multi-domain molecules comprising, (i) a first binding domain that binds to PD-1, (ii) a second binding domain that binds to CD1a, and optionally, (iii) a half-life extending domain. Such multi-domain molecules are particularly useful in the development of soluble immunotherapeutic reagents for the treatment of autoimmune diseases, such as atopic dermatitis (AD).

46 Claims, 38 Drawing Sheets

Specification includes a Sequence Listing.

(56) References Cited

OTHER PUBLICATIONS

Uniprot: Q9NZQ7 • PD1L1_HUMAN, retrieved on Apr. 23, 2025 at: https://www.uniprot.org/uniprotkb/Q9NZQ7/.

Ye et al., "CD1a and skin T cells: a pathway for therapeutic intervention," Clinical and Experimental Dermatology 49(5):450-458 (2024).

* cited by examiner mol427

| Antibody | Most human variant | Human % (FW) | # FW mismatches | WT (llama) Tm (°C) | Humanised Tm (°C) | WT (llama) KD 37°C (pM) | Humanised KD 37°C (pM) |
|---|---|---|---|---|---|---|---|
| AB002 | V10 | 89% | 9 | 60 | 61.3 | 288 | 448 |
| AB007 | V11 | 89% | 9 | 60.1 | 61.1 | 1700 | 2600 |
| AB052 | V9 | 90% | 8 | 60.5 | 60.8 | 840 | 3500 |

MULTI-DOMAIN CD1a ANTAGONIST/PD-1 AGONIST ANTIBODY MOLECULES

The content of the electronically submitted sequence listing in XML format (name: 0282-0004US1.xml; size: 182,453 bytes; and date of creation: Dec. 30, 2024) filed with the application is herein incorporated by reference in its entirety.

FIELD OF THE INVENTION

The present disclosure provides multi-domain molecules comprising, (i) a first binding domain that binds to an inhibitory immune checkpoint receptor, such as PD-1; and (ii) a second binding domain that binds to CD1a. Such multi-domain molecules can be useful in the development of soluble immunotherapeutics for the treatment of autoimmune diseases, such as atopic dermatitis (AD).

BACKGROUND

Autoimmune diseases are often chronic and debilitating, and constitute an area of clinical need. The current treatment landscape is dominated by systemically acting therapies, even where inflammation occurs in a single tissue. These systemic treatments can often lead to undesirable side effects and discontinuation of treatment.

In autoimmunity, there is mounting evidence that PD-1 pathway impairment plays an important role in disease pathogenesis. PD-1, PD-L1 and PD-L2 gene polymorphisms are associated with several autoimmune diseases. In addition, the PD-1 receptor is a key inhibitory immune checkpoint that regulates T cell activation and is involved in T cell exhaustion, a state of cellular paralysis. Autoreactive T cells are often main drivers of autoimmunity and T cell exhaustion correlates with good prognosis in autoimmune disease settings. Activating PD-1 on autoreactive lymphocytes thus may serve as a mechanism to treat autoimmune diseases. However, few PD-1 agonists have reached the clinic. In addition, treatment with PD-1 agonists alone harbors the risk of systemic effects.

The present disclosure provides for the first time immunotherapeutic candidates for the treatment of autoimmune disease that utilize two modes of action. The first mode of action is PD-1 mediated-inhibition. The second mode of action is localized blockade of autoreactive T cells by targeting of CD1a. CD1a is structurally related to an MHC I complex, and like an MHC I complex, presents antigen to T cells. However, the antigens are typically from lipids, either self or foreign, and not proteins. Furthermore, CD1a is non-restricted, that is, its expression is not limited to any particular subset (e.g., HLA subtype) of individuals. TCRs on CD1a-homing T cells can interact with CD1a by recognizing CD1a independently of antigen, or by recognizing a lipid-CD1a complex.

Autoimmune diseases with limited treatment options include moderate to severe atopic dermatitis (AD). For treatment of AD in particular, PD-1 mediated inhibition is compelling because of the relevance of the PD-1 pathway in AD. (Rosskopf, S., Jahn-Schmid, B., Schmetterer, K. G. et al. PD-1 has a unique capacity to inhibit allergen-specific human CD4+ T cell responses. Sci Rep 8, 13543 (2018)). Furthermore, activation of CD4 T helper cells by antigen presenting cells (APCs) in skin and draining lymph nodes is a key step in the pathogenesis of atopic dermatitis (AD). In addition, CD1a is constitutively and highly expressed on Langerhans cells and antigen presenting cell (APC) subsets in the skin, as well as being expressed by dendritic cells (DCs) in mucosal tissues. A large number of CD1a-homing T cells are contained within the skin and blood indicating that CD1a-specific T cells may play a role in skin diseases.

The present disclosure demonstrates that a bispecific molecule targeting CD1a is a compelling therapeutic candidate for AD and other autoimmune diseases, particularly when employed together with PD-1 mediated inhibition. Therapies to deliver localized inhibition of skin T cells are a novel strategy to treat AD.

SUMMARY OF THE INVENTION

In some aspects, the present disclosure relates to a multi-domain molecule comprising: (i) a first binding domain that binds to PD-1, and (ii) a second binding domain that binds to CD1a, wherein the second binding domain comprises a CDR1, a CDR2 and a CDR3 comprising the following sequences:

CDR1—GRTFNPGDLMG (SEQ ID NO: 4), GRAFRPHNVMA (SEQ ID NO: 5), or GRTFSPSDLMG (SEQ ID NO: 6), with zero, one, two or three mutations therein, CDR2—AIKWGPTYYADSVKG (SEQ ID NO: 7), AARWSGIYYAESVKG (SEQ ID NO: 8), or AIKWGPTYYSDSVKG (SEQ ID NO: 9), with zero, one, two or three mutations therein, CDR3—GSGTFSSNYRDFEY (SEQ ID NO: 10), STAQDMTLALMSDYDY (SEQ ID NO: 11), or GSSTFSANYRDYEY (SEQ ID NO: 12), with zero, one, two or three mutations therein.

In some aspects, the first binding domain comprises a CDR1, a CDR2 and a CDR3 comprising the following sequences:

CDR1—GFTFSSYA (SEQ ID NO: 1), with zero, one, two or three mutations therein,

CDR2—IASDGAST (SEQ ID NO: 2), with zero, one, two or three mutations therein,

CDR3—CARGGYLTYDRY (SEQ ID NO: 3), with zero, one, two or three mutations therein.

In some embodiments, the multi-domain molecule further comprises (iii) a half-life extending domain, where the half-life extending domain comprises a first IgG Fc chain (FC1) and a second IgG Fc chain (FC2), wherein the FC1 chain and FC2 chain dimerise to form an Fc domain, and wherein the C-terminus of the first binding domain is linked to the N-terminus of the second binding domain. In some embodiments, the C-terminus of the second binding domain is linked to the N-terminus of FC1.

In some aspects, the first binding domain is an antibody or fragment thereof, e.g. a VHH or scFv. In some aspects, the first binding domain is a VHH. In some aspects, the first binding domain to PD-1 comprises a KD in the range of about 1 nM to about 500 nM or in the range of about 50 nM to about 70 nM. In some aspects, the first binding domain binds to an epitope in PD-1 comprising one or more or all of the following amino acids: E38, F59, P60, E61, T75, Q76, L77, P78, N79 and G80, numbered according to SEQ ID NO: 13.

In some aspects, the first binding domain comprises FR1-CDR1-FR2-CDR2-FR3-CDR3-FR4, wherein FR is a framework region, and wherein FR1, FR2, FR3 and FR4 comprise the following sequences:

FR1—AVQLVESGGGLVQPGGSLRLSCAAS (SEQ ID NO: 14), with zero, one, two or three mutations therein, FR2—MTWVRQAPGKGPEWVSA (SEQ ID NO: 15), with zero, one, two or three mutations therein, FR3—SYADSVKGRFTISRDNSKNT-LYLQMNSLRPEDTAVYY (SEQ ID NO: 16), with zero, one, two or three mutations therein, FR4—YLTYDRYGQGTLVTVSS (SEQ ID NO: 17), with zero, one, two or three mutations therein.

In some aspects, the first binding domain comprises the amino acid sequence provided in SEQ ID NO: 18 or a humanized version thereof, or an amino acid sequence having at least 90%, at least 95% or at least 98% identity to SEQ ID NO: 18. In some aspects, the first binding domain comprises the amino acid sequence of SEQ ID NO: 20, or an amino acid sequence having at least 90%, at least 95% or at least 98% identity to SEQ ID NO: 20.

In some aspects, the first binding domain comprises a non-polymorphic, HLA-related molecule such as a CD1 epitope. In some aspects, the second binding domain binds to CD1a. In some aspects, the second binding domain is a VHH or scFv. In some aspects, the second binding domain is a VHH. In some aspects, the second binding domain is an anti-CD1a VHH. In some aspects, the second binding domain is a humanized anti-CD1a VHH. In some aspects, the second binding domain is a humanized llama anti-CD1a VHH. In some aspects, the humanized llama anti-CD1a VHH comprises one or more or all of the following amino acids: P24, F38, E45, R46, F48, A50, Y73, R75, V78, and G97, numbered according to SEQ ID NO: 21. In some aspects, the humanized llama anti-CD1a VHH comprises one or more or all of the following amino acids: P24, F38, F48, Y73, R75, and V78, numbered according to SEQ ID NO: 25. In some aspects, the humanized llama anti-CD1a VHH comprises one or more or all of the following amino acids: F38, E45, R46, F48, A50, Y73, K75, V78, P87 and V97, numbered according to SEQ ID NO: 28. In some aspects, the humanized llama anti-CD1a VHH comprises one or more or all of the following amino acids: F38, E45, R46, F48, A50, Y73, K75, V78, and G97, numbered according to SEQ ID NO: 29. In some aspects, the humanized llama anti-CD1a VHH comprises a reduced hook effect as compared to wild-type llama anti-CD1a VHH. In some aspects, the second binding domain is humanized to human IGHV3-23*01 and human IGHJ*04.

In some aspects, the second binding domain comprises a CDR1, a CDR2 and a CDR3 comprising the following sequences:

CDR1—GRTFNPGDLMG (SEQ ID NO: 4), with zero, one, two or three mutations therein, CDR2—AIKWGPTYYADSVKG (SEQ ID NO: 7), with zero, one, two or three mutations therein, CDR3—GSGTFSSNYRDFEY (SEQ ID NO: 10), with zero, one, two or three mutations therein.

In some aspects, the second binding domain comprises a CDR1, a CDR2 and a CDR3 comprising the following sequences:

CDR1—GRAFRPHNVMA (SEQ ID NO: 5), with zero, one, two or three mutations therein, CDR2—AARWSGIYYAESVKG (SEQ ID NO: 8), with zero, one, two or three mutations therein, CDR3—STAQDMTLALMSDYDY (SEQ ID NO: 11), with zero, one, two or three mutations therein.

In some aspects, the second binding domain comprises a CDR1, a CDR2 and a CDR3 comprising the following sequences:

CDR1—GRTFSPSDLMG (SEQ ID NO: 6), with zero, one, two or three mutations therein, CDR2—AIKWGPTYYSDSVKG (SEQ ID NO: 9), with zero, one, two or three mutations therein, CDR3—GSSTFSANYRDYEY (SEQ ID NO: 12), with zero, one, two or three mutations therein.

In some aspects, the second binding domain comprises FR1-CDR1-FR2-CDR2-FR3-CDR3-FR4, wherein FR is a framework region, and wherein FR1, FR2, FR3 and FR4 comprise the following sequences:

FR1—EVQLLESGGGLVQPGGSLRLSCAAS (SEQ ID NO: 30), with zero, one, two or three mutations therein, FR2—WVRQAPGKGLEWVS (SEQ ID NO: 31), with zero, one, two or three mutations therein, FR3—RFTISRDNSKNTLYLQMNSLRAEDTAVYY-CAAK (SEQ ID NO: 32), with zero, one, two or three mutations therein, FR4—WGQGTLVTVSS (SEQ ID NO: 33), with zero, one, two or three mutations therein.

In some aspects, the mutation(s) in the second binding domain framework regions are selected from A24P, V38F, G45E, L46R, W48F, S50A, N73Y, K75R, L78V and A97G numbered according to SEQ ID NO: 21. In some aspects, the mutation(s) in the second binding domain framework regions are selected from A24P, V38F, W48F, N73Y, K75R, and L78V numbered according to SEQ ID NO: 25. In some aspects, the mutation(s) in the second binding domain framework regions are selected from V38F, G45E, L46R, W48F, S50A, N73Y, K75R, L78V, A87P and A97V numbered according to SEQ ID NO: 28. In some aspects, the mutation(s) in the second binding domain framework regions are selected from V38F, G45E, L46R, W48F, S50A, N73Y, K75R, L78V and A97G numbered according to SEQ ID NO: 29.

In some aspects, the second binding domain comprises the amino acid sequence provided in SEQ ID NO: 34 or a humanized version thereof, or an amino acid sequence having at least 90%, at least 95% or at least 98% identity to SEQ ID NO: 21. In some aspects, the second binding domain comprises the amino acid sequence, or a humanized version thereof, provided in SEQ ID NO: 25, or an amino acid sequence having at least 90%, at least 95% or at least 98% identity to SEQ ID NO: 25. In some aspects, the second binding domain comprises the amino acid sequence provided in SEQ ID NO: 35 or a humanized version thereof, or an amino acid sequence having at least 90%, at least 95% or at least 98% identity to SEQ ID NO: 28. In some aspects, the second binding domain comprises the amino acid sequence provided in SEQ ID NO: 36 or a humanized version thereof, or an amino acid sequence having at least 90%, at least 95% or at least 98% identity to SEQ ID NO: 29. In some aspects, the second binding domain comprises the amino acid sequence provided in SEQ ID NO: 21, SEQ ID NO: 22, SEQ ID NO: 23, SEQ ID NO: 24, SEQ ID NO: 25, SEQ ID NO: 26, or SEQ ID NO: 27.

In some aspects, the multi-domain molecule described herein comprises a half-life extending domain. In some aspect, the half-life extending domain comprises:

(a) one or more amino acid substitutions which facilitate dimerisation of FC1 and FC2; and/or (b) one or more amino acid substitutions which prevent or reduce binding to FcγR; and/or (c) one or more amino acid substitutions which promote binding to FcRn.

In some aspects:

(i) one of the FC1 and the FC2 comprises one or more amino acid substitutions selected from the group consisting of T366S, L368A, T394S, F405A, Y407A, Y407T and Y407V according to SEQ ID NO: 37; and (ii) the other of the FC1 and the FC2 comprises one or more amino acid substitutions selected from the group consisting of T366W, T366Y, T366W, T394W and F405W according to SEQ ID NO: 37.

In some aspects:

(i) one of the FC1 and the FC2 comprises one or more amino acid substitutions selected from the group consisting of T366S, L368A, and Y407V according to SEQ ID NO: 37; and (ii) the other of the FC1 and the FC2 comprises a T366W amino acid substitution according to SEQ ID NO: 37.

In some aspects, the half-life extending domain comprises one or more amino acid substitutions which attenuate an effector function of the Fc domain. In some aspects, the half-life extending domain comprises one or more amino acid substitutions selected from the group consisting of S228P, E233P, L234A, L235A, L235E, L235P, G236R, G237A, P238S, F241A, V264A, D265A, H268A, D270A, N297A, N297G, N297Q, E318A, K322A, L328R, P329G, P329A, A330S, A330L, P331A and P331S according to SEQ ID NO: 37. In some aspects, the FC1 and/or the FC2 comprise a N297G amino acid substitution according to SEQ ID NO: 37.

In some aspects:

(a) either FC1 or FC2 comprises the amino acid sequence provided in SEQ ID NO: 38 or 39, or an amino acid sequence that has at least 90%, at least 95%, or at least 98% identity to the amino acid sequence provided in SEQ ID NO: 38 or 39, and (b) the other of FC1 and FC2 comprises the amino acid sequence provided in SEQ ID NO: 40 or 41, or an amino acid sequence that has at least 90%, at least 95%, or at least 98% identity to the amino acid sequence provided in SEQ ID NO: 40 or 41.

In some aspects, the first binding domain is linked to the N-terminus of the second binding domain by a linker and/or IgG hinge sequence. In some aspects, the linker comprises the following sequence: GGGGS (SEQ ID NO: 44), with zero, one, two or three mutations therein. In some aspects, the C-terminus of the second binding domain is linked to the N-terminus of FC1 via an IgG hinge sequence. In some aspects, the Fc domain comprises an IgG hinge sequence at the N-terminus of FC2. In some aspects, the IgG hinge comprises the amino acid sequence of SEQ ID NO: 43 or SEQ ID NO: 42.

In some aspects, the multidomain molecule of the present disclosure comprises the amino acid sequence of: (i) SEQ ID NO: 57; and (ii) SEQ ID NO: 58. In some aspects, the multidomain molecule of the present disclosure comprises the amino acid sequence of: (i) SEQ ID NO: 59; and (ii) SEQ ID NO: 58. In some aspects, the multidomain molecule of the present disclosure comprises the amino acid sequence of: (i) SEQ ID NO: 63; and (ii) SEQ ID NO: 58.

In some aspects, the present disclosure relates to a single domain antibody that binds to CD1a comprising a CDR1, CDR2 and CDR3, comprising the following amino acid sequences:

CDR1—GRTFNPGDLMG (SEQ ID NO: 4), GRAFRPHNVMA (SEQ ID NO: 5), or GRTFSPSDLMG (SEQ ID NO: 6), with zero, one, two or three mutations therein, CDR2—AIKWGPTYYADSVKG (SEQ ID NO: 7), AARWSGIYYAESVKG (SEQ ID NO: 8), or AIKWGPTYYSDSVKG (SEQ ID NO: 9), with zero, one, two or three mutations therein, CDR3—GSGTFSSNYRDFEY (SEQ ID NO: 10), STAQDMTLALMSDYDY (SEQ ID NO: 11), or GSSTFSANYRDYEY (SEQ ID NO: 12), with zero, one, two or three mutations therein.

In some aspects, (a) the single domain antibody is isolated; and/or (b) the single domain antibody is a VHH; and/or (c) the single domain antibody is an anti-CD1a antibody; and/or (d) the single domain antibody binds to CD1a with a KD in the range of about 100 pM to about 5000 pM or in the range of about 600 pM to about 3000 pM; and/or (e) the single domain antibody comprises the amino acid sequence provided in SEQ ID NO: 34 or a humanized version thereof, or an amino acid sequence having at least 90%, at least 95% or at least 98% identity to SEQ ID NO: 21; and/or (f) the single domain antibody comprises the amino acid sequence provided in SEQ ID NO: 35 or a humanized version thereof, or an amino acid sequence having at least 90%, at least 95% or at least 98% identity to SEQ ID NO: 28; and/or (g) the single domain antibody comprises the amino acid sequence provided in SEQ ID NO: 36 or a humanized version thereof, or an amino acid sequence having at least 90%, at least 95% or at least 98% identity to SEQ ID NO: 29. In some aspects, the single domain antibody is linked to a binding domain that binds an immune checkpoint receptor. In some aspects, the immune checkpoint receptor is PD-1.

In some aspects, the present disclosure provides a nucleic acid encoding the multi-domain molecule described herein, wherein (a) the first and second binding domains are encoded within a single open reading frame, or within two distinct open reading frames; (b) the first binding domain, second binding domain and half-life extending domain are encoded within a single open reading frame, or within distinct open reading frames; and/or (c) the single domain antibody.

In some aspects, the present disclosure provides an expression vector comprising the nucleic acid disclosed herein. In some aspects, the present disclosure provides a cell harbouring: (a) the expression vector described herein; (b) a first expression vector comprising a nucleic acid encoding a first binding domain and a second expression vector comprising a nucleic acid encoding a second binding domain as described herein; or (c) a first expression vector comprising a nucleic acid encoding the first binding domain of the multi-domain molecule, a second expression vector comprising a nucleic acid encoding the second binding domain of the multi-domain molecule, and a third expression vector comprising a nucleic acid encoding the half-life extending domain of the multi-domain molecule as described herein.

In some aspects, the present disclosure provides a non-naturally occurring and/or purified and/or engineered cell, preferably a T-cell, presenting the multi-domain molecule described herein. In some aspects, the present disclosure provides a pharmaceutical composition comprising the multi-domain molecule, the single domain antibody, the nucleic acid, the expression vector, and/or the cell, together with one or more pharmaceutically acceptable carriers or excipients.

In some aspects, the present disclosure provides the single domain antibody, the nucleic acid, the expression vector, and/or the cell, for use in medicine, preferably in a human subject. In some aspects, the present disclosure provides a multi-domain molecule for use in a method of treating atopic dermatitis, psoriasis and/or skin lichenoid diseases.

In some aspects, the present disclosure provides a method of producing the multi-domain molecule or the single domain antibody, the method comprising a) maintaining the cell under optimal conditions for expression of the multi-domain molecule or single domain antibody and b) isolating the multi-domain molecule or single domain antibody.

In some aspects, the present disclosure provides a multi-domain molecule comprising: (i) a PD-1 agonist VHH, (ii) a humanized CD1a-binding VHH, and (iii) a half-life extending domain, wherein:

(a) the PD-1 agonist VHH comprises a CDR1, a CDR2 and a CDR3 comprising the following sequences:
 CDR1—GFTFSSYA (SEQ ID NO: 1), with zero or one mutation therein,
 CDR2—IASDGAST (SEQ ID NO: 2), with zero or one mutation therein,
 CDR3—CARGGYLTYDRY (SEQ ID NO: 3), with zero or one mutations therein;
(b) the humanized CD1a-binding VHH comprises a CDR1, a CDR2 and a CDR3 comprising the following sequences:
 CDR1—GRTFNPGDLMG (SEQ ID NO: 4), with zero or one mutation therein,
 CDR2—AIKWGPTYYADSVKG (SEQ ID NO: 7), with zero or one mutation therein,
 CDR3—GSGTFSSNYRDFEY (SEQ ID NO: 10), with zero or one mutation therein; and
(c) the half-life extending domain comprises a first IgG Fc chain (FC1) and a second IgG Fc chain (FC2), wherein the FC1 chain and FC2 chain dimerise to form an Fc domain; wherein the C-terminus of the PD-1 agonist VHH is linked to the N-terminus of the humanized CD1a-binding VHH by a linker comprising the following sequence: GGGGS (SEQ ID NO: 44), with zero, one, two or three mutations therein; and wherein the C-terminus of the humanized CD1a-binding VHH is linked to the N-terminus of FC1 via an IgG hinge sequence, and/or wherein the Fc domain comprises an IgG hinge sequence at the N-terminus of FC2.

In some aspects, the present disclosure provides a multi-domain molecule comprising: (i) a PD-1 agonist VHH, (ii) a humanized CD1a-binding VHH, and (iii) a half-life extending domain, wherein:

(a) the PD-1 agonist VHH comprises a CDR1, a CDR2 and a CDR3 comprising the following sequences:
 CDR1—GFTFSSYA (SEQ ID NO: 1), with zero, one, two or three mutations therein,
 CDR2—IASDGAST (SEQ ID NO: 2), with zero, one, two or three mutations therein,
 CDR3—CARGGYLTYDRY (SEQ ID NO: 3), with zero, one, two or three mutations therein;
(b) the humanized CD1a-binding VHH comprises a CDR1, a CDR2 and a CDR3 comprising the following sequences:
 CDR1—GRAFRPHNVMA (SEQ ID NO: 5), with zero, one, two or three mutations therein,
 CDR2—AARWSGIYYAESVKG (SEQ ID NO: 8), with zero, one, two or three mutations therein,
 CDR3—STAQDMTLALMSDYDY (SEQ ID NO: 11), with zero, one, two or three mutations therein; and
(c) the half-life extending domain comprises a first IgG Fc chain (FC1) and a second IgG Fc chain (FC2), wherein the FC1 chain and FC2 chain dimerise to form an Fc domain; wherein the C-terminus of the PD-1 agonist VHH is linked to the N-terminus of the humanized CD1a-binding VHH by a linker comprising the following sequence: GGGGS (SEQ ID NO: 44), with zero, one, two or three mutations therein; and wherein the C-terminus of the humanized CD1a-binding VHH is linked to the N-terminus of FC1 via an IgG hinge sequence, and/or wherein the Fc domain comprises an IgG hinge sequence at the N-terminus of FC2.

In some aspects, the present disclosure provides a multi-domain molecule comprising: (i) a PD-1 agonist VHH, (ii) a humanized CD1a-binding VHH, and (iii) a half-life extending domain, wherein:

(a) the PD-1 agonist VHH comprises a CDR1, a CDR2 and a CDR3 comprising the following sequences:
 CDR1—GFTFSSYA (SEQ ID NO: 1), with zero, one, two or three mutations therein,
 CDR2—IASDGAST (SEQ ID NO: 2), with zero, one, two or three mutations therein,
 CDR3—CARGGYLTYDRY (SEQ ID NO: 3), with zero, one, two or three mutations therein;
(b) the humanized CD1a-binding VHH comprises a CDR1, a CDR2 and a CDR3 comprising the following sequences:
 CDR1—GRTFSPSDLMG (SEQ ID NO: 6), with zero, one, two or three mutations therein,
 CDR2—AIKWGPTYYSDSVKG (SEQ ID NO: 9), with zero, one, two or three mutations therein,
 CDR3—GSSTFSANYRDYEY (SEQ ID NO: 12) with zero, one, two or three mutations therein; and
(c) the half-life extending domain comprises a first IgG Fc chain (FC1) and a second IgG Fc chain (FC2), wherein the FC1 chain and FC2 chain dimerise to form an Fc domain; wherein the C-terminus of the PD-1 agonist VHH is linked to the N-terminus of the humanized CD1a-binding VHH by a linker comprising the following sequence: GGGGS (SEQ ID NO: 44), with zero, one, two or three mutations therein; and wherein the C-terminus of the humanized CD1a-binding VHH is linked to the N-terminus of FC1 via an IgG hinge sequence, and/or wherein the Fc domain comprises an IgG hinge sequence at the N-terminus of FC2.

In some aspects, the IgG hinge comprises the amino acid sequence of SEQ ID NO: 43 or SEQ ID NO: 42.

In some aspects, the disclosure provides a method for treating an autoimmune disease in a subject, the method comprising administering the multi-domain molecule as described herein, the single domain antibody as described herein, the nucleic acid as described herein, the expression vector as described herein, and/or the cell as described herein. In some aspects, the autoimmune disease is atopic dermatitis, psoriasis and/or skin lichenoid diseases.

In some aspects, the disclosure provides a bispecific molecule that binds to PD-1 and CD1a, wherein the bispecific molecule comprises a means for binding PD-1 and a means for binding CD1a. In some aspects, the means for binding PD-1 comprises a first binding domain that corresponds to a PD-1 agonist, a PD-1 agonist ligand, or a fragment or modification thereof. In some aspects, the means for binding PD-1 comprises a first binding domain comprising a CDR1, a CDR2 and a CDR3 comprising the following sequences:

CDR1—GFTFSSYA (SEQ ID NO: 1), with zero, one, two or three mutations therein,
 CDR2—IASDGAST (SEQ ID NO: 2), with zero, one, two or three mutations therein, and
 CDR3—CARGGYLTYDRY (SEQ ID NO: 3), with zero, one, two or three mutations therein.

In some aspects, the means for binding CD1a comprises a second binding domain that corresponds to a soluble TCR, an antigen-binding fragment, or a fragment or modification thereof. In some aspects, the means for binding CD1a comprises a first binding domain comprising a CDR1, a CDR2 and a CDR3 comprising the following sequences: (i) CDR1—GRTFNPGDLMG (SEQ ID NO: 4), GRAFRPHNVMA (SEQ ID NO: 5), or GRTFSPSDLMG (SEQ ID NO: 6), with zero, one, two or three mutations therein, (ii) CDR2—AIKWGPTYYADSVKG (SEQ ID NO: 7), AARWSGIYYAESVKG (SEQ ID NO: 8), or AIKWGPTYYSDSVKG (SEQ ID NO: 9), with zero, one, two or three mutations therein, and (iii) CDR3—GSGTFSSNYRDFEY (SEQ ID NO: 10), STAQDMTLALMSDYDY (SEQ ID NO: 11), or GSSTFSANYRDYEY (SEQ ID NO: 12), with zero, one, two or three mutations therein.

In some aspects, the disclosure provides a method for treating an autoimmune disease in a subject, the method comprising: administering to the subject a means for binding PD-1 and CD1a. In some aspects, the means for binding PD-1 comprises a first binding domain that corresponds to a PD-1 agonist, a PD-1 agonist ligand, or a fragment or modification thereof. In some aspects, the means for binding CD1a comprises a second binding domain that corresponds to a soluble TCR, an antigen-binding fragment, or a fragment or modification thereof. In some aspects, the means for binding PD-1 comprises a first binding domain comprising a CDR1, a CDR2 and a CDR3 comprising the following sequences: (i) CDR1—GFTFSSYA (SEQ ID NO: 1), with zero, one, two or three mutations therein, (ii) CDR2—IASDGAST (SEQ ID NO: 2), with zero, one, two or three mutations therein, and (iii) CDR3—CARGGYLTYDRY (SEQ ID NO: 3), with zero, one, two or three mutations therein. In some aspects, the means for binding CD1a comprises a second binding domain comprising a CDR1, a CDR2 and a CDR3 comprising the following sequences: (i) CDR1—GRTFNPGDLMG (SEQ ID NO: 4), GRAFRPHNVMA (SEQ ID NO: 5), or GRTFSPSDLMG (SEQ ID NO: 6), with zero, one, two or three mutations therein, (ii) CDR2—AIKWGPTYYADSVKG (SEQ ID NO: 7), AARWSGIYYAESVKG (SEQ ID NO: 8), or AIKWGPTYYSDSVKG (SEQ ID NO: 9), with zero, one, two or three mutations therein, and (iii) CDR3—GSGTFSSNYRDFEY (SEQ ID NO: 10), STAQDMTLALMSDYDY (SEQ ID NO: 11), or GSSTFSANYRDYEY (SEQ ID NO: 12), with zero, one, two or three mutations therein.

In some aspects, the present disclosure further provides a method comprising measuring levels of soluble PD-1 (sPD1) from a sample in the subject. In some aspects, increased levels of soluble PD-1 (sPD1) indicate PD-1 binding. In some aspects, increased levels of soluble PD-1 (sPD1) indicate CD1a binding. In some aspects, increased levels of soluble PD-1 (sPD1) indicate simultaneous CD1a and PD-1 binding.

In some aspects, the present disclosure provides a method of measuring engagement, or efficacy of engagement, of the multi-domain molecule, the single domain antibody, or the bispecific molecule of the present disclosure with a target PD-1 marker and/or a CD1-a marker in a subject, wherein the method comprises: (i) administering to the subject the multi-domain molecule, single domain antibody, or bispecific molecule; and (ii) measuring a level of soluble PD-1 (sPD-1) in a biological sample obtained from the subject, wherein a relative increase in the measured level of sPD-1 compared to a control sample indicates engagement of the multi-domain molecule, single domain antibody, or bispecific molecule with the target PD-1 marker and/or CD1a marker.

In some aspects, the present disclosure provides a method of treating an autoimmune disease in a subject, the method comprising: (i) determining a baseline level of soluble PD-1 (sPD-1) in a biological sample obtained from the subject (T0), (ii) administering to the subject a first dosage amount of a multi-domain molecule binding to PD-1 and CD1a, and (iii) determining a level of sPD-1 (T1) after (ii) in a biological sample obtained from the subject (T1), wherein if T1 is greater than or equal to T0, then a second dosage amount of the multi-domain molecule is administered, wherein the second dosage amount is the same or less than the first dosage amount, or wherein if T1 is less than T0, then the second dosage amount of the multi-domain molecule is greater than the first dosage amount and/or further comprises a second autoimmune disease treatment.

The present disclosure further provides a method of enhancing T cell exhaustion comprising administering the multi-domain molecule of the present disclosure by simultaneously targeting PD-1 and CD1a.

BRIEF DESCRIPTION OF THE DRAWINGS

The following drawings form part of the present specification and are included to further demonstrate exemplary embodiments of certain aspects of the present disclosure.

FIG. 6. Crystal structures of the wild-type VHH antibody molecules Ab002, Ab007 and Ab096 bound to CD1a.

DETAILED DESCRIPTION

Figure 1A:
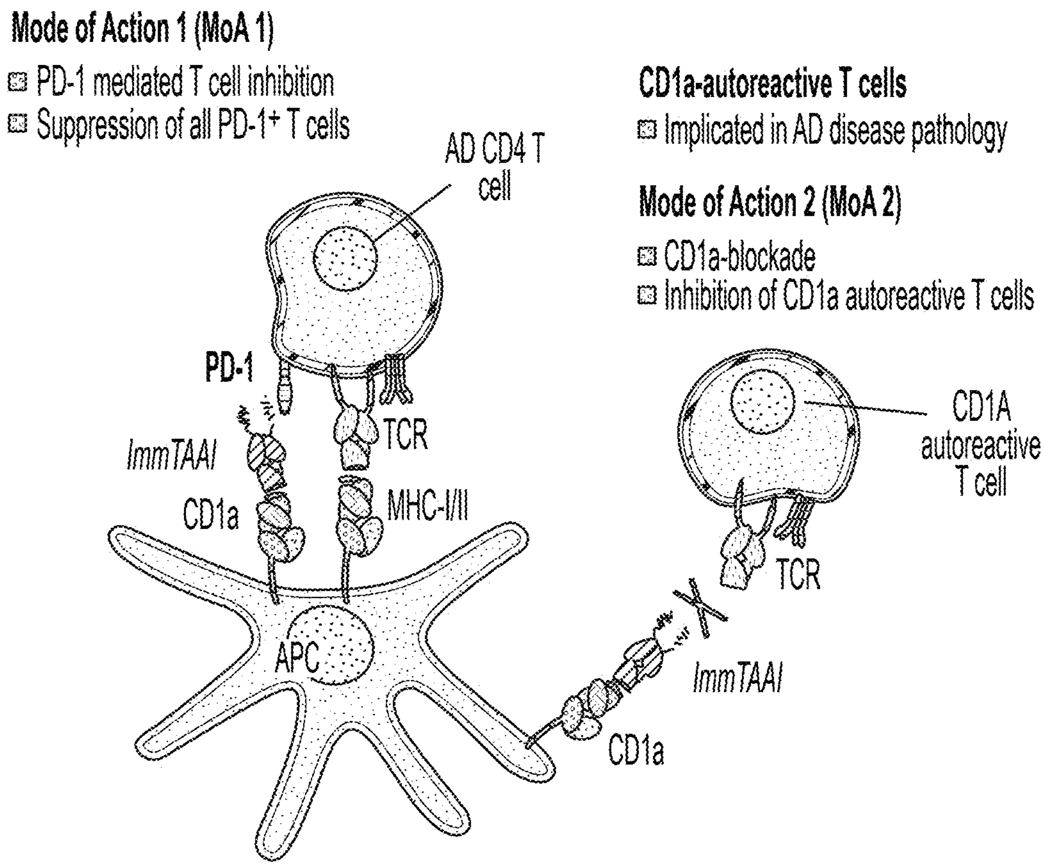
FIG. 1A is a schematic showing the dual action mechanism of a CD1a-PD-1 bispecific molecule.

It should be understood that any embodiment described herein, including those described only in the examples, can be combined with any one or more other embodiments, unless such combination is expressly disclaimed or is improper. Thus, the term "embodiment", as used herein, is not to be considered as excluding features recited in other embodiments.

Unless otherwise defined herein, scientific and technical terms used in the present disclosure shall have meanings that are commonly understood by one of ordinary skill in the art. Further, unless otherwise required by context, singular terms shall include pluralities and plural terms shall include the singular.

The articles "a" and "an" are used herein to refer to one or to more than one (i.e., to at least one) of the grammatical object of the article. By way of example, "an element" means one element or more than one element.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." means that the specific terms recited are representative examples and embodiments of the disclosure that are not intended to be limited to the specific examples referenced or cited unless explicitly stated otherwise.

As used herein, "about" can mean plus or minus 10% of the provided value. Where ranges are provided, they are inclusive of the boundary values. "About" can additionally or alternately mean either within 10% of the stated value, or within 5% of the stated value, or in some cases within 2.5% of the stated value; or "about" can mean rounded to the nearest significant digit.

As used herein, "between" is a range inclusive of the ends of the range. For example, a number between x and y explicitly includes the numbers x and y and any numbers that fall within x and y.

As used herein, the term "antibody" includes, but is not limited to, genetically engineered or otherwise modified forms of immunoglobulins, such as intrabodies, chimeric antibodies, fully human antibodies, humanized antibodies (e.g. generated by "CDR-grafting"), antibody fragments, and heteroconjugate antibodies (e.g., bispecific antibodies, diabodies, triabodies, tetra-bodies, etc.). The term "antibody" includes cys-diabodies and minibodies. Thus, each and every embodiment provided herein in regard to "antibodies", or "antibody like constructs" is also envisioned as, bi-specific antibodies, diabodies, scFv fragments, chimeric antibody receptor (CAR) constructs, diabody and/or minibody embodiments, unless explicitly denoted otherwise. The term "antibody" includes a polypeptide of the immunoglobulin family or a polypeptide comprising fragments of an immunoglobulin that is capable of non-covalently, reversibly, and in a specific manner binding a corresponding antigen, as disclosed herein. An exemplary antibody structural unit comprises a tetramer. In some embodiments, a full-length antibody can be composed of two identical pairs of polypeptide chains, each pair having one "light" and one "heavy" chain (connected through a disulfide bond). The term "antibody" also comprises immunoglobulins (Ig's) of different classes (i.e., IgA, IgG, IgM, IgD and IgE) and subclasses (such as IgG1, IgG2 etc.). An "antibody" is an example of an "antigen-binding molecule," where the molecule is capable of specifically recognizing and binding to an antigen.

Antibody formats include functional antibody fragments, single chain antibodies, single domain antibodies, and chimeric, humanized, bispecific or multispecific antibodies. An "antigen binding fragment" of an antibody refers to a portion of a full-length antibody, or a protein that resembles a portion of a full-length antibody, that retains the ability to bind to its target antigen, in particular the antigen binding region or variable region of the full-length antibody. Examples of "antigen binding fragments" include Fv, Fab, F(ab')2, Fab', dsFv, (dsFv)2, scFv, sc(Fv)2 and diabodies. For example, a multi-domain binding molecule of the disclosure may comprise a scFv. A "antigen binding fragment" may also be a single domain antibody, such as a heavy chain antibody. As is known in the art, the antigen binding site of a single domain antibody, such as a VHH, may comprise three CDRs (as opposed to six in a conventional antibody). The term "antigen binding moiety" or "antigen binding fragment" of an antibody, as used herein, encompasses such binding sites. Alternatively, or additionally, the binding molecule may comprise a Fab or Fv fragment. The term "Fab" denotes an antibody fragment having a molecular weight of about 50,000 Dalton and antigen binding activity, in which about a half of the N-terminal side of H chain and the entire L chain, among fragments obtained by treating IgG with a protease, e.g. papain, are bound together through a disulfide bond. The Fv fragment is the N-terminal part of the Fab fragment of an antibody and consists of the variable portions of one light chain and one heavy chain.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

In embodiments, the antibody nomenclature used in the present disclosure for the targeting arm is referred to as AbXXX or AbXXX WT, wherein the initials "WT" indicate the wild-type version of AbXXX. In embodiments, the antibody nomenclature used as AbXXX. # indicates a humanized antibody version of AbXXX, at a numbered variant (#). For example, Ab002.10 indicates a humanized Ab002 antibody of variant numbered 10. In embodiments, Ab002 or Ab002 WT indicates the wild-type Ab002 antibody without humanization.

The term "phenotypically silent variants" is understood to refer to a variant which incorporates one or more further amino acid changes, including substitutions, insertions and deletions, in addition to those set out above, which variant has a similar phenotype to the corresponding molecule without said change(s). For the purposes of this application, phenotype comprises binding affinity ($K_D$ and/or binding half-life) and specificity. Preferably, the phenotype for a soluble multi-domain binding molecule includes potency of immune activation and purification yield, in addition to binding affinity and specificity.

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulfur containing side chains). It should be appreciated that amino acid substitutions within the scope of the present disclosure can be made using naturally occurring or non-naturally occurring amino acids. For example, it is contemplated herein that the methyl group on an alanine can be replaced with an ethyl group, and/or that minor changes can be made to the peptide backbone. Whether or not natural or synthetic amino acids are used, it is preferred that only L-amino acids are present.

Substitutions of this nature are often referred to as "conservative" or "semi-conservative" amino acid substitutions. The present disclosure therefore extends to use of a molecule comprising any of the amino acid sequence described above but with one or more conservative substitutions and or one or more tolerated substitutions in the sequence, such that the amino acid sequence of the TCR has at least 90% identity, such as 90%, 91%, 92%, 93%, 94%, 95%, 96%, 97%, 98%, 99% or 100% identity, to the TCR sequences disclosed herein.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case can be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)). In embodiments, the protein numbering scheme is based on the Kabat numbering scheme proposed by Wu and Kabat in 1970 and relied only on the amino acid sequence. In embodiments, the protein numbering scheme is based on the Eu numbering scheme. In embodiments, the protein numbering scheme is based on the Chothia proposed by Chothia (1987), who introduced structure-based factors into the numbering scheme. In embodiments, protein numbering scheme is based on the IMGT and Aho numbering schemes, which allow for greater flexibility when dealing with insertions and deletions (Honneger and Plückthun 2001; Lefranc et al. 1999). The IMGT unique numbering provides positions of the amino acids (and corresponding codons) in coding sequences, in 2D graphical representations or IMGT Colliers de Perles and in 3D structures. A person of ordinary skill in the art would understand and know how to use the tools available in the art to convert from one protein numbering scheme to another. One such available resource is the IMGT Scientific conversion chart available at: www.imgt.org/IMGTScientificChart/Numbering/Hu_IGHGnber.html.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present disclosure.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the disclosure. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See www.ncbi.nlm.nih.gov. Another example of a mathematical algorithm utilized for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Mutations, including conservation and tolerated substitutions, insertions, and deletions, can be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning-A Laboratory Manual (3rd Ed.) CSHL Press. Further information on ligation independent cloning (LIC) procedures can be found in Rashtchian, (1995) 24urrO pin Biotechnol 6 (1): 30-6. The TCR sequences provided by the disclosure can be obtained from solid state synthesis, or any other appropriate method known in the art.

Activation of CD4 T helper cells by antigen presenting cells (APCs) in skin and draining lymph nodes is a key step in the pathogenesis of atopic dermatitis (AD). Therapies to deliver localized inhibition of skin T cells are a novel strategy to treat AD. The present disclosure has achieved this local inhibition by targeting CD1a, an HLA-unrestricted target that presents lipids to CD1a-autoreactive T cells, a subpopulation of T cells implicated in inflammatory skin diseases. CD1a, a non-polymorphic, HLA-related molecule, is highly expressed on Langerhans cells and skin dendritic cells. Because CD1a is non-polymorphic, the present disclosure provides the potential to treat patients without being restricted by HLA subtype.

The present disclosure provides novel molecules, referred to generally as ImmTAAIs® (Immune Modulating Monoclonal TCRs Against Autoimmune Disease, Immunocore Ltd.). ImmTAAI generally refers to a bispecific molecule comprising an organ-specific or antigen-specific soluble TCR capable of specifically binding to a peptide MHC (pMHC) or MHC-like complex, where the soluble TCR is fused to an immune suppressive effector function. In some instances, the molecule binding to the pMHC or MHC-like complex in an ImmTAAI can be a TCR mimic (TCRm), or an antigen-binding molecule, such as antibody, or fragment thereof. The present disclosure provides novel bi-specific molecules that exhibit high levels of PD-1-mediated T cell suppression and blockade of CD1a-autoreactive T cell activation by tethering in a localized fashion to specific CD1a-specific target cells. These CD1a-targeted PD-1 agonist ImmTAAIs deliver localized inhibition of inflammatory T cells in AD skin while avoiding systemic immunosuppression.

Multi-Domain Molecule

The disclosure as described herein provides a multi-domain molecule comprising: (i) a first binding domain that binds to an inhibitory immune checkpoint receptor, such as PD-1, (ii) a second binding domain that binds to a CD1a, wherein the C-terminus of the first binding domain is linked to the N-terminus of the second binding domain. In some aspects, the muti-domain protein further comprises (iii) a half-life extending domain. In some aspects, the half-life extending domain comprises a first IgG Fc chain (FC1) and a second IgG Fc chain (FC2), wherein the FC1 chain and FC2 chain dimerise to form an Fc domain, and wherein the C-terminus of the second binding domain is linked to the N-terminus of FC1.

I. First Binding Domain—Inhibitory Immune Receptor

As described herein, the first binding domain binds to PD-1, i.e., the first binding domain comprises an immune suppressor. In some embodiments, the inhibitory immune checkpoint receptor comprises an antigen binding fragment that binds to an antigen located on an immune cell. In the context of the present disclosure, "immune cell" can refer to, for example, a T cell or a B cell. In particular, the antigen of the antigen-binding fragment can be a T cell surface antigen.

In some embodiments, the target (i.e., antigen) of the first binding domain is an immune modulator. In some embodiments, the target can be an immune checkpoint molecule, such as PD-1 (Programmed Death 1 receptor), A2AR (Adenosine A2A receptor), A2BR (Adenosine A2B receptor), B7-H3 (B7 Homolog 3, also called CD276) B7-H4 (B7 Homolog 4, also called VTCN1), BTLA (B and T Lymphocyte Attenuator, also called CD272), CTLA-4 (Cytotoxic T-Lymphocyte-Associated protein 4, also called CD152), IDO (Indoleamine 2,3-dioxygenase), CD200 Receptor, KIR (Killer-cell Immunoglobulin-like Receptor), TIGIT (T cell Immunoreceptor with Ig and ITIM domains), LAG3 (Lymphocyte Activation Gene-3), NOX2 (nicotinamide adenine dinucleotide phosphate NADPH oxidase isoform 2), TIM-3 (T-cell Immunoglobulin domain and Mucin domain 3), VISTA (V-domain Ig suppressor of T cell activation), SIGLEC7 (Sialic acid-binding immunoglobulin-type lectin 7, also called CD328), and SIGLEC9 (Sialic acid-binding immunoglobulin-type lectin 9, also called CD329). In some embodiments, the target is PD-1. In some embodiments, the first binding domain can be an agonist of one or more of the above immune checkpoint molecules. Thus, in some embodiments, the immune suppressor can be an immune checkpoint agonist (i.e., to inhibit immune activation). Some suitable immune checkpoint agonists, including native ligands and antibodies, are reviewed in Paluch et al Front Immunol, 2018, 9:2306, for example.

In some embodiments, instead of comprising an antigen binding fragment of an antibody, the first binding domain comprises one of a receptor-ligand pair, whereby the first binding domain is capable of binding to the other of the receptor-ligand pair. In some embodiments, the target ligand or receptor can be located on an immune cell. In some embodiments, the first binding domain comprises a ligand of an immune checkpoint molecule described above. In some embodiments, the first binding domain comprises the extracellular region of PD-L1 (Uniprot ref: Q9NZQ7) or PD-L2

(Q9BQ51) or a functional fragment thereof (i.e., a portion that is capable of binding to PD-1). In some embodiments, the first binding domain comprises the amino acid sequence provided in SEQ ID NO: 19, or an amino acid sequence having at least 90% or at least 95% identity to SEQ ID NO: 19. Such an immune suppressor in some embodiments can engage an immune cell by binding to PD-1 and stimulate PD-1 signaling.

In some embodiments, the first binding domain comprises an agonist antibody or agonist antibody binding fragment that binds to, and preferably stimulates signaling of, an immune checkpoint molecule. In some embodiments, the first binding domain can be, or comprise, a PD-1 agonist antibody (e.g., single domain antibody). In some embodiments, such PD-1 agonists do not compete with PD-L1 for binding to PD-1. In some embodiments, such PD-1 agonists have a high degree of specificity for PD-1 and give rise to a potent inhibitory response when tested in reporter assays. In some embodiments, the PD-1 agonist can be a full-length antibody or fragment thereof, such as a scFv or a Fab fragment, or a single domain antibody, such as a VHH. Examples of such antibodies are provided in WO2011110621 and WO2010029434 and WO2018024237. Thus, in some embodiments the antigen of the first binding domain can be PD-1 and the antigen binding fragment of the first binding domain can be a PD-1 agonist. In some embodiments, the antigen binding fragment of the first binding domain can comprise a single domain antibody, optionally a VHH. In some embodiments, the first binding domain is a PD-1 agonist VHH.

As described above, the first binding domain is preferably a PD-1 agonist. As used herein, the term "PD-1 agonist" refers to any molecule that is capable of binding to PD-1 and activating PD-1 signaling, including e.g., the PD-1 ligand, PD-L1, and PD-1 agonist antibodies. Activation of the PD-1 pathway down-regulates immune activity, promoting peripheral immune tolerance and preventing autoimmunity (Keir et al., Annu Rev Immunol, 26:677-704, 2008; Okazaki et al., Int Immunol 19:813-824, 2007). PD-1 is a transmembrane receptor protein expressed on the surface of activated immune cells, including T cells, B cells, NK cells and monocytes (Agata et al., Int Immunol 8:765-772, 1996). The cytoplasmic tail of PD-1 comprises an immunoreceptor tyrosine-based inhibitory motif (ITIM). PD-L1 and PD-L2 are the natural ligands of PD-1 and are expressed on the surface of antigen presenting cells (Dong et al., Nat Med., 5:1365-1369, 1999; Freeman et al., J Exp Med 192:1027-1034, 2000; Latchman et al., Nat Immunol 2:261-268, 2001). Upon ligand engagement, phosphatases are recruited to the ITIM region of PD-1 leading to inhibition of TCR-mediated signaling, and subsequent reduction in lymphocyte proliferation, cytokine secretion and cytotoxic activity. In some embodiments, PD-1 can also induce apoptosis in T cells via its ability to inhibit survival signals from co-stimulation (Keir et al., Annu Rev Immunol, 26:677-704, 2008). Targeted activation of the PD-1 pathway therefore provides an approach for the treatment of autoimmune conditions, such as T1DM.

In some embodiments, the antigen binding fragment of the immune suppressor can have the general structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively. In some embodiments, the disclosure provides a multidomain molecule comprising a first binding domain that binds to PD-1, (ii) a second binding domain that binds to CD1a, wherein the first binding domain comprises a CDR1, a CDR2 and a CDR3 comprising the following sequences:

CDR1—GFTFSSYA (SEQ ID NO: 1), with zero, one, two or three mutations therein,

CDR2—IASDGAST (SEQ ID NO: 2), with zero, one, two or three mutations therein,

CDR3—CARGGYLTYDRY (SEQ ID NO: 3), with zero, one, two or three mutations therein.

In some embodiments, the first binding domain is a single domain antibody that binds to PD-1 and comprises CDRs, CDR1, CDR2 and CDR3, having the following amino acid sequences:

CDR1—GFTFSSYA (SEQ ID NO: 1), with zero, one, two or three mutations therein,

CDR2—IASDGAST (SEQ ID NO: 2), with zero, one, two or three mutations therein, and CDR3—CARGGYLTYDRY (SEQ ID NO: 3), with zero, one, two or three mutations therein.

In some embodiments, the antigen-binding moiety is a VHH.

In some embodiments, the first binding domain can be a VHH comprising the amino acid sequence of SEQ ID NO: 18, or a humanized version thereof, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 18. Alternatively, the first binding domain can be a VHH comprising the amino acid sequence of SEQ ID NO: 20, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 20.

In some embodiments, the single domain antibody is a VHH comprising the amino acid sequence provided in SEQ ID NO: 20.

In some embodiments, the first binding domain is covalently linked to the second binding domain via the C- or N-terminus of the second binding domain, optionally via a linker sequence. In some embodiments, the C-terminus of the first binding domain is covalently linked to the Nterminus of the second binding domain, optionally via a linker sequence. Suitable linker sequences are known in the art. Linker sequences are usually flexible, in that they are made up primarily of amino acids such as glycine, alanine and serine, which do not have bulky side chains likely to restrict flexibility. In some embodiments, linkers with greater rigidity can be desirable. Usable or optimum lengths of linker sequences can be determined by the skilled artisan. In some embodiments, the linker sequence is less than about 12, such as less than 10, or from 2-10 amino acids in length. In some embodiments, the first binding domain can be covalently linked to the second binding domain via the C- or N-terminus of the alpha chain or beta chain via a linker sequence selected from GGGGS (SEQ ID NO: 44), GGGSG (SEQ ID NO: 45), GGSGG (SEQ ID NO: 46), GSGGG (SEQ ID NO: 47), GSGGGP (SEQ ID NO: 48), GGEPS (SEQ ID NO: 49), GGEGGGP (SEQ ID NO: 50), GGEGGGSEGGGS (SEQ ID NO: 51), GGGSGGGG (SEQ ID NO: 52), GGGGSGGGGSGGGGSGGGGSGGGS (SEQ ID NO: 53), GGGGSGGGGSGGGGSGGGGS (SEQ ID NO: 54), EAAAK (SEQ ID NO: 55) and EAAAKEAAAKEAAAK (SEQ ID NO: 56).

In some embodiments, the first binding domain can be covalently linked to the C- or N-terminus of the second binding domain via a linker sequence of GGGGS (SEQ ID NO: 44). In some embodiments, the C-terminus of the first binding domain can be covalently linked to the N terminus of the beta chain via a linker sequence of GGGGS (SEQ ID NO: 44).

In some embodiments, the first binding domain, i.e. the immune suppressor, sequence can optionally have zero, one, two, three, or four amino acid substitutions relative to the sequences recited above.

In some embodiments, the immune suppressor can comprise CDRs that are at least 90%, at least 95%, at least 98%, or at least 99% identical to the sequence of SEQ ID NO: 1, 2, and 3 as CDR1, CDR2 and CDR3, respectively.

In some embodiments, the first binding domain comprises CDRs with sequence as described in any of combinations 1-19 described below:

| | First binding domain | | |
|---|---|---|---|
| Combination | CDR1 (SEQ ID NO: 1) | CDR2 (SEQ ID NO: 2) | CDR3 (SEQ ID NO: 3) |
| 1 | 0 mutations | 0 mutations | 0 mutations |
| 2 | 0 mutations | 0 mutations | 1 mutations |
| 3 | 0 mutations | 0 mutations | 2 mutations |
| 4 | 0 mutations | 0 mutations | 3 mutations |
| 5 | 0 mutations | 1 mutations | 0 mutations |
| 6 | 0 mutations | 2 mutations | 0 mutations |
| 7 | 0 mutations | 3 mutations | 0 mutations |
| 8 | 1 mutations | 0 mutations | 0 mutations |
| 9 | 2 mutations | 0 mutations | 0 mutations |
| 10 | 3 mutations | 0 mutations | 0 mutations |
| 11 | 1 mutations | 1 mutations | 0 mutations |
| 12 | 2 mutations | 2 mutations | 0 mutations |
| 13 | 3 mutations | 3 mutations | 0 mutations |
| 14 | 1 mutations | 0 mutations | 1 mutations |
| 15 | 2 mutations | 0 mutations | 2 mutations |
| 16 | 3 mutations | 0 mutations | 3 mutations |
| 17 | 0 mutations | 1 mutations | 1 mutations |
| 18 | 0 mutations | 2 mutations | 2 mutations |
| 19 | 0 mutations | 3 mutations | 3 mutations |

The skilled person would appreciate that the format of the multi-domain molecule of the disclosure could equally be applied to PD-1 agonist sequences other than those recited above.

In some embodiments, the first binding domain to PD-1 comprises an affinity, i.e., $K_D$, in the range of about 1 nM to about 500 nM or in the range of about 50 nM to about 70 nM. In some embodiments, the first binding domain comprises a $K_D$ in the range of about 10 nM to about 500 nM, about 20 nM to about 400 nM, about 30 nM to about 300 nM, about 40 nM to about 200 nM, or about 50 nM to about 100 nM. In some embodiments, the first binding domain comprises a $K_D$ in the range of about 50 nM to about 70 nM. In some embodiments, a first binding domain can have a binding half-life of from about 1 seconds to about 40 seconds, or preferably from about 15 seconds to about 20 seconds. The affinity of the first binding domain can be measured using methods described herein, e.g., in the examples, and by methods known to the skilled artisan.

In some embodiments, the first binding domain binds to an epitope in PD-1 comprising one or more or all of the following amino acids: E38, F59, P60, E61, T75, Q76, L77, P78, N79 and G80, numbered according to SEQ ID NO: 13. In some embodiments, the first binding domain binds to an epitope in PD-1 comprising two, three, four, five, six, seven, eight, nine or all 10 of the following amino acids: E38, F59, P60, E61, T75, Q76, L77, P78, N79 and G80, numbered according to SEQ ID NO: 13.

In some embodiments, the first binding domain comprises FR1-CDR1-FR2-CDR2—FR3-CDR3-FR4, wherein FR is a framework region, and wherein FR1, FR2, FR3 and FR4 comprise the following sequences:

FR1—AVQLVESGGGLVQPGGSLRLSCAAS (SEQ ID NO: 14), with zero, one, two or three mutations therein, FR2—MTWVRQAPGKGPEWVSA (SEQ ID NO: 15), with zero, one, two or three mutations therein, FR3—SYADSVKGRFTISRDNSKNT-LYLQMNSLRPEDTAVYY (SEQ ID NO: 16), with zero, one, two or three mutations therein, FR4—YLTYDRYGQGTLVTVSS (SEQ ID NO: 17), with zero, one, two or three mutations therein.

In some embodiments, the first binding domain comprises the amino acid sequence provided in SEQ ID NO: 18 or a humanized version thereof, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 18. In some embodiments, the first binding domain comprises the amino acid sequence provided in SEQ ID NO: 18 but with one, two, three, four, five, six, seven, eight, nine, ten, eleven or twelve mutations.

In some embodiments, the first binding domain comprises the amino acid sequence of SEQ ID NO: 20, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 20. In some embodiments, the first binding domain comprises the amino acid sequence provided in SEQ ID NO: 20 but with one, two, three, four, five, six, seven, eight, nine, ten, eleven or twelve mutations.

As is well-known in the art, protein molecules such as the muti-domain molecules described herein, can be subject to post-translational modifications. Glycosylation is one such modification, which comprises the covalent attachment of oligosaccharide moieties to defined amino acids in an antibody chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e., oligosaccharide type, covalent linkage and total number of attachments) can influence protein function. Therefore, when producing recombinant proteins, controlling glycosylation is often desirable. Controlled glycosylation has been used to improve antibody-based therapeutics. (Jefferis et al., (2009) Nat Rev Drug Discov March; 8 (3): 226-34.). Glycosylation can be controlled, by using particular cell lines for example (including but not limited to mammalian cell lines such as Chinese hamster ovary (CHO) cells or human embryonic kidney (HEK) cells), or by chemical modification. Such modifications can be desirable, since glycosylation can improve pharmacokinetics, reduce immunogenicity and more closely mimic a native human protein (Sinclair and Elliott, (2005) Pharm Sci. August; 94 (8): 1626-35). Alternatively, glycosylation can lead to a lack of consistency in manufacturing which is not desirable for a therapeutic molecule.

ii. Second Binding Domain

In some embodiments, the second binding domain of the multi-domain molecule described herein binds to a non-polymorphic, HLA-related molecule. In some embodiments, the non-polymorphic, HLA-related molecule comprises a CD1 epitope. In some embodiments, the CD1 epitope comprises a CD1a, CD1b, CD1c, CD1d or a CD1e epitope. Preferably, the second binding domain binds to CD1a.

In some embodiments, the second binding domain is a VHH or scFv. In some embodiments, the second binding domain is a VHH. In some embodiments, the second binding domain is an anti-CD1a VHH. In some embodiments, the second binding domain is a humanized anti-CD1a VHH. In some embodiments, the second binding domain is a humanized llama anti-CD1a VHH.

The terms "anti-CD1a antibody" and "anti-CD1a antibody fragment," as used herein, mean antibodies or antibody fragments which recognize or bind to CD1a. The anti-CD1a HHV for use in the present disclosure can include one or more conservative substitutions which have a similar amino acid sequence and/or which retain the same function (i.e. are phenotypically silent). The skilled person is aware that various amino acids have similar properties and thus substitutions between them are "conservative". One or more such amino acids of a protein, polypeptide or peptide can often be substituted by one or more other such amino acids without eliminating a desired activity of that protein, polypeptide, or peptide. As used herein, the term "antibody" encompasses such fragments and variants. Examples of anti-CD1a antibodies include but are not limited to RM393, NA1/34, O10 and EP80. Antibody fragments and variants/analogues which are suitable for use in the compositions and methods described herein include minibodies, Fab fragments, F(ab') z fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (*Pieris* (Germany)), comprising engineered anticalins) to name but a few.

In some embodiments, the second binding domain comprises a VHH antibody against CD1a, a non-polymorphic, HLA-related molecule that is highly expressed on Langerhans cells and skin dendritic cells. CD1a is an unrestricted target and accessible to all patients. In some embodiments, CD1a presents lipids to CD1a-autoreactive T cells, a subpopulation of T cells implicated in inflammatory skin diseases. In some embodiments, blockade of CD1a-autoreactive T cells could provide a mode of action for CD1a-targeted binding domain. In some embodiments, CD1a antibodies show negligible cross-reactivity with CD1b-d expressing or antigen negative target cells. Ins some embodiments, the VHH CD1a antibody binds to CD1a epitopes distal to the F' portal. In some embodiments, binding is not influenced by CD-1 bound lipids. In some embodiments, the VHH CD1a antibody binds to the side face of CD1a antigen.

In some embodiments the seconding bind domain comprises a humanized llama anti-CD1a VHH comprising one or more or all of the following amino acids: P24, F38, E45, R46, F48, A50, Y73, K75, V78, and G97, numbered according to SEQ ID NO: 21.

In some embodiments, the humanized llama anti-CD1a VHH comprises one or more or all of the following amino acids: F38, E45, R46, F48, A50, Y73, K75, V78, P87 and V97, numbered according to SEQ ID NO: 28.

In some embodiments, the humanized llama anti-CD1a VHH comprises one or more or all of the following amino acids: F38, E45, R46, F48, A50, Y73, K75, V78, and G97, numbered according to SEQ ID NO: 29.

In some embodiments, the humanized llama anti-CD1a VHH comprises a reduced hook effect. The hook effect refers to the prozone phenomenon, also known as antibody excess or the Postzone phenomenon, also known as antigen excess. It is an immunologic phenomenon whereby the effectiveness of antibodies to form immune complexes can be impaired when concentrations of an antibody or an antigen are very high. The formation of immune complexes stops increasing with greater concentrations and then decreases at extremely high concentrations, producing a hook shape on a graph of measurements. An important practical relevance of the phenomenon is as a type of interference that plagues certain immunoassays and nephelometric assays, resulting in false negatives or inaccurately low results. Other common forms of interference include antibody interference, cross-reactivity and signal interference. The phenomenon is caused by very high concentrations of a particular analyte or antibody and is most prevalent in one-step (sandwich) immunoassays.

In some embodiments, the second binding domain is humanized to human IGHV3-23*01 and/or human IGHJ*04. In some embodiments, the second binding domain is humanized to any human antibody chain variable region known in the art.

In some embodiments, the second binding domain comprises a CDR1, a CDR2 and a CDR3 comprising the following sequences:

CDR1—GRTFNPGDLMG (SEQ ID NO: 4), with zero, one, two or three mutations therein, CDR2—AIKWGPTYYADSVKG (SEQ ID NO: 7), with zero, one, two or three mutations therein, CDR3—GSGTFSSNYRDFEY (SEQ ID NO: 10), with zero, one, two or three mutations therein.

In some embodiments, the second binding domain comprises a CDR1, a CDR2 and a CDR3 comprising the following sequences:

CDR1—GRAFRPHNVMA (SEQ ID NO: 5), with zero, one, two or three mutations therein, CDR2—AARWSGIYYAESVKG (SEQ ID NO: 8), with zero, one, two or three mutations therein, CDR3—STAQDMTLALMSDYDY (SEQ ID NO: 11), with zero, one, two or three mutations therein.

In some embodiments, the second binding domain comprises a CDR1, a CDR2 and a CDR3 comprising the following sequences:

CDR1—GRTFSPSDLMG (SEQ ID NO: 6), with zero, one, two or three mutations therein, CDR2—AIKWGPTYYSDSVKG (SEQ ID NO: 9), with zero, one, two or three mutations therein, CDR3—GSSTFSANYRDYEY (SEQ ID NO: 12), with zero, one, two or three mutations therein.

In some embodiments, CDR2 and CDR3 are defined by Kabat method. In some embodiments, CDR1 is defined by a union of Kabat and Chothia. See, e.g., Sulea, T. (2022). Humanization of Camelid Single-Domain Antibodies. In: Hussack, G., Henry, K. A. (eds) Single-Domain Antibodies. Methods in Molecular Biology, 2446, 299-312.

In some embodiments, the second binding domain comprises the following sequence:

FR1-CDR1-FR2-CDR2-FR3-CDR3-FR4

In some embodiments, FR is a framework region, wherein FR1, FR2, FR3 and FR4 comprise the following sequences:

FR1—EVQLLESGGGLVQPGGSLRLSCAAS (SEQ ID NO: 30), with zero, one, two or three mutations therein, FR2—WVRQAPGKGLEWVS (SEQ ID NO: 31), with zero, one, two or three mutations therein, FR3—RFTISRDNSKNTLYLQMNSLRAEDTAVYYCAAK (SEQ ID NO: 32), with zero, one, two or three mutations therein, FR4—WGQGTLVTVSS (SEQ ID NO: 33), with zero, one, two or three mutations therein.

In some embodiments, the mutation(s) in the second binding domain framework regions are selected from A24P, V38F, G45E, L46R, W48F, S50A, N73Y, K75R, L78V and A97G numbered according to SEQ ID NO: 21.

In some embodiments, the mutation(s) in the second binding domain framework regions are selected from V38F, G45E, L46R, W48F, S50A, N73Y, K75R, L78V, A87P and A97V numbered according to SEQ ID NO: 28.

In some embodiments, the mutation(s) in the second binding domain framework regions are selected from V38F, G45E, L46R, W48F, S50A, N73Y, K75R, L78V and A97G numbered according to SEQ ID NO: 29.

In some embodiments, the second binding domain comprises the amino acid sequence provided in SEQ ID NO: 34 or a humanized version thereof, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 21.

In some embodiments, the second binding domain comprises the amino acid sequence provided in SEQ ID NO: 35 or a humanized version thereof, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 28.

In some embodiments, the second binding domain comprises the amino acid sequence provided in SEQ ID NO: 36 or a humanized version thereof, or an amino acid sequence having at least 80%, at least 85%, at least 90%, at least 91%, at least 92%, at least 93%, at least 94%, at least 95%, at least 95%, at least 96%, at least 97%, at least 98% or at least 99% identity to SEQ ID NO: 29.

In some embodiments, the second binding domain comprises the amino acid sequence provided in SEQ ID NO: 22, SEQ ID NO: 23, SEQ ID NO: 24, SEQ ID NO: 25, SEQ ID NO: 26, SEQ ID NO: 27.

In some embodiments, the second binding domain can comprise CDRs that are at least 90%, at least 95%, at least 98%, or at least 99% identical to the sequence of SEQ ID NOs: 4, 7, and 10 as CDR1, CDR2 and CDR3, respectively. In some embodiments, the second binding domain can comprise CDRs that are at least 90%, at least 95%, at least 98%, or at least 99% identical to SEQ ID NO: 5, 8, and 11 as CDR1, CDR2 and CDR3, respectively. In some embodiments, the second binding domain can comprise CDRs that are at least 90%, at least 95%, at least 98%, or at least 99% identical to SEQ ID NO: 6, 9, and 12 as CDR1, CDR2 and CDR3, respectively.

In some embodiments, the second binding domain comprises CDRs with sequence as described in any of combinations 1-19 described below:

-continued

| | second binding domain | | |
|---|---|---|---|
| Combination | CDR1 (SEQ ID NO: 4) | CDR2 (SEQ ID NO: 7) | CDR3 (SEQ ID NO: 10) |
| 1 | 0 mutations | 0 mutations | 0 mutations |
| 2 | 0 mutations | 0 mutations | 1 mutations |
| 3 | 0 mutations | 0 mutations | 2 mutations |
| 4 | 0 mutations | 0 mutations | 3 mutations |
| 5 | 0 mutations | 1 mutations | 0 mutations |
| 6 | 0 mutations | 2 mutations | 0 mutations |
| 7 | 0 mutations | 3 mutations | 0 mutations |
| 8 | 1 mutations | 0 mutations | 0 mutations |
| 9 | 2 mutations | 0 mutations | 0 mutations |
| 10 | 3 mutations | 0 mutations | 0 mutations |
| 11 | 1 mutations | 1 mutations | 0 mutations |
| 12 | 2 mutations | 2 mutations | 0 mutations |
| 13 | 3 mutations | 3 mutations | 0 mutations |
| 14 | 1 mutations | 0 mutations | 1 mutations |
| 15 | 2 mutations | 0 mutations | 2 mutations |
| 16 | 3 mutations | 0 mutations | 3 mutations |
| 17 | 0 mutations | 1 mutations | 1 mutations |
| 18 | 0 mutations | 2 mutations | 2 mutations |
| 19 | 0 mutations | 3 mutations | 3 mutations |

In some embodiments, the second binding domain comprises CDRs with sequence as described in any of combinations 20-38 described below:

| | second binding domain | | |
|---|---|---|---|
| Combination | CDR1 (SEQ ID NO: 5) | CDR2 (SEQ ID NO: 8) | CDR3 (SEQ ID NO: 11) |
| 20 | 0 mutations | 0 mutations | 0 mutations |
| 21 | 0 mutations | 0 mutations | 1 mutations |
| 22 | 0 mutations | 0 mutations | 2 mutations |
| 23 | 0 mutations | 0 mutations | 3 mutations |
| 24 | 0 mutations | 1 mutations | 0 mutations |
| 25 | 0 mutations | 2 mutations | 0 mutations |
| 26 | 0 mutations | 3 mutations | 0 mutations |
| 27 | 1 mutations | 0 mutations | 0 mutations |
| 28 | 2 mutations | 0 mutations | 0 mutations |
| 29 | 3 mutations | 0 mutations | 0 mutations |
| 30 | 1 mutations | 1 mutations | 0 mutations |
| 31 | 2 mutations | 2 mutations | 0 mutations |
| 32 | 3 mutations | 3 mutations | 0 mutations |
| 33 | 1 mutations | 0 mutations | 1 mutations |
| 34 | 2 mutations | 0 mutations | 2 mutations |
| 35 | 3 mutations | 0 mutations | 3 mutations |
| 36 | 0 mutations | 1 mutations | 1 mutations |
| 37 | 0 mutations | 2 mutations | 2 mutations |
| 38 | 0 mutations | 3 mutations | 3 mutations |

In some embodiments, the second binding domain comprises CDRs with sequence as described in any of combinations 39-57 described below:

| | second binding domain | | |
|---|---|---|---|
| Combination | CDR1 (SEQ ID NO: 6) | CDR2 (SEQ ID NO: 9) | CDR3 (SEQ ID NO: 12) |
| 39 | 0 mutations | 0 mutations | 0 mutations |
| 40 | 0 mutations | 0 mutations | 1 mutations |
| 41 | 0 mutations | 0 mutations | 2 mutations |
| 42 | 0 mutations | 0 mutations | 3 mutations |
| 43 | 0 mutations | 1 mutations | 0 mutations |
| 44 | 0 mutations | 2 mutations | 0 mutations |
| 45 | 0 mutations | 3 mutations | 0 mutations |
| 46 | 1 mutations | 0 mutations | 0 mutations |
| 47 | 2 mutations | 0 mutations | 0 mutations |
| 48 | 3 mutations | 0 mutations | 0 mutations |
| 49 | 1 mutations | 1 mutations | 0 mutations |
| 50 | 2 mutations | 2 mutations | 0 mutations |

-continued

| | second binding domain | | |
|---|---|---|---|
| Combination | CDR1 (SEQ ID NO: 6) | CDR2 (SEQ ID NO: 9) | CDR3 (SEQ ID NO: 12) |
| 51 | 3 mutations | 3 mutations | 0 mutations |
| 52 | 1 mutations | 0 mutations | 1 mutations |
| 53 | 2 mutations | 0 mutations | 2 mutations |
| 54 | 3 mutations | 0 mutations | 3 mutations |
| 55 | 0 mutations | 1 mutations | 1 mutations |
| 56 | 0 mutations | 2 mutations | 2 mutations |
| 57 | 0 mutations | 3 mutations | 3 mutations |

In some embodiments, the second binding domain that binds to CD-1a comprises $K_D$ in the range of about 100 pM to about 5000 pM or in the range of about 600 pM to about 3000 pM. In some embodiments, the second binding domain that binds to CD1a comprises a $K_D$ in the range of about 200 pM to about 1000 pM, about 500 pM to about 4000 pM, about 700 pM to about 2000 pM, about 3000 pM to about 5000 pM, or about 100 pM to about 500 pM. In some embodiments, the second binding domain that binds to CD1a comprises a $K_D$ in the range of about 700 pM to about 1000 pM, or 2000 to about 2500 pM.

Iii. Half-Life Extending Domains

In some embodiments, the multi-domain molecule described herein comprises a half-life extending domain. In some embodiments, the half-life extending domain comprises:

(a) one or more amino acid substitutions which facilitate dimerisation of FC1 and FC2; and/or (b) one or more amino acid substitutions which prevent or reduce binding to FcγR; and/or (c) one or more amino acid substitutions which promote binding to FcRn.

A "half-life extending domain", as used herein, refers to a protein domain for extending the half-life of the multi-domain binding protein, relative to a multi-domain binding protein lacking the half-life extending domain. The half-life extending domain comprises a first 1gG Fc region (FC1) and a second 1gG Fc region (FC2), wherein the FC1 region and FC2 region dimerise to form an Fc domain. As used herein, the term "Fc region" is used to refer to a region of a single polypeptide chain comprising at least a CH2 domain and a CH3 domain sequence, whereas the term "Fc domain" refers to a dimer of two Fc regions (i.e., FC1 and FC2).

WO 2020/157211 describes an approach for extending the half-life of a TCR-anti-CD3 fusion protein by fusing it to an 1gG Fc domain. The present inventors have surprisingly found that the multi-domain binding molecules of the disclosure retain the extended half-life provided by the Fc domain in the format disclosed in WO 2020/157211, but, in addition, have significantly higher potency.

In some embodiments, (i) one of the FC1 and the FC2 in the disclosure described herein comprises one or more amino acid substitutions selected from the group consisting of T366S, L368A, T394S, F405A, Y407A, Y407T and Y407V according to SEQ ID NO: 37; and (ii) the other of the FC1 and the FC2 comprises one or more amino acid substitutions selected from the group consisting of T366W, T366Y, T366W, T394W and F405W according to SEQ ID NO: 37.

In some embodiments (i) one of the FC1 and the FC2 in the disclosure described herein comprises one or more amino acid substitutions selected from the group consisting of T366S, L368A, and Y407V according to SEQ ID NO: 37; and (ii) the other of the FC1 and the FC2 comprises a T366W amino acid substitution according to SEQ ID NO: 37.

In some embodiments, the half-life extending domain comprises one or more amino acid substitutions which attenuate an effector function of the Fc domain. In some embodiments, the half-life extending domain comprises one or more amino acid substitutions selected from the group consisting of S228P, E233P, L234A, L235A, L235E, L235P, G236R, G237A, P238S, F241A, V264A, D265A, H268A, D270A, N297A, N297G, N297Q, E318A, K322A, L328R, P329G, P329A, A330S, A330L, P331A and P331S according to SEQ ID NO: 37.

In some embodiments, the FC1 and/or the FC2 comprise a N297G amino acid substitution according to SEQ ID NO: 37.

In some embodiments, (a) either FC1 or FC2 comprises the amino acid sequence provided in SEQ ID NO: 38 or 39, or an amino acid sequence that has at least 90%, at least 95%, or at least 98% identity to the amino acid sequence provided in SEQ ID NO: 38 or 39, and (b) the other of FC1 and FC2 comprises the amino acid sequence provided in SEQ ID NO: 40 or 41, or an amino acid sequence that has at least 90%, at least 95%, or at least 98% identity to the amino acid sequence provided in SEQ ID NO: 40 or 41.

In some embodiments, the first binding domain of the multi-domain molecule described herein is linked to the C-terminus of the second binding domain by a linker and/or IgG hinge sequence. In some embodiments, the linker comprises the following sequence: GGGGS (SEQ ID NO: 44), with zero, one, two or three mutations therein. In some embodiments, the C-terminus of the second binding domain is linked to the N-terminus of FC1 via an IgG hinge sequence. In some embodiments, the Fc domain comprises an IgG hinge sequence at the N-terminus of FC2. In some embodiments, the IgG hinge comprises the amino acid sequence of SEQ ID NO: 43 or SEQ ID NO: 42

In some embodiments, the immunoglobulin Fc domain can be any antibody Fc domain. The Fc domain is the tail region of an antibody that interacts with cell surface Fc receptors and some proteins of the complement system. The Fc domain comprises two polypeptide chains (i.e., two Fc "regions") both having two or three heavy chain constant domains (termed CH2, CH3 and CH4), and optionally a hinge region. In some embodiments, the two Fc region chains can be linked by one or more disulfide bonds within the hinge region. Fc domains from immunoglobulin sub-classes 1gG1, 1gG2 and 1gG4 can bind to and undergo FcRn mediated recycling, affording a long circulatory half-life (3-4 weeks), thus extending the half-life of the multidomain binding molecule of the disclosure. The interaction of 1gG with FcRn has been localized in the Fc region covering parts of the CH2 and CH3 domains. Preferred immunoglobulin Fc domains for use in the present disclosure include but are not limited to Fc domains from 1gG1 or 1gG4. For example, the Fc domain can be an 1gG1 Fc domain, i.e., the FC1 and FC2 regions can be 1gG1 Fc regions. The Fc domain can be derived from human sequences.

In some embodiments, the FC1 region can comprise, or consist of, an amino acid sequence that is at least 80% identical to the sequence of SEQ ID NO: 38 or 39 and the FC2 region can comprise, or consist of, an amino acid sequence that is at least 80% identical to the sequence of SEQ ID NO: 40 or 41. In some embodiments, the FC1 region can comprise, or consist of, an amino acid sequence that is at least 90%, at least 95%, or at least 98% identical to the sequence of SEQ ID NO: 38 or 39 and the FC2 region can comprise an amino acid sequence that is at least 90%, at least 95%, or at least 98% identical to the sequence of SEQ ID NO: 40 or 41. Preferably, the FC1 region comprises the amino acid sequence provided in SEQ ID NO: 38 or 39 and the FC2 region comprises the amino acid sequence provided in SEQ ID NO: 40 or 41. As the skilled person would appreciate, the sequences provided above for FC1 and FC2 are suitable vice versa. For example, the FC1 region can comprise the amino acid sequence provided in SEQ ID NO: 38 or 39 and the FC2 region can comprise the amino acid sequence provided in SEQ ID NO: 40 or 41.

In some embodiments, the disclosure provides a multi-domain molecule as described herein, comprising the following amino acid sequences, in the following order, from N-terminus to C-terminus: (a) a first binding domain that binds to PD-1, optionally followed by a linker sequence at least 80%, at least 90%, or at least 95% identical to SEQ ID NO 44; (b) a second binding domain that binds to CD1aa; (c) a linker sequence at least 80%, at least 90%, or at least 95% identical to SEQ ID NO: 44 followed by an IgG hinge sequence at least 80%, at least 90%, or at least 95% identical to SEQ ID NO: 43; (d) an Fc region having the sequence at least 80%, at least 90%, or at least 95% identical to SEQ ID NO: 38 or 39; (e) a linker sequence at least 80%, at least 90%, or at least 95% identical to SEQ ID NO: 44 followed by an 1gG hinge sequence at least 80%, at least 90%, or at least 95% identical to SEQ ID NO: 43; and (f) an Fc region having the sequence at least 80%, at least 90%, or at least 95% identical to SEQ ID NO: 38.

In some embodiments, the disclosure provides a multi-domain molecule as described herein, comprising the following amino acid sequences, in the following order, from N-terminus to C-terminus: (a) a first binding domain that binds to PD-1, optionally followed by a linker sequence at least 80%, at least 90%, or at least 95% identical to SEQ ID NO: 44; (b) a second binding domain that binds to CD1a; (c) a linker sequence at least 80%, at least 90%, or at least 95% identical to SEQ ID NO: 44 followed by an 1gG hinge sequence at least 80%, at least 90%, or at least 95% identical to SEQ ID NO: 43; (d) an Fc region having the sequence at least 80%, at least 90%, or at least 95% identical to SEQ ID NO: 18; (e) a linker sequence at least 80%, at least 90%, or at least 95% identical to SEQ ID NO: 47 followed by an 1gG hinge sequence at least 80%, at least 90%, or at least 95% identical to SEQ ID NO: 43; and (f) an Fc region having the sequence at least 80%, at least 90%, or at least 95% identical to SEQ ID NO: 38.

In some embodiments, the Fc regions can comprise mutations relative to a wild-type or unmodified Fc sequence. Mutations include substitutions, insertions and deletions. Such mutations can be made for the purpose of introducing desirable therapeutic properties. For example, to facilitate hetero-dimerization, knobs into holes (KiH) mutations can be engineered into the CH3 domain. Thus, in some embodiments, the half-life extending domain can comprise one or more amino acid substitutions which facilitate dimerisation of the FC1 region and the FC2 region. Such substitutions include "Knob-in-hole" substitutions. In this case, one chain (i.e. one of the FC1 or FC2 regions) is engineered to contain a bulky protruding residue (i.e. the knob), such as Y, and the other chain (i.e., the other of the FC1 and FC2 regions) is engineered to contain a complementary pocket (i.e. the hole). For example, a knob can be constructed by replacing a small amino acid side chain with a larger side chain. In some embodiments, a hole can be constructed by replacing a large amino acid side chain with a smaller side chain. Without wishing to be bound to theory, this is thought to stabilize a hetero-dimer of the FC1 and FC2 regions by favouring formation of the hetero-dimer over other species, for example homomultimers of FC1 and FC2, thereby enhancing the stability and manufacturability of the multi-domain binding molecule of the disclosure.

Suitable positions and substitutions for KiH mutations, and other mutations for facilitating dimerization of Fc regions, are known in the art. For example, the substitutions forming corresponding knobs and holes in two Fc regions can correspond to one or more pairs provided in the following table:

| CH3 of one of the FC1 and FC2 regions | CH3 of the other of the FC1 and FC2 regions |
|---|---|
| T366Y | Y407T |
| T366W | Y407A |
| T366W | T366S:L368A:Y407V |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

The substitutions in the table above are denoted by the original residue, followed by the position using the EU numbering system as set forth in Kabat, and then the import residue (all residues are given in single-letter amino acid code). Multiple substitutions are separated by a colon.

In some embodiments, the FC1 and FC2 regions can comprise one or more substitutions in the table above. For example:

(i) one of the FC1 region and the FC2 region can comprise one or more amino acid substitutions selected from the group consisting of T366S, L368A, T394S, F405A, Y 407 A, Y 407T and Y407V, according to the EU numbering scheme at set forth in Kabat; and (ii) the other of the FC1 region and the FC2 region can comprise one or more amino acid substitutions selected from the group consisting of T366W, T366Y, T366W, T394W and F405W according to the EU numbering scheme as set forth in Kabat. The substitutions in (i) and (ii) are hole-forming and knob-forming substitutions respectively. The FC1 region can comprise one or more of the substitutions in (i) and the FC2 region can comprise one or more of the substitutions in (ii).

For example:

(i) one of the FC1 region and the FC2 region can comprise one or more amino acid substitutions selected from the group consisting of T366S, L368A, and Y 407V, according to the EU numbering scheme as set forth in Kabat; and (ii) the other of the FC 1 region and the FC2 region can comprise a T366W amino acid substitution, according to the EU numbering scheme as set forth in Kabat. The FC1 region can comprise one or more of the substitutions in (i) and the FC2 region can comprise the substitution in (ii).

In some embodiments, (i) one of the FC1 region and the FC2 region comprises T366S, L368A, and Y407V amino acid substitutions, according to the EU numbering scheme as set forth in Kabat; and (ii) the other of the FC1 region and the FC2 region comprises a T366W amino acid substitution, according to the EU numbering scheme as set forth in Kabat. For example, the FC1 region can comprise T366S, L368A, and Y407V amino acid substitutions, according to the EU numbering scheme as set forth in Kabat; and the FC2 region can comprise a T366W amino acid substitution, according to the EU numbering scheme as set forth in Kabat.

In some embodiments, the Fc domain can also comprise one or more mutations that attenuate an effector function of the Fc domain. Exemplary effector functions include, without limitation, complement-dependent cytotoxicity (CDC) and/or antibody-dependent cellular cytotoxicity (ADCC). The modification to attenuate effector function can be a modification that alters the glycosylation pattern of the Fc domain, e.g., a modification that results in an aglycosylated Fc domain. Alternatively, the modification to attenuate effector function can be a modification that does not alter the glycosylation pattern of the Fc domain. The modification to attenuate effector function can reduce or eliminate binding to human effector cells, binding to one or more Fc receptors, and/or binding to cells expressing an Fc receptor. For example, the half-life extending domain can comprise one or more amino acid substitutions selected from the group consisting of S228P, E233P, L234A, L235A, L235E, L235P, G236R, G237A, P238S, F241A, V264A, D265A, H268A, D270A, N297A, N297G, N297Q, E318A, K322A, L328R, P329G, P329A, A330S, A330L, P331A and P331S, according to the EU numbering scheme as set forth in Kabat. Particular modifications include a N297G or N297 A substitution in the Fc region of human 1gG1 (EU numbering as set forth in Kabat). Other suitable modifications include L234A, L235A and P329G substitutions in the Fc region of human 1gG1 (EU numbering as set forth in Kabat), that result in attenuated effector function. In some embodiments, the Fc regions in the multidomain binding molecule of the disclosure can comprise a substitution at residue N297, numbering according to EU index as set forth in Kabat. For example, the substitution can be an N297G or N297A substitution. Other suitable mutations (e.g., at residue N297) are known to those skilled in the art.

In some embodiments, Fc variants having reduced effector function refers to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wildtype Fc region (e.g., an Fc region not having a mutation to reduce effector function, although it can have other mutations). In some embodiments, the Fc variants having reduced effector function can be Fc variants that eliminate all detectable effector function as compared to a wild-type Fc region. Assays for measuring effector function are known in the art and described below.

In vitro and/or in vivo cytotoxicity assays can be conducted to confirm the reduction/depletion of CDC and/or ADCC activities. For example, Fc receptor (FcR) binding assays can be conducted to ensure that the Fc region or fusion protein lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)).

In some embodiments, substitutions can be introduced into the FC1 and FC2 regions that abrogate or reduce binding to Fcγ receptors and/or to increase binding to FcRn, and/or prevent Fab arm exchange, and/or remove protease sites. In this regard, the half-life extending domain can also comprise one or more amino acid substitutions which prevent or reduce binding to activating receptors. In some embodiments, the half-life extending domain can comprise one or more amino acid substitutions which prevent or reduce binding to FcγR. For example, the FC1 region and/or the FC2 region can comprise a N297G amino acid substitution, according to the EU numbering scheme as set forth in Kabat. Both the FC1 region and the FC2 region can comprise the N297G amino acid substitution.

In some embodiments, the half-life extending domain can comprise one or more amino acid substitutions which promote binding to FcRn. Methods of measuring binding to FcRn are known to the skilled artisan. Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered.

In some embodiments, mutations can be made for manufacturing reasons, for example to remove or replace amino acids that can be subject to post-translational modifications such as glycosylation, as described herein. In some embodiments, the immunoglobulin Fc can be fused to the other domains (i.e., VC1 or VC2) in the molecule of the disclosure via a linker, and/or a hinge sequence as described herein. Alternatively, no linker can be used.

In some embodiments, the two Fc regions in the molecule of the disclosure can comprise CH2 and CH3 constant domains and all or part of a hinge sequence. In some embodiments, the hinge sequence can correspond substantially or partially to a hinge region from 1gG1, 1gG2, 1gG3 or 1gG4. The hinge sequence can be an 1gG1 hinge sequence, such as the amino acid sequence provided in SEQ ID NO: 43. In some embodiments the hinge can comprise all or part of a core hinge domain and all or part of a lower hinge region.

In some embodiments, the multi-domain molecule comprises the amino acid sequence provided in SEQ ID NO: 57 and 58, also known as CD1a-PD-1-1mmTAAI. In some embodiments, cell-bound CD1a-PD-1-1mmTAAI inhibits CD4 T cell activation and enhances CD4 T cell exhaustion. In some embodiments, these molecules exhibit picomolar potency in assays of PD-1-mediated T cell suppression and blockade of CD1a-autoreactive T cell activation. In some embodiments, activity is dependent on 1mmTAAI tethering to target cells and the molecules are inactive in assays using CD1a-negative or CD1b-d+ target cells. In some embodiments, CD1a-targeted PD-1 agonist 1mmTAAIs deliver localized inhibition of inflammatory T cells whilst avoiding systemic immunosuppression. In some embodiments, the CD1a-PD-1-1mmTAAI provides two modes of action, or at least one mode of action. In some embodiments, the CD1a-PD-1-1mmTAAI long-term pharmacodynamic effect on CD4 T cell is an advantage compared to competitor drugs. In some embodiments, the competitor drugs comprise corticosteroids, calcineurin inhibitors, anti-H1 antihistamines, allergen specific immunotherapy, Cyclosporin A, Methotrexate, Azathioprine, Mycophenolate mofetil, Crisaborole, Difamilast, Roflumilast, Ruxolitinib, Peresolimab, Abrocitinib, Upadacitinib, Tofacitinib, Brepocitinib, Baricitinib, Tapinarof, Asivatrep, Dupilumab, Tralokinumab, Lebrikizumab, Nemolizumab, Tezepelumab, Fezakinumab, GBR 830 Rocatinlimab, Omalizumab, Mepolizumab, Ustekinumb, Risakizumab, Secukinumab, Itepekimab, or any combination thereof.

In some embodiments, the disclosure comprises a method of making the multi-domain molecule, comprising maintaining the host cell described above under optimal conditions for expression of the nucleic acid and isolating the multi-domain molecule. In some embodiments, the method comprises culturing a cell comprising a nucleic acid, wherein the nucleic acid encodes the multi-domain molecule. In some embodiments, the method comprises an expression vector comprising the nucleic acid encoding the multi-domain molecule. In some embodiments, the method comprises culturing a host cell comprising the nucleic acid or the vector of this aspect, and then expressing the multi-domain molecule in the cell and secreting it from the cell into the host cell culture supernatant.

Method of Making the Multi-Domain Molecule

The disclosure herein provides a method of producing the multi-domain molecule or single domain antibody, the method comprising a) maintaining the cell under optimal conditions for expression of the multi-domain molecule or single domain antibody as described herein and b) isolating the multi-domain molecule or single domain antibody.

In some embodiments, the disclosure provides a nucleic acid, and/or a cell comprising a nucleic acid encoding the multi-domain molecule of the disclosure, which can be used to express the multi-domain molecule, and then the methods as described herein can be used to purify the multi-domain molecule from the host cell. The nucleic acid can be cDNA. The nucleic acid can be mRNA. The nucleic acid can be non-naturally occurring and/or purified and/or engineered. The nucleic acid sequence can be codon optimized, in accordance with the expression system utilized. As is known to those skilled in the art, expression systems can include bacterial cells such as *E. coli*, or yeast cells, or mammalian cells, or insect cells, or they can be cell free expression systems. Thus, in some embodiments, the methods described herein provide for expressing the multi-domain molecule in a host cell, wherein the multi-domain molecule is secreted into a host cell culture supernatant before the isolating the supernatant of the host cell culture comprising the multi-domain molecule. In some embodiments, the host cell for expressing multi-domain molecule is a mammalian cell.

The present disclosure also provides constructs in the form of plasmids, vectors, transcription or expression cassettes which comprise at least one nucleic acid as described above. The present disclosure also provides a recombinant host cell which comprises one or more constructs as above. As mentioned, a nucleic acid encoding a specific multi-domain molecule of the disclosure forms an aspect of the present disclosure, as does a method of production of the specific binding molecule comprising expression from a nucleic acid encoding a specific binding molecule of the disclosure. In some embodiments, expression can conveniently be achieved by culturing recombinant host cells containing the nucleic acid under appropriate conditions. Following production by expression, a specific multi-domain molecule can be isolated and/or purified using any suitable technique, then used as appropriate.

Systems for cloning and expression of a polypeptide, i.e., the muti-domain molecule, in a variety of different host cells are well known. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*. The expression of antibodies and antibody fragments in prokaryotic cells such as *E. coli* is well established in the art. For a review, see for example Plückthun, Bio/Technology 9:545-551 (1991). Expression in eukaryotic cells in culture is also available to those skilled in the art as an option for production of a specific binding molecule, see for recent review, for example Reff, Curr. Opinion Biotech. 4:573-576 (1993); Trill et al., Curr. Opinion Biotech. 6:553-560 (1995).

Suitable vectors can be chosen or constructed, containing appropriate regulatory sequences, including promoter sequences, terminator sequences, polyadenylation sequences, enhancer sequences, marker genes and other sequences as appropriate. Vectors can include be any suitable vectors known in the art, including plasmids or viral vectors (e.g. 'phage, or phagemid), as appropriate. For further details see, for example, Sambrook et al., Molecular Cloning: A Laboratory Manual: $2^{nd}$ Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, 2nd Edition, John Wiley & Sons (1992).

The present disclosure also provides a host cell containing a nucleic acid encoding the multi-domain as disclosed herein. Further, the disclosure provides a method comprising introducing such nucleic acid into a host cell. The introduction can employ any available technique. For eukaryotic cells, suitable techniques can include calcium phosphate transfection, DEAE-Dextran, electroporation, liposome-mediated transfection and transduction using retrovirus or other virus, e.g. vaccinia or, for insect cells, baculovirus. For bacterial cells, suitable techniques can include calcium chloride transformation, electroporation and transfection using bacteriophage. The introduction can be followed by causing or allowing expression from the nucleic acid, e.g. by culturing host cells under conditions for expression of the gene.

Suitable host cells for cloning or expression of polynucleotides and/or vectors of the present disclosure are known in the art. Suitable host cells for the expression of (glycosylated) proteins are also derived from multicellular organisms (invertebrates and vertebrates). Examples of invertebrate cells include plant and insect cells. Numerous baculoviral strains have been identified which can be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants). Vertebrate cells can also be used as hosts. For example, mammalian cell lines that are adapted to grow in suspension can be useful. other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse Sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MOCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as YO, NS0 and Sp2/0. For a review of certain mammalian host cell lines suitable for protein production, see, e.g., Yazaki, P. and Wu, A. M., Methods in Molecular Biology, Vol. 248, Lo, B. K. C. (ed.), Humana Press, Totowa, NJ (2004), pp. 255-268. The host cell can be eukaryotic, e.g., a Chinese Hamster Ovary (CHO) cell or lymphoid cell (e.g., YO, NS0, Sp20 cell).

In some embodiments, the nucleic acid of the disclosure can be integrated into the genome (e.g. chromosome) of the host cell. In some embodiments, integration can be promoted by inclusion of sequences which promote recombination with the genome, in accordance with standard techniques.

Further provided herein are methods for making the multi-domain molecules described herein. The methods comprise maintaining the host cell of the disclosure under optimal conditions for expression of the nucleic acid or expression vector of the disclosure and isolating the multi-domain molecule.

Methods of producing recombinant proteins such as multi-domain molecules are well known in the art. Nucleic acids encoding the protein can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary mammalian cells used for expressing a protein are CHO cells, myeloma cells or HEK cells. Molecular cloning techniques to achieve these ends are known in the art and described, for example in Ausubel et al. (editors), Current Protocols in Molecular Biology, Greene Pub. Associates and Wiley-Interscience (1988, including all updates until present) or Sambrook et al. Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

In some embodiments, the nucleic acid encoding the multi-domain molecule can be inserted operably linked to a promoter in an expression construct or expression vector for further cloning (amplification of the DNA) or for expression in a cell-free system or in cells. As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid. As used herein, the term "operably linked to" means positioning a promoter relative to a nucleic acid such that expression of the nucleic acid is controlled by the promoter.

Many vectors for expression of a protein in cells, e.g., the multi-domain molecules, are commercially available. The vector components generally include, but are not limited to, one or more of the following: a signal sequence, a sequence encoding a protein (e.g., derived from the information provided herein), an enhancer element, a promoter, and a transcription termination sequence. The skilled person will be aware of suitable sequences for expression of a protein. Exemplary signal sequences include prokaryotic secretion signals (e.g., pel B, alkaline phosphatase, penicillinase, 1pp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-a promoter (EF1), small nuclear RNA promoters (Ula and Ulb), a-myosin heavy chain promoter, Simian virus 40 promoter (SV40), Rous sarcoma virus promoter (RSV), Adenovirus major late promoter, !3-actin promoter; hybrid regulatory element comprising a CMV enhancer/!3-actin promoter or an immunoglobulin promoter or an active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 1 O); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADHI promoter, the GAL 1 promoter, the GALA promoter, the CUP1 promoter, the PHOS promoter, the nmt promoter, the RPR 1 promoter, or the TEF1 promoter.

The host cells used to produce the protein can be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Methods of Treating Autoimmune Conditions

The present disclosure includes methods which comprise administering to a subject in need thereof a therapeutic composition comprising the multi-domain molecule. As used herein, the expression "a subject in need thereof" means a human or non-human animal that exhibits one or more symptoms or indicia of an autoimmune condition. In some embodiments, the autoimmune disease is atopic dermatitis, diabetes, e.g., type 1 diabetes, allergic rhinitis, asthma, Crohn's disease, psoriasis and/or skin lichenoid diseases. In some embodiments, "a subject in need thereof" means a human or non-human animal, and/or who has been diagnosed with an autoimmune disease, e.g., atopic dermatitis, diabetes, e.g., type 1 diabetes, allergic rhinitis, asthma, Crohn's disease, psoriasis and/or skin lichenoid diseases. In some embodiments, "a subject in need thereof" means a human or non-human animal, and/or who has been diagnosed with being predisposed to an autoimmune disease, e.g., atopic dermatitis, diabetes, e.g., type 1 diabetes, allergic rhinitis, asthma, Crohn's disease, psoriasis and/or skin lichenoid diseases, independent of whether any symptoms of such disease have been manifest.

In some embodiments, the disclosure provides a method of treating atopic dermatisis. Atopic dermatitis (AD) is a chronic/relapsing inflammatory skin disease characterized by intense pruritus (i.e., itchiness), xerosis (skin dryness), and eczematous lesions whose features include erythema, infiltration/papulation, oozing with crusting, excoriations, and lichenification. Thus, in some embodiments, the disclosure provides a method of reducing pruritus (i.e., itchiness), xerosis (skin dryness), and eczematous lesions. It is often associated with other atopic disorders, such as allergic rhinitis and asthma. Severe disease can be extremely disabling due to several factors: major psychological problems, significant sleep loss, and impaired quality of life (QOL) that lead to a high socioeconomic cost. An estimated 2% to 10% of adults are affected by AD (Bieber 2008, N. Engl. J. Med. 358:1483-94).

The pathophysiology of AD is influenced by a complex interplay between inflammation, environmental factors, genetics and skin barrier dysfunction. AD is the most common inflammatory skin disease in childhood (Illi et al 2004, J. Allergy Clin. Immunol. 113:925-31). The disease usually presents during early infancy and childhood, but it can persist into or start in adulthood (Kay et al 1994, J. Am. Acad. Dermatol. 30:35-9). The disease affects 15 to 30% of children and 2 to 10% of adults in industrialized countries (Bieber 2008, N. Engl. J. Med. 358:1483-94). Phase 1 of the International Study of Asthma and Allergies in Childhood showed a 1-year period prevalence rate as high as 20% in Australia, England, and Scandinavia (Williams et al 1999, J. Allergy Clin. Immunol. 103:125-38). Often AD constitutes the first step of atopic march (progression from one atopic disease to another). Approximately up to 60% of AD patients have concomitant asthma or allergic rhinitis or food allergy (Hong et al 2012, Envt. Health Toxicol. 27: e2012006).

Topical corticosteroids (TCS) are frequently prescribed for treatment of AD patients. However, long-term application of TCS is not recommended because of the risk of skin atrophy, dyspigmentation, acneiform eruptions, and risks associated with systemic absorption (e.g., hypothalamic pituitary axis effects, Cushing's disease, etc.). Topical calcineurin inhibitors (TCI) are generally effective and safe as short-term treatments, but concerns of skin malignancies and increased risk of lymphomas have prompted regulatory authorities to require a warning regarding the long-term safety of topical tacrolimus and pimecrolimus in their prescribing information. Repeated application of any topical therapy over a long period of time or to large surface areas also leads to reduced patient compliance. First generation antihistamines are widely prescribed for acute symptomatic treatment of pruritus, although their effectiveness is limited and largely attributed to their sedating effect. Oral immunosuppressants (Schmitt et al 2007, JEADV 21:606-619) and glucocorticoids are effective, but are sometimes associated with severe toxicity and side effects, thus limiting their use to short courses and/or intermittent therapy. No systemic agents are approved in the treatment of AD in children. All systemic agents are used off label (cyclosporine, methotrexate, azathioprine, mycophenolate mofetil, systemic corticosteroids) and lack evidence basis of use. All of these agents have a broad immunosuppressive effect which predisposes the patients to serious infections and increased risk of malignancies if used for prolonged periods. Other reported significant side effects with these agents include gastritis, stunted growth, diabetes, weight gain, hypertension, osteoporosis and adrenal suppression (corticosteroids), nephrotoxicity, hypertension, tremor, hypertrichosis, headache, gingival hyperplasia (cyclosporine), gastrointestinal disturbances, ulcerative stomatitis, myelosuppression, hepatotoxicity and pulmonary fibrosis (methotrexate), hypersensitivity reactions, elevated liver enzymes and leukopenia (azathioprine). Moreover, a high proportion of patients in which disease is initially controlled by systemic agents suffer from relapse once therapy is discontinued (Granlund et al 1995, Br. J. Dermatol. 132: 106-112; Schmitt et al 2009, Br. J. Dermatol. 162:661-8).

In some embodiments, the present disclosure provides a method for measuring levels of soluble PD-1 (sPD1) from a sample in the subject. In embodiments, increased levels of soluble PD-1 (sPD1) indicate PD-1 binding and engagement. In embodiments, increased levels of soluble PD-1 (sPD1) indicate CD1a binding and engagement. In embodiments, increased levels of soluble PD-1 (sPD1) indicate simultaneous CD1a and PD-1 binding and engagement.

In some embodiments, the present disclosure provides a method for measuring engagement, or efficacy of engagement, of the multi-domain molecule, the single domain antibody, or the bispecific molecule described herein with a target PD-1 marker and/or a target CD1a marker, in a subject, wherein the method comprises administering to the subject the multi-domain molecule, single domain antibody, or bispecific molecule and measuring a level of soluble PD-1 (sPD-1) in a biological sample obtained from the subject. In embodiments, a relative increase in the measured level of sPD-1 indicates engagement of the multi-domain molecule, single domain antibody, or bispecific molecule with the target PD-1 marker and/or target CD1a marker. In embodiments, the measured level of sPD-1 is increased at least about 1.5 fold, about 2 fold, about 3 fold, about 4 fold, about 5 fold, about 6 fold, about 7 fold, about 8 fold, about 10 fold, or about 20 fold relative to a sample obtained from a subject not treated with the multi-domain molecule, single domain antibody, or bispecific molecule of the present disclosure.

In some embodiments, the present disclosure provides a method of treating an autoimmune disease in a subject, the method comprising: (i) determining a baseline level (T0) of soluble PD-1 (sPD-1) in a biological sample obtained from the subject, (ii) administering to the subject a first dosage amount of a multi-domain molecule binding to PD-1 and CD1a, and (iii) determining a level of sPD-1 (T1) after (ii) in a biological sample obtained from the subject. In embodiments, if the T1 level of sPD-1 is greater than or equal to the T0 level, then a second dosage amount of the multi-domain molecule is administered. In embodiments, the second dosage amount is the same or less than the first dosage amount. In embodiments, if the T1 level of sPD-1 is less than T0, then the second dosage amount of the multi-domain molecule is greater than the first dosage amount and/or further comprises administering a second autoimmune disease treatment.

In some embodiments, the present disclosure provides a method of enhancing T cell exhaustion comprising administering a multi-domain molecule simultaneously targeting PD-1 and CD1a. In embodiments, T cell activation is reduced following administration of the multi-domain molecule. In embodiments, cytokine release is reduced following administration of the multi-domain molecule.

Description of the Sequences

TABLE 1

| SEQ ID NO: | Description | Sequence |
|---|---|---|
| 1 | First binding domain, CDR1 | GFTFSSYA |
| 2 | First binding domain, CDR2 | IASDGAST |
| 3 | First binding domain, CDR3 | CARGGYLTYDRY |
| 4 | Second binding domain, CDR1 Ab002 | GRTFNPGDLMG |
| 5 | Second binding domain, CDR1 Ab007 | GRAFRPHNVMA |
| 6 | Second binding domain, CDR1 Ab052 | GRTFSPSDLMG |
| 7 | Second binding domain, CDR2 Ab002 | AIKWGPTYYADSVKG |
| 8 | Second binding domain, CDR2 Ab007 | AARWSGIYYAESVKG |
| 9 | Second binding domain, CDR2 Ab052 | AIKWGPTYYSDSVKG |
| 10 | Second binding domain, CDR3 Ab002 | GSGTFSSNYRDFEY |
| 11 | Second binding domain, CDR3 Ab007 | STAQDMTLALMSDYDY |
| 12 | Second binding domain, CDR3 Ab052 | GSSTFSANYRDYEY |
| 13 | amino acid sequence of the extracellular region of human PD-1 (bold residues are in the epitope of the VHH provided in SEQ ID NOs: 18 and 20): | FLDSPDRPWNPPTFSPALLVVTEGDNATFTCSFS NTS**E**SFVLNWYRMSPSNQTDKLAA**FPE**DRSQP GQDCRFRV**TQLPNG**RDFHMSVVRARRNDSGT YLCGAISLAPKAQIKESLRAELRVTERRAEVPTA HPSPSPRPAGQFQTLV |
| 14 | First binding domain, FR1 | AVQLVESGGGLVQPGGSLRLSCAAS |
| 15 | First binding domain, FR2 | MTWVRQAPGKGPEWVSA |
| 16 | First binding domain, FR3 | SYADSVKGRFTISRDNSKNTLYLQMNSLRPEDT AVYY |
| 17 | First binding domain, FR4 | YLTYDRYGQGTLVTVSS |
| 18 | amino acid sequence of an exemplary camelid PD-1 agonist VHH. The CDRs (CDR1, CDR2 and CDR3) are underlined and are designated SEQ ID NO: 1, 2 and 3 respectively. Positions different from the human IgHV3-23 consensus are shown in bold. | **E**VQL**V**ESGG**A** LVQPGGSLRL SCAASGFTFS SYAM**T**WVRQA PGKG**P**EWVS**A** IASDGAST**S**Y **L**DSVKGRFT**V** SRDN**A**KNTLY LQMNSL**KP**ED TAVYYCARGGYLTYDRYGQG T**Q**VTVSS |
| 19 | amino acid sequence of a soluble fragment of human PD-L1 that is capable of binding to PD-1: | FTVTVPKDLYWEYGSNMTIECKFPVEKQLDLAA LIVYWEMEDKNIIQFVHGEEDLKVQHSSYRQRA RLLKDQLSLGNAALQITDVKLQDAGVYRCMISY GGADYKRITVKVNAPY |
| 20 | SEQ ID NO: 20 (H5) is the amino acid sequence of a humanized version of the exemplary PD-1 agonist VHH of SEQ ID NO: 18. | **A**VQLVESGG**G**LVQPGGSLRLSCAASGFTFSSYA MTWVRQAPGKGPEWVSAIASDGASTSY**A**DSVK GRFT**I**SRDN**S**KNTLYLQMNSL**R**PEDTAVYYCAR GGYLTYDRYGQGT**L**VTVSS |

TABLE 1-continued

| SEQ ID NO: | Description | Sequence |
|---|---|---|
| | Mutations relative to SEQ ID NO: 18 are shown in bold. | |
| 21 | Second binding domain, Ab002.10. Residues that mismatch with human FW sequences are bolded | EVQLLESGGGLVQPGGSLRLSCA**PSGRTFNPGD LMG**W**F**RQAPGK**ERE**F**VAAIKWGPTYYADSV KG**RFTISRD**Y**SKNT**V**YLQMNSLRAEDTAVYYC A**GKGSGTFSSNYRDFEY**WGQGTLVTVSS |
| 22 | Second binding domain, Ab002.10.5nR: | EVQLLESGGGLVQPGGSLRLSCA**PSGRTFNPGD LMG**W**F**RQAPGK**ERE**FVS**AIKWGPTYYADSVK G**RFTISRD**Y**S**R**NTLYLQMNSLRAEDTAVYYCA AK**GSGTFSSNYRDFEY**WGQGTLVTVSS |
| 23 | Second binding domain, Ab002.10.5n: | EVQLLESGGGLVQPGGSLRLSCA**PSGRTFNPGD LMG**W**F**RQAPGK**ERE**FVS**AIKWGPTYYADSVK G**RFTISRD**Y**SKNTLYLQMNSLRAEDTAVYYCA AK**GSGTFSSNYRDFEY**WGQGTLVTVSS |
| 24 | Second binding domain, Ab002.10.17nR: | EVQLLESGGGLVQPGGSLRLSCA**PSGRTFNPGD LMG**W**F**RQAPGKG**RE**F**VS**AIKWGPTYYADSVK G**RFTISRD**Y**S**R**NT**V**YLQMNSLRAEDTAVYYCA AK**GSGTFSSNYRDFEY**WGQGTLVTVSS |
| 25 | Second binding domain, Ab002.10.18nR: | EVQLLESGGGLVQPGGSLRLSCA**PSGRTFNPGD LMG**W**F**RQAPGKGLE**F**VS**AIKWGPTYYADSVK G**RFTISRD**Y**S**R**NTVYLQMNSLRAEDTAVYYCA AK**GSGTFSSNYRDFEY**WGQGTLVTVSS |
| 26 | Second binding domain, Ab002.10.21nR: | EVQLLESGGGLVQPGGSLRLSCA**PSGRTFNPGD LMG**W**F**RQAPGKG**RE**F**VS**AIKWGPTYYADSVK G**RFTISRD**Y**S**R**NTLYLQMNSLRAEDTAVYYCA AK**GSGTFSSNYRDFEY**WGQGTLVTVSS |
| 27 | Second binding domain, Ab002.10.21n: | EVQLLESGGGLVQPGGSLRLSCA**PSGRTFNPGD LMG**W**F**RQAPGKG**RE**F**VS**AIKWGPTYYADSVK G**RFTISRD**Y**SKNTLYLQMNSLRAEDTAVYYCA AK**GSGTFSSNYRDFEY**WGQGTLVTVSS |
| 28 | Second binding domain, Ab007.11 | EVQLLESGGGLVQPGGSLRLSCAAS**GRAFRPH NVMA**WFRQAPGKEREFV**AAARWSGIYYAESV KG**RFTISRDYSKNTVYLQMNSLRPEDTAVYYC AV**STAQDMTLALMSDYDY**WGQGTLVTVSS |
| 29 | Second binding domain, Ab052.9 | EVQLLESGGGLVQPGGSLRLSCAAS**GRTFSPSD LMG**WFRQAPGKEREFV**AAIKWGPTYYSDSVK G**RFTISRDYSKNTVYLQMNSLRAEDTAVYYCA **G**K**GSSTFSANYRDYEY**WGQGTLVTVSS |
| 30 | Second binding domain, FR1 (most humanized form) | EVQLLESGGGLVQPGGSLRLSCAAS |
| 31 | Second binding domain, FR2 (most humanized form) | WVRQAPGKGLEWVS |
| 32 | Second binding domain, FR3 (most humanized form) | RFTISRDNSKNTLYLQMNSLRAEDTAVYYCAAK |
| 33 | Second binding domain, FR4 (most humanized form) | WGQGTLVTVSS |
| 34 | Second binding domain, Ab002 Llama WT | EVQLVESGGGLVQAGGSLRLSCAPSGRTFNPGD LMGWFRQAPGKEREFVAAIKWGPTYYADSVKG RFTISRDYVRNTVYVQMNDLKAEDTAVYYCAG KGSGTFSSNYRDFEYWGQGTQVTVSS |
| 35 | Second binding domain, Ab007 Llama WT | EVQLVESGGRLAQAGGSLRLSCAASGRAFRPHN VMAWFRQAPEKEREFVAAARWSGIYYAESVKG RFSVSRDYDKNAVFLQMNGLKPEDTAVYYCAV STAQDMTLALMSDYDYWGQGIQVTVSS |

TABLE 1-continued

| SEQ ID NO: | Description | Sequence |
|---|---|---|
| 36 | Second binding domain, Ab052 Llama WT | EVQLVESGGGLVQAGGSLRLSCAASGRTFSPSD<br>LMGWFRQAPGKEREFVAAIKWGPTYYSDSVKG<br>RFTTSRDYVGNTVYLQMNDLKAEDTAVYHCA<br>GKGSSTFSANYRDYEYWGQGTQVTVSS |
| 37 | Human IgG1 Fc region (CH2 and CH3 domains), unmodified | APELLGGPSVFLFPPKPKDTLMISRTPEVTCVVV<br>DVSHEDPEVKFNWYVDGVEVHNAKTKPREEQY<br>NSTYRVVSVLTVLHQDWLNGKEYKCKVSNKAL<br>PAPIEKTISKAKGQPREPQVYTLPPSRDELTKNQ<br>VSLTCLVKGFYPSDIAVEWESNGQPENNYKTTP<br>PVLDSDGSFFLYSKLTVDKSRWQQGNVFSCSV<br>MHEALHNHYTQKSLSLSPGK |
| 38 | IgG1 Fc region sequence with four substitutions, (bold), relative to the above unmodified IgG1 Fc sequence. These are an N297G substitution for inhibiting binding to FcγR as well as a T366S, L368A, and Y407V substitutions (hole-forming substitutions) for enhancing dimerization with another Fc region (e.g., SEQ ID NO: 40) | APELLGGP SVFLFPPKPK DTLMISRTPE<br>VTCVVVDVSH EDPEVKFNWY VDGVEVHNAK<br>TKPREEQY**G**S TYRVVSVLIV LHQDWLNGKE<br>YKCKVSNKAL PAPIEKTISK AKGQPREPQV<br>YTLPPSRDEL TKNQVSL**S**C**A** VKGFYPSDIA<br>VEWESNGQPE NNYKTTPPVL DSDGSFFL**V**S<br>KLTVDKSRWQ QGNVFSCSVM HEALHNHYTQ<br>KSLSLSPGK |
| 39 | IgG1 Fc region sequence identical to SEQ ID NO: 38 above except that it has additional M252Y, S254T and T256E substitutions (EU numbering scheme as set forth in Kabat), shown in bold, to enhance binding to FcRn | APELLGGP SVFLFPPKPK DTL**Y**I**T**R**E**PE<br>VTCVVVDVSH EDPEVKFNWY VDGVEVHNAK<br>TKPREEQYGS TYRVVSVLTV LHQDWLNGKE<br>YKCKVSNKAL PAPIEKTISK AKGQPREPQV<br>YTLPPSRDEL TKNQVSLSCA VKGFYPSDIA<br>VEWESNGQPE NNYKTTPPVL DSDGSFFLVS<br>KLTVDKSRWQ QGNVFSCSVM HEALHNHYTQ<br>KSLSLSPGK |
| 40 | IgG1 Fc region sequence having two substitutions, (bold), relative to the above unmodified IgG1 Fc sequence (SEQ ID NO: 37). These are an N297G substitution for inhibiting binding to FcγR as well as a T366W substitution (knob-forming substitution) for enhancing dimerization with another Fc region (e.g., SEQ ID NO: 38) containing T366S, L368A, and Y407V substitutions (hole-forming substitutions). | APELLGGP SVFLFPPKPK DTLMISRTPE<br>VTCVVVDVSH EDPEVKFNWY VDGVEVHNAK<br>TKPREEQY**G**S TYRVVSVLTV LHQDWLNGKE<br>YKCKVSNKAL PAPIEKTISK AKGQPREPQV<br>YTLPPSRDEL TKNQVSL**W**CL VKGFYPSDIA<br>VEWESNGQPE NNYKTTPPVL DSDGSFFLYS<br>KLTVDKSRWQ QGNVFSCSVM HEALHNHYTQ<br>KSLSLSPGK |
| 41 | IgG1 Fc region sequence identical to SEQ ID NO: 40 above except that it has additional M252Y, S254T and T256E substitutions (EU numbering scheme as set forth in Kabat), shown in bold, to enhance binding to FcRn | APELLGGP SVFLFPPKPK DTL**Y**I**T**R**E**PE<br>VTCVVVDVSH EDPEVKFNWY VDGVEVHNAK<br>TKPREEQYGS TYRVVSVLTV LHQDWLNGKE<br>YKCKVSNKAL PAPIEKTISK AKGQPREPQV<br>YTLPPSRDEL TKNQVSLWCL VKGFYPSDIA<br>VEWESNGQPE NNYKTTPPVL DSDGSFFLYS<br>KLTVDKSRWQ QGNVFSCSVM HEALHNHYTQ<br>KSLSLSPGK |
| 42 | IgG hinge sequence at the N-terminus of FC1 or 2 | EPKSSDKTHTCPPCP |
| 43 | IgG hinge sequence at the N-terminus of FC1 or 2 | DKTHTCPPCP |
| 44 | Linker between N-terminus of second binding domain and C-terminus of the first binding domain | GGGGS |

TABLE 1-continued

| SEQ ID NO: | Description | Sequence |
|---|---|---|
| 45 | Linker between N-terminus of second binding domain and C-terminus of the first binding domain | GGGSG |
| 46 | Linker between N-terminus of second binding domain and C-terminus of the first binding domain | GGSGG |
| 47 | Linker between N-terminus of second binding domain and C-terminus of the first binding domain | GSGGG |
| 48 | Linker between N-terminus of second binding domain and C-terminus of the first binding domain | GSGGGP |
| 49 | Linker between N-terminus of second binding domain and C-terminus of the first binding domain | GGEPS |
| 50 | Linker between N-terminus of second binding domain and C-terminus of the first binding domain | GGEGGGP |
| 51 | Linker between N-terminus of second binding domain and C-terminus of the first binding domain | GGEGGGSEGGGS |
| 52 | Linker between N-terminus of second binding domain and C-terminus of the first binding domain | GGGSGGGG |
| 53 | Linker between N-terminus of second binding domain and C-terminus of the first binding domain | GGGGSGGGGSGGGGSGGGGSGGGS |
| 54 | Linker between N-terminus of second binding domain and C-terminus of the first binding domain | GGGGSGGGGSGGGGSGGGGS |
| 55 | Linker between N-terminus of second binding domain and C-terminus of the first binding domain | EAAAK |
| 56 | Linker between N-terminus of second binding domain and C-terminus of the first binding domain | EAAAKEAAAKEAAAK |
| 57 | Fc Chain 1: E3.12.25-ab002.10-H5-Fc chain (IgG1 truncated hinge N297G knob)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKEREFVAAIKWGPTYYADSVKGRFTISRDY SKNTVYLQMNSLRAEDTAVYYCAGKGSGTFSS NYRDFEYWGQGTLVTVSSDKTHTCPPCPAPELL GGPSVFLFPPKPKDTLMISRTPEVTCVVVDVSHE DPEVKFNWYVDGVEVHNAKTKPREEQYGSTYR VVSVLTVLHQDWLNGKEYKCKVSNKALPAPIE KTISKAKGQPREPQVYTLPPSRDELTKNQVSLW CLVKGFYPSDIAVEWESNGQPENNYKTTPPVLD SDGSFFLYSKLTVDKSRWQQGNVFSCSVMHEA LHNHYTQKSLSLSPGK |

TABLE 1-continued

| SEQ ID NO: | Description | Sequence |
|---|---|---|
| 58 | Fc Chain 2: Fc (IgG1 truncated hinge N297G hole) | DKTHTCPPCPAPELLGGPSVFLFPPKPKDTLMIS RTPEVTCVVVDVSHEDPEVKFNWYVDGVEVHN AKTKPREEQYGSTYRVVSVLTVLHQDWLNGKE YKCKVSNKALPAPIEKTISKAKGQPREPQVYTLP PSRDELTKNQVSLSCAVKGFYPSDIAVEWESNG QPENNYKTTPPVLDSDGSFFLVSKLTVDKSRWQ QGNVFSCSVMHEALHNHYTQKSLSLSPGK |
| 59 | Fc Chain 1: E3.12.25-ab002.10.18nR-H5-Fc chain (IgG1 truncated hinge N297G knob)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKGLEFVSAIKWGPTYYADSVKGRFTISRDY SRNTVYLQMNSLRAEDTAVYYCAAKGSGTFSS NYRDFEYWGQGTLVTVSSDKTHTCPPCPAPELL GGPSVFLFPPKPKDTLMISRTPEVTCVVVDVSHE DPEVKFNWYVDGVEVHNAKTKPREEQYGSTYR VVSVLTVLHQDWLNGKEYKCKVSNKALPAPIE KTISKAKGQPREPQVYTLPPSRDELTKNQVSLW CLVKGFYPSDIAVEWESNGQPENNYKTTPPVLD SDGSFFLYSKLTVDKSRWQQGNVFSCSVMHEA LHNHYTQKSLSLSPGK |
| 60 | Fc Chain 1: E3.12.25-ab002.10.18nR-H5-Fc chain (IgG1 truncated hinge N297G knob with YTE mutation)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKGLEFVSAIKWGPTYYADSVKGRFTISRDY SRNTVYLQMNSLRAEDTAVYYCAAKGSGTFSS NYRDFEYWGQGTLVTVSSDKTHTCPPCPAPELL GGPSVFLFPPKPKDTLYITREPEVTCVVVDVSHE DPEVKFNWYVDGVEVHNAKTKPREEQYGSTYR VVSVLTVLHQDWLNGKEYKCKVSNKALPAPIE KTISKAKGQPREPQVYTLPPSRDELTKNQVSLW CLVKGFYPSDIAVEWESNGQPENNYKTTPPVLD SDGSFFLYSKLTVDKSRWQQGNVFSCSVMHEA LHNHYTQKSLSLSPGK |
| 61 | Fc Chain 2: Fc (IgG1 truncated hinge N297G hole with YTE mutations) | DKTHTCPPCPAPELLGGPSVFLFPPKPKDTLYITR EPEVTCVVVDVSHEDPEVKFNWYVDGVEVHNA KTKPREEQYGSTYRVVSVLTVLHQDWLNGKEY KCKVSNKALPAPIEKTISKAKGQPREPQVYTLPP SRDELTKNQVSLSCAVKGFYPSDIAVEWESNGQ PENNYKTTPPVLDSDGSFFLVSKLTVDKSRWQQ GNVFSCSVMHEALHNHYTQKSLSLSPGK |
| 62 | Fc Chain 1: E3.12.25-Ab002.10-H5-Fc chain (IgG1 truncated hinge N297G knob with YTE mutation)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKEREFVAAIKWGPTYYADSVKGRFTISRDY SKNTVYLQMNSLRAEDTAVYYCAGKGSGTFSS NYRDFEYWGQGTLVTVSSDKTHTCPPCPAPELL GGPSVFLFPPKPKDTLYITREPEVTCVVVDVSHE DPEVKFNWYVDGVEVHNAKTKPREEQYGSTYR VVSVLTVLHQDWLNGKEYKCKVSNKALPAPIE KTISKAKGQPREPQVYTLPPSRDELTKNQVSLW CLVKGFYPSDIAVEWESNGQPENNYKTTPPVLD SDGSFFLYSKLTVDKSRWQQGNVFSCSVMHEA LHNHYTQKSLSLSPGK |
| 63 | Fc Chain 1: E3.12.25-ab002.10.21nR-H5-Fc chain (IgG1 truncated hinge N297G knob)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKGREFVSAIKWGPTYYADSVKGRFTISRDY SRNTLYLQMNSLRAEDTAVYYCAAKGSGTFSS NYRDFEYWGQGTLVTVSSDKTHTCPPCPAPELL GGPSVFLFPPKPKDTLMISRTPEVTCVVVDVSHE DPEVKFNWYVDGVEVHNAKTKPREEQYGSTYR VVSVLTVLHQDWLNGKEYKCKVSNKALPAPIE |

TABLE 1-continued

| SEQ ID NO: | Description | Sequence |
|---|---|---|
| | | KTISKAKGQPREPQVYTLPPSRDELTKNQVSLW CLVKGFYPSDIAVEWESNGQPENNYKTTPPVL DSDGSFFLYSKLTVDKSRWQQGNVFSCSVMHE ALHNHYTQKSLSLSPGK |
| 64 | Fc Chain 1: E3.12.25-ab002.10.21nR-H5-Fc chain (IgG1 truncated hinge N297G knob with YTE mutation)(HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAPSGRTFNPGDLMGWFRQ APGKGREFVSAIKWGPTYYADSVKGRFTISRDY SRNTLYLQMNSLRAEDTAVYYCAAKGSGTFSS NYRDFEYWGQGTLVTVSSDKTHTCPPCPAPELL GGPSVFLFPPKPKDTLYITREPEVTCVVVDVSH EDPEVKFNWYVDGVEVHNAKTKPREEQYGSTY RVVSVLTVLHQDWLNGKEYKCKVSNKALPAPI EKTISKAKGQPREPQVYTLPPSRDELTKNQVSL WCLVKGFYPSDIAVEWESNGQPENNYKTTPPVL DSDGSFFLYSKLTVDKSRWQQGNVFSCSVMHE ALHNHYTQKSLSLSPGK |
| 65 | Second binding domain, Ab092.6 | EVQLLESGGGLVQPGGSLRLSCAASGHAFSDLH MGWFRQAPGKGLEFVSYINWSGRDSKYADSVK DRFTISRDNSKNTLYLQMNSLRAEDTAVYYCAA EKVYYSIVVSDGSQYDYWGQGTLVTVSS |
| 66 | Second binding domain, Ab092 Llama WT | EVQLVESGGGLVQTGGSLRLSCTASGHAFSDLH MGWFRQAPGKEREFVSYINWSGRDSKYADSVK DRFTISRDNAKSTVYLQMNSLKPEDTAVYYCAA EKVYYSIVVSDGSQYDYWGQGTQVTVSS |
| 67 | Second binding domain, Ab096.12 | EVQLLESGGGLVQPGGSLRLSCAASGRTSAHIP MGWFRQAPGKEREFVSAVSWGGTYYADSVKG RFTISRVYAEDNSKNTVYLQMNSLRAEDTAVY YCATRKYATFSTENVDYDYWGQGTLVTVSS |
| 68 | Second binding domain, Ab096 Llama WT | EVQLVESGGGLVQAGGSLRLSCTASGRTSAHIP MGWFRQAPGKEREFVAAVSWGGTYYADSVKG RFTISRVYAEDNVENTVYLQMNSLKREDTAVY YCATRKYATFSTENVDYDYWGQGTQVTVSS |
| 69 | Fc Chain 1: Ab007.11-H5 HLE | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAASGRAFRPHNVMAWFRQ APGKEREFVAAARWSGIYYAESVKGRFTISRDY SKNTVYLQMNSLRPEDTAVYYCAVSTAQDMTL ALMSDYDYWGQGTLVTVSSDKTHTCPPCPAPE LLGGPSVFLFPPKPKDTLMISRTPEVTCVVVDVS HEDPEVKFNWYVDGVEVHNAKTKPREEQYGST YRVVSVLTVLHQDWLNGKEYKCKVSNKALPAP IEKTISKAKGQPREPQVYTLPPSRDELTKNQVSL WCLVKGFYPSDIAVEWESNGQPENNYKTTPPVL DSDGSFFLYSKLTVDKSRWQQGNVFSCSVMHE ALHNHYTQKSLSLSPGK |
| 70 | Fc Chain 1: Ab052.9-H5 HLE | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAASGRTFSPSDLMGWFRQA PGKEREFVAAIKWGPTYYSDSVKGRFTISRDYS KNTVYLQMNSLRAEDTAVYYCAGKGSSTFSAN YRDYEYWGQGTLVTVSSDKTHTCPPCPAPELLG GPSVFLFPPKPKDTLMISRTPEVTCVVVDVSHED PEVKFNWYVDGVEVHNAKTKPREEQYGSTYRV VSVLTVLHQDWLNGKEYKCKVSNKALPAPIEK TISKAKGQPREPQVYTLPPSRDELTKNQVSLWC LVKGFYPSDIAVEWESNGQPENNYKTTPPVLDS DGSFFLYSKLTVDKSRWQQGNVFSCSVMHEAL HNHYTQKSLSLSPGK |
| 71 | Fc Chain 1: Ab092.6-H5 HLE | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG |

TABLE 1-continued

| SEQ ID NO: | Description | Sequence |
|---|---|---|
| | | GGLVQPGGSLRLSCAASGHAFSDLHMGWFRQA PGKGLEFVSYINWSGRDSKYADSVKDRFTISRD NSKNTLYLQMNSLRAEDTAVYYCAAEKVYYSI VVSDGSQYDYWGQGTLVTVSSDKTHTCPPCPA PELLGGPSVFLFPPKPKDTLMISRTPE VTCVVVDVSHEDPEVKFNWY VDGVEVHNAKTKPREEQYGSTYRVVSVLTVLH QDWLNGKEYKCKVSNKALPAPIEKTISKAKGQP REPQVYTLPPSRDELTKNQVSLWCLVKGFYPSD IAVEWESNGQPENNYKTTPPVLDSDGSFFLYSK LTVDKSRWQQGNVFSCSVMHEALHNHYTQKSL SLSPGK |
| 72 | Fc Chain 1: Ab096.12-H5 HLE | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLLESG GGLVQPGGSLRLSCAASGRTSAHIPMGWFRQAP GKEREFVSAVSWGGTYYADSVKGRFTISRVYAE DNSKNTVYLQMNSLRAEDTAVYYCATRKYATF STENVDYDYWGQGTLVTVSSDKTHTCPPCPAPE LLGGPSVFLFPPKPKDTLMISRTPEVTCVVVDVS HEDPEVKFNWYVDGVEVHNAKTKPREEQYGST YRVVSVLTVLHQDWLNGKEYKCKVSNKALPAP IEKTISKAKGQPREPQVYTLPPSRDELTKNQVSL WCLVKGFYPSDIAVEWESNGQPENNYKTTPPVL DSDGSFFLYSKLTVDKSRWQQGNVFSCSVMHE ALHNHYTQKSLSLSPGK |
| 73 | Fc Chain 1: Ab002-H5 (HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLVESG GGLVQAGGSLRLSCAPSGRTFNPGDLMGWFRQ APGKEREFVAAIKWGPTYYADSVKGRFTISRDY VRNTVYVQMNDLKAEDTAVYYCAGKGSGTFSS NYRDFEYWGQGTQVTVSSDKTHTCPPCPAPELL GGPSVFLFPPKPKDTLMISRTPEVTCVVVDVSHE DPEVKFNWYVDGVEVHNAKTKPREEQYGSTYR VVSVLTVLHQDWLNGKEYKCKVSNKALPAPIE KTISKAKGQPREPQVYTLPPSRDELTKNQVSLW CLVKGFYPSDIAVEWESNGQPENNYKTTPPVLD SDGSFFLYSKLTVDKSRWQQGNVFSCSVMHEA LHNHYTQKSLSLSPGK |
| 74 | Fc Chain 1: Ab007-H5 (HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLVESG GRLAQAGGSLRLSCAASGRAFRPHNVMAWFRQ APEKEREFVAAARWSGIYYAESVKGRFSVSRDY DKNAVFLQMNGLKPEDTAVYYCAVSTAQDMT LALMSDYDYWGQGIQVTVSSDKTHTCPPCPAPE LLGGPSVFLFPPKPKDTLMISRTPEVTCVVVDVS HEDPEVKFNWYVDGVEVHNAKTKPREEQYGST YRVVSVLTVLHQDWLNGKEYKCKVSNKALPAP IEKTISKAKGQPREPQVYTLPPSRDELTKNQVSL WCLVKGFYPSDIAVEWESNGQPENNYKTTPPVL DSDGSFFLYSKLTVDKSRWQQGNVFSCSVMHE ALHNHYTQKSLSLSPGK |
| 75 | Fc Chain 1: Ab052-H5 (HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLVESG GGLVQAGGSLRLSCAASGRTFSPSDLMGWFRQ APGKEREFVAAIKWGPTYYSDSVKGRFTTSRDY VGNTVYLQMNDLKAEDTAVYHCAGKGSSTFSA NYRDYEYWGQGTQVTVSSDKTHTCPPCPAPEL LGGPSVFLFPPKPKDTLMISRTPEVTCVVVDVSH EDPEVKFNWYVDGVEVHNAKTKPREEQYGSTY RVVSVLTVLHQDWLNGKEYKCKVSNKALPAPI EKTISKAKGQPREPQVYTLPPSRDELTKNQVSL WCLVKGFYPSDIAVEWESNGQPENNYKTTPPVL DSDGSFFLYSKLTVDKSRWQQGNVFSCSVMHE ALHNHYTQKSLSLSPGK |

TABLE 1-continued

| SEQ ID NO: | Description | Sequence |
|---|---|---|
| 76 | Fc Chain 1: Ab092-H5 (HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLVESG GGLVQTGGSLRLSCTASGHAFSDLHMGWFRQA PGKEREFVSYINWSGRDSKYADSVKDRFTISRD NAKSTVYLQMNSLKPEDTAVYYCAAEKVYYSI VVSDGSQYDYWGQGTQVTVSSDKTHTCPPCPA PELLGGPSVFLFPPKPKDTLMISRTPEVTCVVVD VSHEDPEVKFNWYVDGVEVHNAKTKPREEQYG STYRVVSVLTVLHQDWLNGKEYKCKVSNKALP APIEKTISKAKGQPREPQVYTLPPSRDELTKNQV SLWCLVKGFYPSDIAVEWESNGQPENNYKTTPP VLDSDGSFFLYSKLTVDKSRWQQGNVFSCSVM HEALHNHYTQKSLSLSPGK |
| 77 | Fc Chain 1: Ab096-H5 (HLE) | AVQLVESGGGLVQPGGSLRLSCAASGFTFSSYA MTWVRQAPGKGPEWVSAIASDGASTSYADSVK GRFTISRDNSKNTLYLQMNSLRPEDTAVYYCAR GGYLTYDRYGQGTLVTVSSGGGGSEVQLVESG GGLVQAGGSLRLSCTASGRTSAHIPMGWFRQAP GKEREFVAAVSWGGTYYADSVKGRFTISRVYA EDNVENTVYLQMNSLKREDTAVYYCATRKYAT FSTENVDYDYWGQGTQVTVSSDKTHTCPPCPAP ELLGGPSVFLFPPKPKDTLMISRTPEVTCVVVDV SHEDPEVKFNWYVDGVEVHNAKTKPREEQYGS TYRVVSVLTVLHQDWLNGKEYKCKVSNKALPA PIEKTISKAKGQPREPQVYTLPPSRDELTKNQVS LWCLVKGFYPSDIAVEWESNGQPENNYKTTPPV LDSDGSFFLYSKLTVDKSRWQQGNVFSCSVMH EALHNHYTQKSLSLSPGK |
| 78 | Second binding domain Ab002-IMGT numbering scheme | EVQLVESGGGLVQAGGSLRLSCAPSGRTFNPGD LMGWFRQAPGKEREFVAAIKWGPTYYADSVKG RFTISRDYVRNTVYVQMNDLKAEDTAVYYCAG KGSGTFSSNYRDFEYWGQGTQVTVSS |
| 79 | Second binding domain Ab002.10-IMGT numbering scheme | EVQLLESGGGLVQPGGSLRLSCAPSGRTFNPGD LMGWFRQAPGKEREFVAAIKWGPTYYADSVKG RFTISRDYSKNTVYLQMNSLRAEDTAVYYCAG KGSGTFSSNYRDFEYWGQGTLVTVSS |
| 80 | Second binding domain Ab002.5nR-IMGT numbering scheme | EVQLLESGGGLVQPGGSLRLSCAPSGRTFNPGD LMGWFRQAPGKEREFVSAIKWGPTYYADSVKG RFTISRDYSRNTLYLQMNSLRAEDTAVYYCAAK GSGTFSSNYRDFEYWGQGTLVTVSS |
| 81 | Second binding domain Ab002.5n-IMGT numbering scheme | EVQLLESGGGLVQPGGSLRLSCAPSGRTFNPGD LMGWFRQAPGKEREFVSAIKWGPTYYADSVKG RFTISRDYSKNTLYLQMNSLRAEDTAVYYCAAK GSGTFSSNYRDFEYWGQGTLVTVSS |
| 82 | Second binding domain Ab002.17nR-IMGT numbering scheme | EVQLLESGGGLVQPGGSLRLSCAPSGRTFNPGD LMGWFRQAPGKGREFVSAIKWGPTYYADSVKG RFTISRDYSRNTVYLQMNSLRAEDTAVYYCAA KGSGTFSSNYRDFEYWGQGTLVTVSS |
| 83 | Second binding domain Ab002.18nR-IMGT numbering scheme | EVQLLESGGGLVQPGGSLRLSCAPSGRTFNPGD LMGWFRQAPGKGLEFVSAIKWGPTYYADSVKG RFTISRDYSRNTVYLQMNSLRAEDTAVYYCAA KGSGTFSSNYRDFEYWGQGTLVTVSS |
| 84 | Second binding domain Ab002.21nR-IMGT numbering scheme | EVQLLESGGGLVQPGGSLRLSCAPSGRTFNPGD LMGWFRQAPGKGREFVSAIKWGPTYYADSVKG RFTISRDYSRNTLYLQMNSLRAEDTAVYYCAAK GSGTFSSNYRDFEYWGQGTLVTVSS |
| 85 | Second binding domain Ab002.21n-IMGT numbering scheme | EVQLLESGGGLVQPGGSLRLSCAPSGRTFNPGD LMGWFRQAPGKGREFVSAIKWGPTYYADSVKG RFTISRDYSKNTLYLQMNSLRAEDTAVYYCAAK GSGTFSSNYRDFEYWGQGTLVTVSS |
| 86 | Second binding domain Ab007-IMGT numbering scheme | EVQLVESGGRLAQAGGSLRLSCAASGRAFRPHN VMAWFRQAPEKEREFVAAARWSGIYYAESVKG RFSVSRDYDKNAVFLQMNGLKPEDTAVYYCAV STAQDMTLALMSDYDYWGQGIQVTVSS |

TABLE 1-continued

| SEQ ID NO: | Description | Sequence |
|---|---|---|
| 87 | Second binding domain Ab007.11-IMGT numbering scheme | EVQLLESGGGLVQPGGSLRLSCAASGRAFRPHN VMAWFRQAPGKEREFVAAARWSGIYYAESVK GRFTISRDYSKNTVYLQMNSLRPEDTAVYYCAV STAQDMTLALMSDYDYWGQGTLVTVSS |
| 88 | Second binding domain Ab052-IMGT numbering scheme | EVQLVESGGGLVQAGGSLRLSCAASGRTFSPSD LMGWFRQAPGKEREFVAAIKWGPTYYSDSVKG RFTTSRDYVGNTVYLQMNDLKAEDTAVYHCA GKGSSTFSANYRDYEYWGQGTQVTVSS |
| 89 | Second binding domain Ab052.9-IMGT numbering scheme | EVQLLESGGGLVQPGGSLRLSCAASGRTFSPSDL MGWFRQAPGKEREFVAAIKWGPTYYSDSVKGR FTISRDYSKNTVYLQMNSLRAEDTAVYYCAGK GSSTFSANYRDYEYWGQGTLVTVSS |
| 90 | Second binding domain Ab0092-IMGT numbering scheme | EVQLVESGGGLVQTGGSLRLSCTASGHAFSDLH MGWFRQAPGKEREFVSYINWSGRDSKYADSVK DRFTISRDNAKSTVYLQMNSLKPEDTAVYYCAA EKVYYSIVVSDGSQYDYWGQGTQVTVSS |
| 91 | Second binding domain Ab0092.6-IMGT numbering scheme | EVQLLESGGGLVQPGGSLRLSCAASGHAFSDLH MGWFRQAPGKGLEFVSYINWSGRDSKYADSVK DRFTISRDNSKNTLYLQMNSLRAEDTAVYYCAA EKVYYSIVVSDGSQYDYWGQGTLVTVSS |
| 92 | Second binding domain Ab0096-IMGT numbering scheme | EVQLVESGGGLVQAGGSLRLSCTASGRTSAHIP MGWFRQAPGKEREFVAAVSWGGTYYADSVKG RFTISRVYAEDNVENTVYLQMNSLKREDTAVY YCATRKYATFSTENVDYDYWGQGTQVTVSS |
| 93 | Second binding domain Ab0096.12-IMGT numbering scheme | EVQLLESGGGLVQPGGSLRLSCAASGRTSAHIP MGWFRQAPGKEREFVSAVSWGGTYYADSVKG RFTISRVYAEDNSKNTVYLQMNSLRAEDTAVY YCATRKYATFSTENVDYDYWGQGTLVTVSS |
| 94 | scFv light chain CDR1 Ab106-IMGT numbering scheme | SSDVGSYNL |
| 95 | scFv light chain CDR1 Ab108-IMGT numbering scheme | SSDVGGYNF |
| 96 | scFv light chain CDR1 Ab114-IMGT numbering scheme | SSNIGNNY |
| 97 | scFv light chain CDR1 Ab116-IMGT numbering scheme | SSNIGAGYA |
| 98 | scFv light chain CDR2 Ab106-IMGT numbering scheme | EVT |
| 99 | scFv light chain CDR2 Ab108-IMGT numbering scheme | DND |
| 100 | scFv light chain CDR2 Ab114-IMGT numbering scheme | DNN |
| 101 | scFv light chain CDR2 Ab116-IMGT numbering scheme | GNS |
| 102 | scFv light chain CDR3 Ab106-IMGT numbering scheme | SSYRNHYTGV |
| 103 | scFv light chain CDR3 Ab108-IMGT numbering scheme | CGTWDGSLSVVVF |

TABLE 1-continued

| SEQ ID NO: | Description | Sequence |
|---|---|---|
| 104 | scFv light chain CDR3 Ab114-IMGT numbering scheme | GTWDSSLSAGWVF |
| 105 | scFv light chain CDR3 Ab116-IMGT numbering scheme | QSYDSSLSEYVF |
| 106 | scFv heavy chain CDR1 Ab106-IMGT numbering scheme | YTFTSYG |
| 107 | scFv heavy chain CDR1 Ab108-IMGT numbering scheme-IMGT numbering scheme | GYTFTSYG |
| 108 | scFv heavy chain CDR1 Ab114-IMGT numbering scheme | GYTFTSYG |
| 109 | scFv heavy chain CDR1 Ab116-IMGT numbering scheme | GYTFTSYY |
| 110 | scFv heavy chain CDR2 Ab106-IMGT numbering scheme | IYPSRGDT |
| 111 | scFv heavy chain CDR2 Ab108-IMGT numbering scheme | ISAYNGNT |
| 112 | scFv heavy chain CDR2 Ab114-IMGT numbering scheme | ISAYNGNT |
| 113 | scFv heavy chain CDR2 Ab116-IMGT numbering scheme | ISAYNGNT |
| 114 | scFv heavy chain CDR3 Ab106-IMGT numbering scheme | AKGGDYGDYLDT |
| 115 | scFv heavy chain CDR3 Ab108-IMGT numbering scheme | ARAMGYSYGLGYW |
| 116 | scFv heavy chain CDR3 Ab114-IMGT numbering scheme | ARAMGYSYGLGYW |
| 117 | scFv heavy chain CDR3 Ab116-IMGT numbering scheme | ARDYSSSSSGFGTDYW |
| 118 | Ab106 scFv-IMGT numbering scheme | QSALTQPASVSGSPGQSITISCTGTSSDVGSYNLV SWYQQVPDKAPKLIIYEVTERPSGISNRFSGSKS GNTASLTISGLQAEDEGDYYCSSYRNHYTGVFG TGTKVTVLSGGGGGSGGGGSGGGRSEVQLVQS GAEVKKPGASVKVSCKASGYTFTSYGISWVRQ APGQGLEWMGGIYPSRGDTNYAQKFQGRVTMT RDTSISTAYMELSRLTSDDTAVYYCAKGGDYG DYLDTWGQGTLVTVSS |
| 119 | Ab108 scFv-IMGT numbering scheme | QSVLTQPASASGSPGQSITISCTGTSSDVGGYNF VSWYQQLPGTAPKLLIYDNDKRPSGISDRFSGSK SGTSATLGITGLQTGDEADYYCGTWDGSLSVVV FGGGTKVTVLSGGGGSGGGGSGGGRSEVQLV QSGAEVKKPGASVKVSCKASGYTFTSYGISWVR QAPGQGLEWMGWISAYNGNTNYAQKLQGRVT MTRDTSTSTAYMELRSLRSEDTAVYYCARAMG YSYGLGYWGQGTMVTVSS |

TABLE 1-continued

| SEQ ID NO: | Description | Sequence |
|---|---|---|
| 120 | Ab114 scFv-IMGT numbering scheme | QSVLTQPPSVSVAPGQKVTISCSGSSSNIGNNYV SWYQQLPGTAPKLLIYDNNKRPSGIPDRFSGSKS GTSATLGITGLQTGDEADYYCGTWDSSLSAGW VFGGGTQLIILSGGGGGSGGGGSGGGRSEVQLV QSGAEVKKPGVSVKVSCKASGYTFTSYGISWVR QAPGQGLEWMGWISAYNGNTNYAQKLQGRVT MTTDTSTSTAYMELSRLRSDDTAVYYCARAMG YSYGLGYWGQGTLVTVSS |
| 121 | Ab116 scFv-IMGT numbering scheme | QSVLTQPPSVSGAPGQRVTISCTGSSSNIGAGYA VHWYQQLPGVAPKLLIYGNSNRPSGVPDRFSGS KSGTSASLGITGLLAEDEADYYCQSYDSSLSEYV FGTGTKVTVLSGGGGGSGGGGSGGGRSQVQLV QSGAEVKKPGASVKVSCKASGYTFTSYYMHWV RQAPGQGLEWMGWISAYNGNTNYAQKLQGRV TMTTDTSTSTAYMELRSLRSDDTAVYYCARDY SSSSSGFGTDYWGQGTLVTVSS |
| 122 | Ab062 | EVQLVESGGDLVQAGGSLRLSCAASGSISSTNT MGWYRQVPGKQREPVASITSGGTTNYDDSVKG RFTISTDNAKKEVYLQMNSLSPEDTAVYYCYLR SSLSWRTYWGQGTQVTVSS |
| 123 | Ab062 CDR1 | GSISSTNT |
| 124 | Ab062 CDR2 | ITSGGTT |
| 125 | Ab062 CDR3 | YLRSSLSWRTY |
| 126 | Ab073 | EVQLVESGGGLVQPGGSLRLSCVASGFTFGTYA MSWVRQAPGKGSEWVSHITSSGGFTYYADSVK GRFTISRDNAKNTLYLQMNSLKPEDTAVYYCAR GHWAFYNITTPEEVRGQGTQVTVSS |
| 127 | Ab073 CDR1 | GFTFGTYA |
| 128 | Ab073 CDR2 | ITSSGGFT |
| 129 | Ab073 CDR3 | ARGHWAFYNITTPEEVR |
| 130 | Ab077 | EVQLVESGGDLVQAGGSLRLSCAASGSISSTITM GWYRQAPGKQREPLASITSGGTTNYDDSVKGRF TISRDNAKKEVYLQMNSLAPEDTAVYYCYLRSS LSWRTYWGQGTQVTVSS |
| 131 | Ab077 CDR1 | GSISSTIT |
| 132 | Ab077 CDR2 | ITSGGTT |
| 133 | Ab077 CDR3 | YLRSSLSWRTY |

EXAMPLES

The present disclosure has been described with respect to representative examples that are to be considered illustrative embodiments that do not limit the scope of the disclosure which is defined solely by the claims. All references to publications, including scientific publications, treatises, textbooks, patent applications and issued patents are hereby incorporated by reference for all purposes.

Example 1: CD1a-Targeted PD-1 ImmTAAIs are Functional In Vitro

Figure 1B:
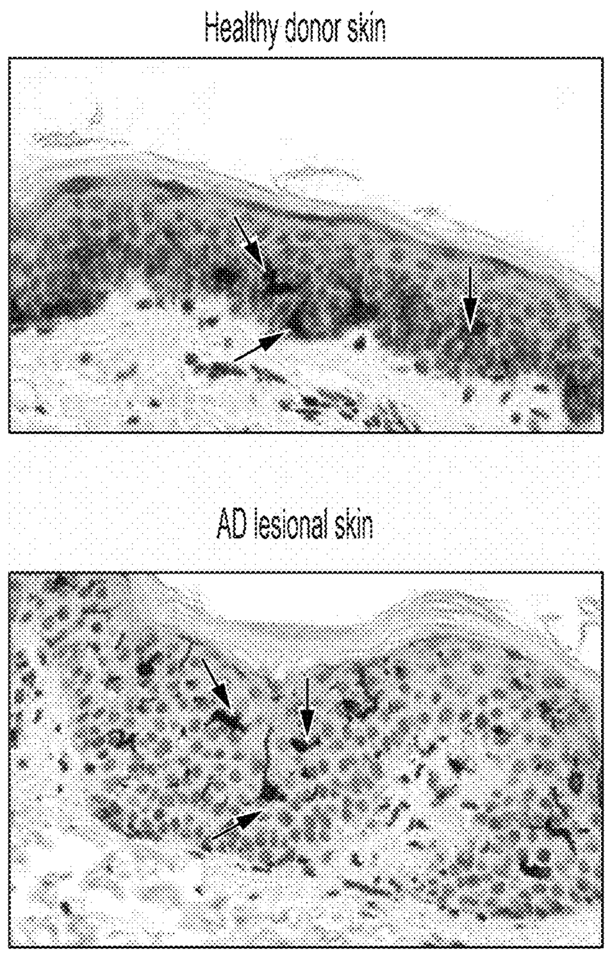
FIG. 1B. Immunohistochemistry (IHC) of CD1a expression on skin APCs in healthy and AD lesional skin using an anti-CD1a antibody (Abcam C1A/711).

Molecules of the present disclosure were designed to simultaneously bind to PD1 and CD1a for use in the treatment of autoimmune diseases. FIG. 1A is a schematic showing the dual modes of action of a CD1a-targeted PD-1 ImmTAAI where one mode of action corresponds to suppression of PD-1+ T cells via PD-1 mediated T cell inhibition, and the second mode of action corresponds to inhibition of CD1a autoreactive T cells via blockade of CD1a. Binding of the molecules to CD1a provided the further benefit that suppression of PD-1+ T cells occurs in a tissue-specific manner as binding to the CD1a target localizes PD-1 agonist activity to the relevant site and cells. The PD-1/CD1a dual targeting approach was further validated by results of immunochemistry studies shown in FIG. 1B demonstrating high levels of CD1a expression on skin APCs in healthy and AD lesional skin. CD1a was undetectable in all other tissues tested using an IHC normal tissue array comprising thirty-five (35) different tissues.

A. Production of Antibodies

Figure 2:
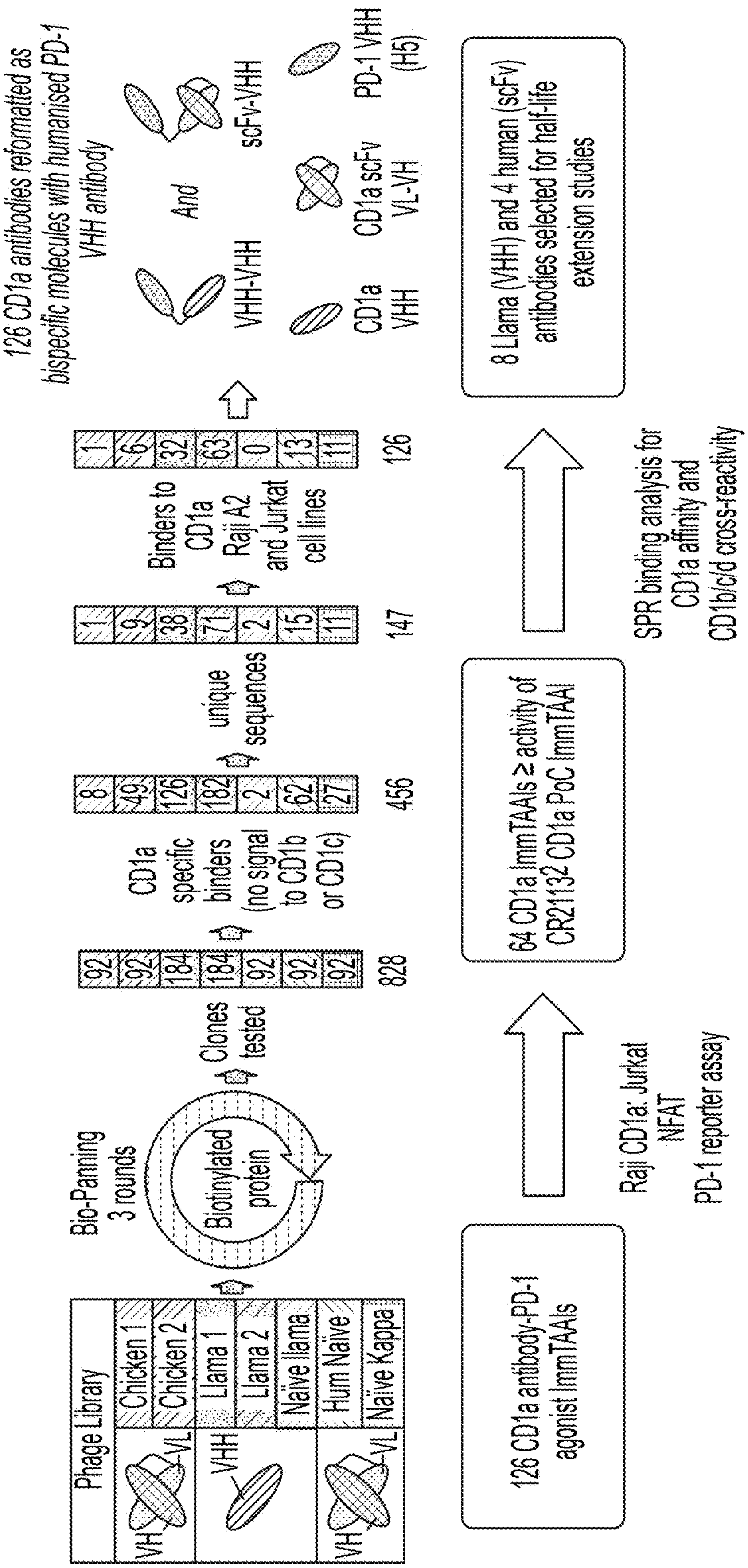
FIG. 2. Schematic showing the process utilized for selection of potential therapeutic CD1a-PD-1 bispecific candidate molecules. The process is further described in Example 1.

Generation and construction of dual action molecules effectively targeting both PD-1 and CD1a involved multiple complex and nuanced steps as described below and set forth in FIG. 2. Phage display libraries derived from multiple sources, including chicken, llama and human were first utilized to select for CD1a antibodies. CD1a-directed antibody libraries were generated by immunization of chickens and llamas with recombinant human CD1a protein. Chicken scFv phage libraries and llama VHH phage libraries were constructed using these CD1a-directed antibody libraries. The CD1a-directed chicken scFv phage libraries, the CD1a-directed llama VHH phage libraries, a naïve llama VHH phage library, a naïve human ScFv library, and a naïve human kappa light chain library were subjected to 3 rounds of panning on immobilized Biotinylated protein (FIG. 2) resulting in selection of over 800 CD1a-specific clones. These clones were further evaluated for specific binding to CD1a, and lack of binding to CD1b or CD1c, resulting in just over 400 clones for subsequent rounds of evaluation. The next round starting with the over 400 clones involved selection of unique sequences followed by further binding analyses to CD1a Raji A2 cells and Jurkat cell lines. This targeted approach resulted in 126 CD1a antibodies, all of which were reformatted as bispecific molecules each comprising a CD1a antibody sequence linked to a humanized PD-1 VHH antibody. Different formats comprising the CD1a antibodies and PD-1 VHH antibody were designed to test the two domains in different orientations and positions relative to one another in the next rounds of selection. The various dual formats (referred to by a "Mol" designation underneath each format) are pictured diagrammatically in FIG. 3.

Once reformatted, these bispecific molecules underwent cell screening for PD-1 agonist function utilizing a Raji CD1a: Jurkat NFAT PD-1 reporter assay. About half of the 126 reformatted bispecific molecules showed greater activity as compared to CR2113, a high-affinity human anti-CD1a monoclonal antibody. Following this, the half of the 126 showing this greater activity were subjected to further biochemical affinity and cross-reactivity assessments. In particular, surface plasmon resonance (SPR) binding analysis was performed to assess CD1a affinity, and cross-reactivity against CD1b, CD1c, and CD1d were conducted. At the end of this process following this rigorous combination of steps and analyses, eight llama VHH (Ab002, Ab007, Ab052, Ab092, Ab062, Ab076, Ab077, and Ab096 with amino acid sequences according to SEQ ID NO: 34-36, 66, 122, 126, 130, and 68, respectively), and four human scFv antibody fragments (Ab106, Ab109, Ab114 and Ab116 with amino acid sequences according to SEQ ID NO: 118-121, respectively) were selected for half-life extension studies described further below. The PD-1 agonist VHH had a $K_D$ value in the range of 50-70 nM and a binding half-life in the range of 15-20 seconds. The sequence of the PD-1 VHH domain is provided in SEQ ID NO: 18 and a humanised variant of the same VHH is provided in SEQ ID NO: 20.

Crystallography was used to map the epitope recognised by the PD-1 agonist VHH. All three CDR loops were shown to mediate contacts to PD-1. Molecular mod-elling showed that the epitope was located away from the membrane proximal region and was adjacent to but did not overlap with the binding site for PD-L.1, in line with Biacore competition measurements. The key residues that the PD-1 agonist VHH (SEQ ID NO: 18 and 20) were identified to bind to are indicated in bold text in the sequence of the extracellular domain of human PD-1 below (SEQ ID NO:13).

B. In Vitro Function—Raji CD1a: Jurkat NFAT PD-1 Reporter Assay

CD1a-PD-1 bispecific agonist ImmTAAIs were tested for CD1a targeting-dependent inhibition of TCR activation in a Raji CD1a: Jurkat NFAT PD-1 reporter assay, where Raji A2 cells were either CD1a-positive or CD1a-negative (FIG. 4 and FIG. 5A-5D).

Raji cells transduced with an HLA-A*02 B2-microglobulin (Raji-A2), with or without lentiviral transduction, were used as APCs.

Figure 5A:
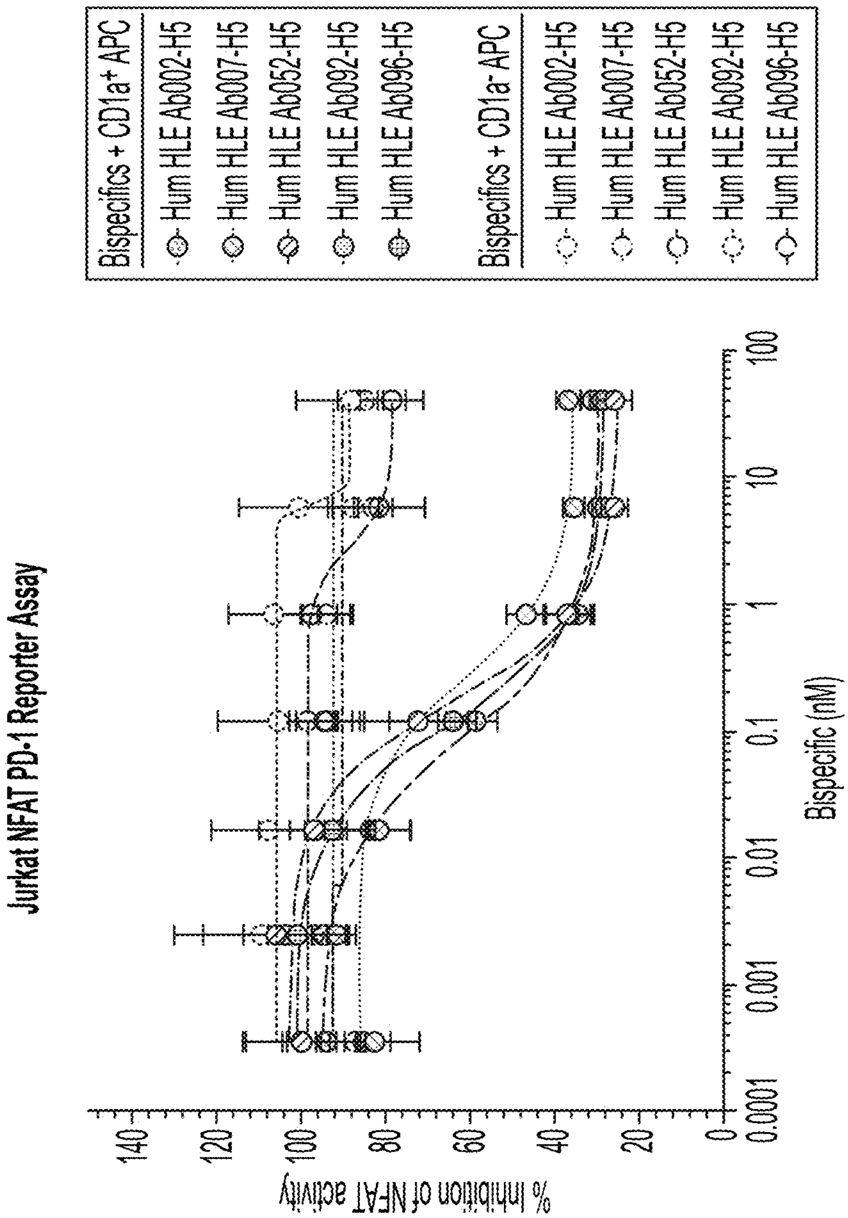
FIG. 5A. Graph showing levels of percent inhibition of NFAT activity as demonstrated by the Jurkat NFAT PD-1 reporter assay (as diagrammed in FIG. 4) using five (5) different humanized half-life extended (HLE) CD1a targeting bispecific molecules (Hum HLE Ab002.10-H5, Hum HLE Ab007.11-H5, Hum HLE Ab052.9-H5, Hum HLE Ab092.6-H5, and Hum HLE Ab096.12-H5), in the presence CD1a-positive (CD1a+) or CD1a-negative (CD1a−) antigen presenting cells (APCs). The bispecific molecules in this figure were obtained after one round of humanization. Each molecule comprises the designated CD1a targeting antibody domain, a half-life extending (HLE) domain, and the PD-1 agonist H5 domain.

Briefly, Jurkat NFAT Mel5 PD-1 CD1a (B2M CRISPR KO) cells, expressing i) a TCR specific for an HLA-A*02 restricted peptide from Melan A (ELAGIGILTV), ii) PD-1, and iii) a luciferase reporter driven by an NFAT-response element were incubated with CD1a-positive Raji-A2 cells and pulsed with a peptide derived from Melan A to trigger TCR signaling and NFAT promoter-mediated luminescence. In the presence of humanized half-life extended variants of CD1a-PD-1 bispecific agonist ImmTAAIs comprising Ab002.10-H5 (SEQ ID NO: 57 and SEQ ID NO: 58), Ab007.11-H5 (SEQ ID NO: 69 and SEQ ID NO: 58), Ab052.9-H5 (SEQ ID NO: 70 and SEQ ID NO: 58), Ab092.6-H5 (SEQ 71 ID NO; and SEQ ID NO: 58) or Ab096.12-H5 (SEQ ID NO: 72 and SEQ ID NO: 58), TCR-stimulated NFAT activation was reduced (FIG. 5A). Control experiments were performed using CD1a-negative Raji-A2 cells.

Raji-A2 APCs (±CD1a expression) were harvested and re-suspended in assay buffer (RPMI 1640 with 1-glutamine, 10% FBS) at $2\times10^6$ cells/ml. Raji cells were pulsed with Melan A peptide for 2 hours at 37° C., 5% $CO_2$ and plated at 50,000 cells/well into white, flat-bottom 96-well assay plates. Assay buffer alone or assay buffer containing titrations of CD1a-PD-1 bispecific agonist ImmTAAIs was added. The assay was initiated by immediately adding 50,000 Jurkat NFL Mel5 PD-1 effector cells and incubating for 16-20 hours at 37° C., 5% $CO_2$. Bioluminescent signal was detected and quantified using Bio-Glo™ Luciferase Assay System (Promega) and a luminometer (CLARIOstar). NFAT activity was normalized against TCR-stimulated controls and dose-response data was analyzed in Prism (GraphPad) using a four-parameter, non-linear least-squares fit to determine IC50 values.

c. Crystallography

Figure 6:
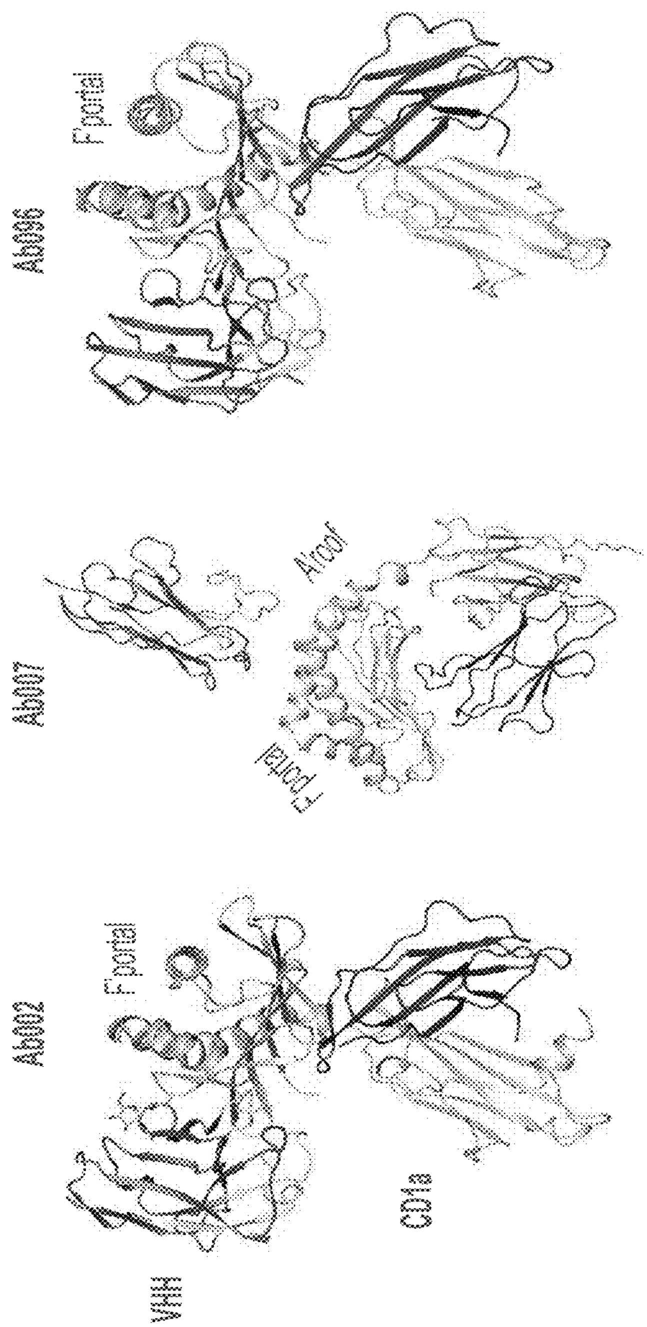

Crystallography was used to map the epitope recognized by CD1a antibodies (FIG. 6). Crystal structures show that Ab002 WT (SEQ ID NO: 24), Ab007 WT (SEQ ID NO: 35) and Ab096 WT (SEQ ID NO: 68) VHH CD1a antibodies bind CD1a epitopes distal to the F' portal, and that binding of these antibodies is unlikely to be influenced by lipids bound to CD1. Ab002 WT and Ab096 WT bind to the side face of CD1a. Ab007 WT has a small footprint on the A' roof. Molecular modeling shows that Ab052 WT (SEQ ID NO: 36) is predicted to bind a similar epitope to that bound by Ab002. Variants of the Ab002 WT, Ab007 WT, and Ab096 WT VHH CD1a antibodies would be predicted to bind in a similar fashion to their wildtype counterparts.

Example 2: Half-Life Extending (Fc) Domain a. Half-Life Extension Selection

Figure 3:
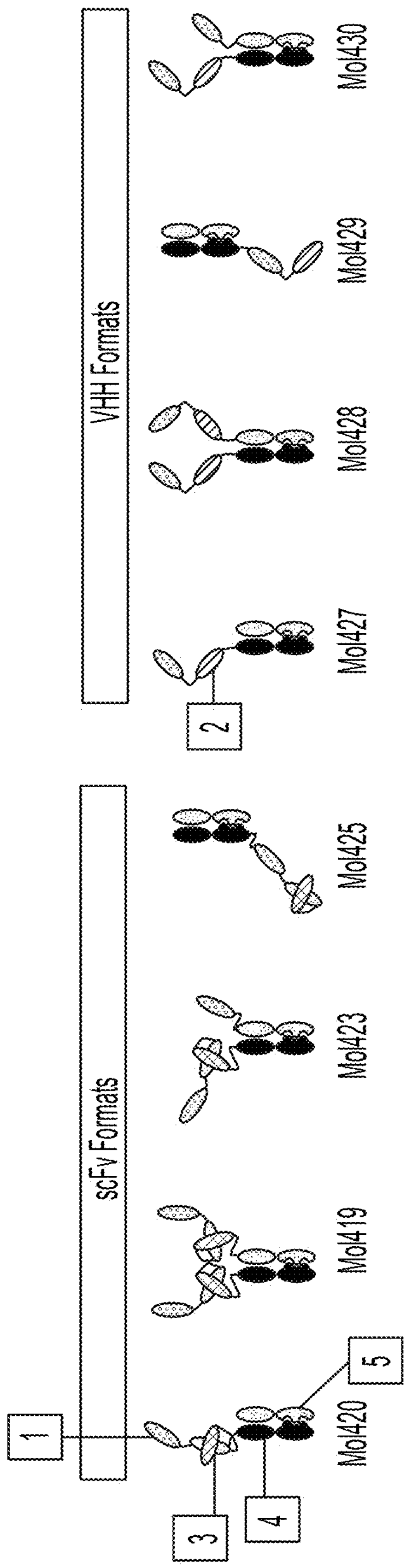
FIG. 3 Schematic of CD1a-PD-1 bispecific formats tested. The domain labeled "1" represents a PD-1 agonist VHH antibody domain (referred to as H5). The domain labeled "2" represents a CD1a VHH antibody domain. The cross-sectional domains labeled "3" represent a CD1a scFv comprising a VH domain and a VL domain. Lines connecting the domains correspond to linker sequences. The domains labeled 4 and 5 represent the FC1 and FC2 domains of an Fc molecule, respectively.

Because autoimmune diseases, including AD, are often chronic conditions requiring sustained treatment, the ability to increase the half-life for therapeutic candidates, and thus have the potential to be dosed less frequently, is particularly important. To extend in vivo half-life of the bispecific molecules, Knob-in-hole Fc (IgG1, truncated hinge N297G comprising SEQ ID NO: 40 was attached to the N- or C-terminus of the CD1a-PD-1 scFv and VHH molecules. FIG. 3 provides a schematic of the resulting half-life-extended (HLE) CD1a-PD-1 bispecific agonist ImmTAAIs.

The in vitro function of the half-life-extended (HLE) CD1a-PD-1 bispecific agonist ImmTAAIs was characterized using the Raji CD1a: Jurkat NFAT PD-1 reporter assay as described above (FIG. 4). The mol427 Fc HLE format (as shown in FIGS. 3, 10A, 11A and 13A) was selected for further studies.

B. Mammalian Expression of HLE-Fusions

Half-life extended (Fc-fusion) bispecific molecules were expressed in ExpiCHO cells using the Thermo ExpiCHO™ transient expression protocol, followed by purification using Protein A chromatography and size exclusion chromatography. Ab002 WT was expressed and purified with an average yield of about 60 mg/L.

Example 3: Binding Characterization of CD1a-PD-1 Bispecific Agonist ImmTAAIs a. Binding Characterization High affinity interactions binding parameters were determined by single cycle kinetics analysis. Five different concentrations of bispecific molecules were injected over a flow cell coated with ~100-200 RU (or 50-100 RU for Biacore 8K instrument) of CD1a complex using a flow rate of 50-60 μl min-1. Typically, 60-120 μl (or approx. 240 μl for Biacore 8K instrument) of bispecific molecule was injected at a top concentration of between 50-100 nM (or 2-50 nM for Biacore 8K instrument), with successive 2-fold dilutions used for the other four injections. The lowest concentration was injected first. To measure the dissociation phase, buffer was injected until ≥10% dissociation occurred, typically after 1-3 hours. Kinetic parameters were calculated using BIAevaluation® software. The dissociation phase was fitted to a single exponential decay equation enabling calculation of half-life. The equilibrium constant kD was calculated from koff/kon. Measurements were performed at 25° C. or 37° C. in Dulbecco's PBS buffer. The relatively greatest retention of PD-1 agonist activity with VHH antibodies was found in mol427 Fc HLE format. Trivalent (mol423/430) and tetravalent formats (mol419/428) were not tolerated. The Ab002.10, Ab007.11 and Ab096.12 CD1a antibodies showed negligible cross-reactivity with CD1b-d expressing or antigen negative cells. A kD value less than 1 nM was observed for the targeting arm (CD1a) with a half-life greater than 30 minutes at 37° C. The ability to bind CD1a was observed in normal and diseased skin, with lipid agnostic binding to CD1a. The ability to block CD1a autoreactive T cell activity in bi-specific format was also observed.

Example 4: Mechanism of Action a. Inhibition of Primary CD4 T Cell Function

Figure 7A:
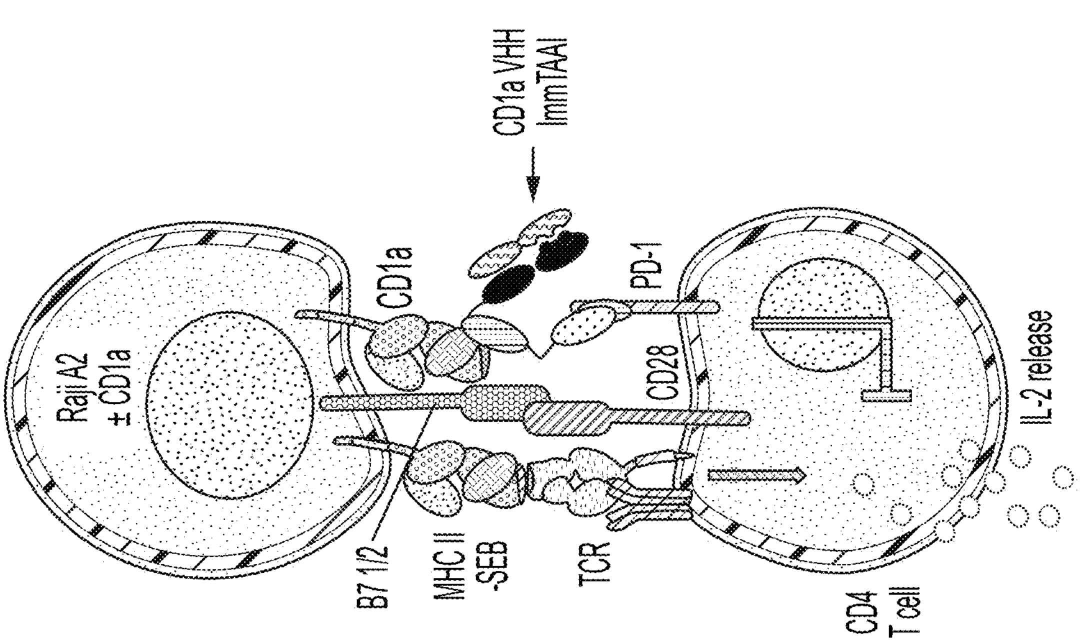
FIG. 7A. Schematic of the Raji SEB human IL-2 cytokine release assay utilized to assess levels of CD4 T cell activation by CD1a-PD1 ImmTAAI molecules.
Figure 7B:
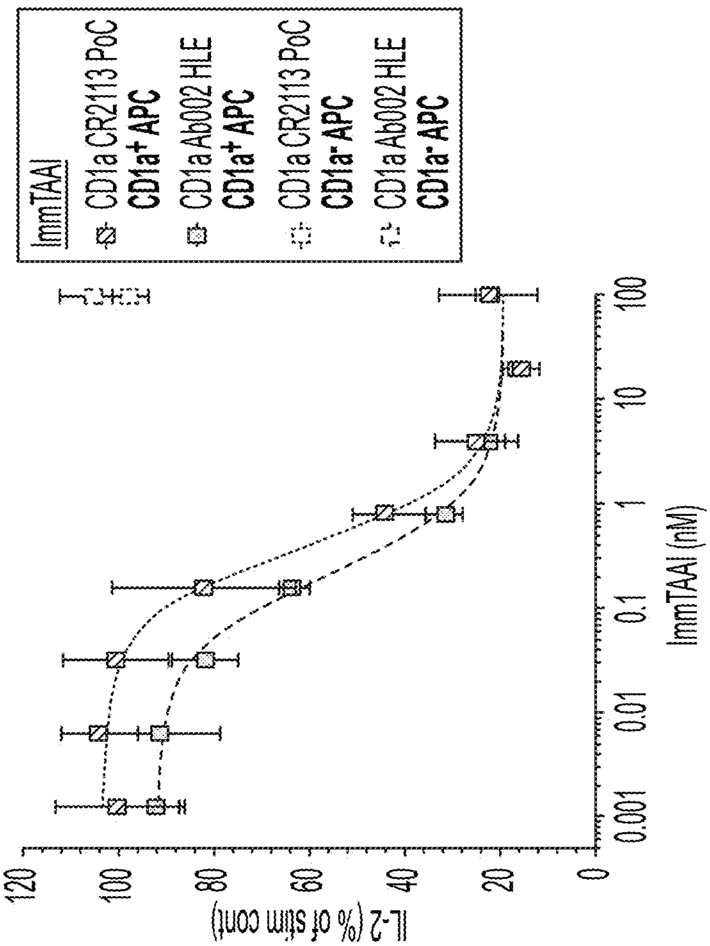
FIG. 7B presents the results of dose response studies of the CD1a wild-type Ab002-H5 HLE construct as compared to CR2113, a CD1a-specific high affinity tool antibody, using the Raji SEB human CD4 T cell IL-2 assay with CD1a+ or CD1a Raji cells (as diagrammed in FIG. 7A).

CD1a-PD-1 bispecific agonist ImmTAAIs as described in Example 1 were tested for CD1a targeting dependent inhibition of Staphylococcal Enterotoxin B (SEB)-stimulated primary human CD4 T cells. FIG. 7A is a schematic representing the assay used to test this inhibition. FIG. 7B presents the results of CD4 T cell activation (represented by the level of IL-2 cytokine released) in dose response studies of a half-life extended version of Ab002.10 (CD1a Ab002.10 HLE) and the tool antibody CR2113 in the Raji SEB human CD4 T cell IL-2 assay using CD1a-positive or CD1a-negative Raji target cells.

Figure 7C:
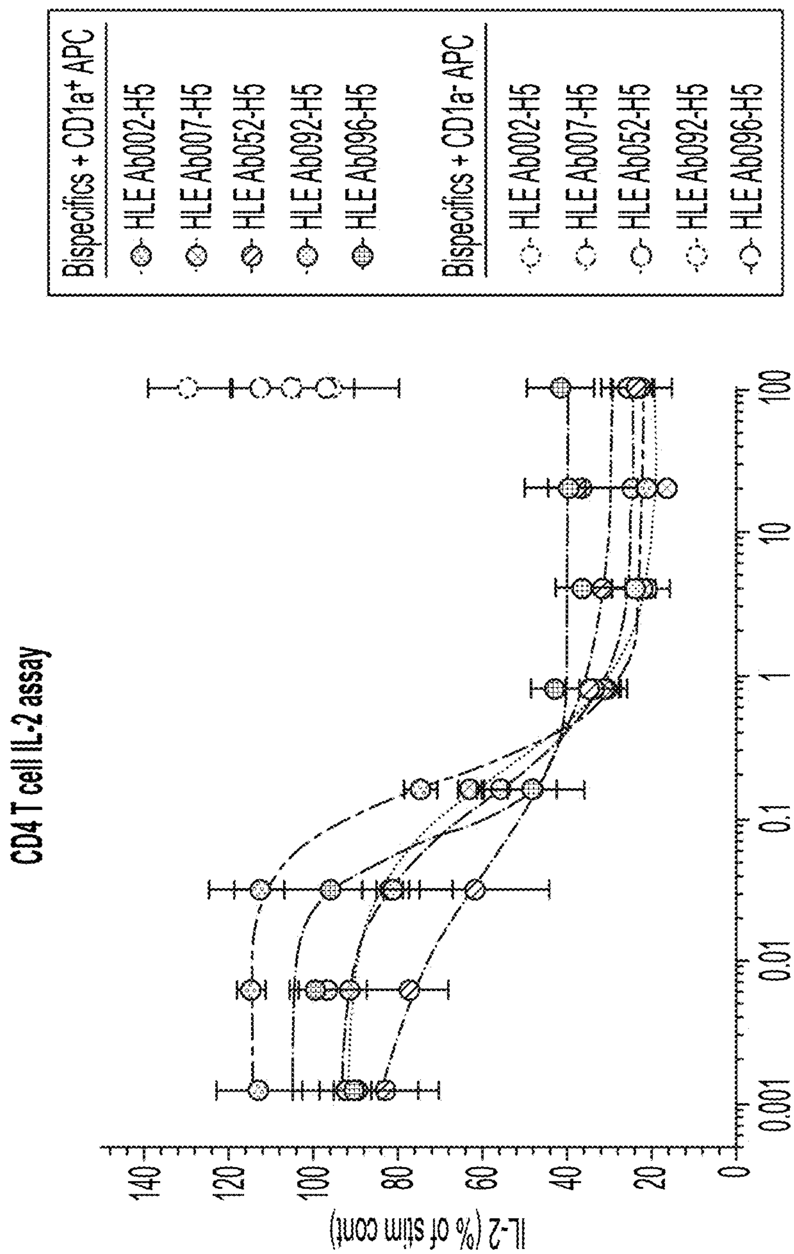
FIG. 7C presents the results of dose response studies of the wild-type PD-1/CD1a HLE constructs Hum HLE Ab007-H5, Hum HLE Ab052-H5, Hum HLE Ab092-H5, and Hum HLE Ab096-H5 using the Raji SEB human CD4 T cell IL-2 assay with CD1a+ or CD1a-Raji cells (as diagrammed in FIG. 7A). Each of the PD-1/CD1a HLE constructs comprise the specified CD1a VHH domain, a half-life extending (HLE) domain, and the PD-1 agonist H5 domain.

Primary human CD4+ T cells were isolated from PBMCs using a CD4 T cell isolation kit (Miltenyi). Raji-A2 cells were used as APCs. T cells were pre-activated by SEB-loaded (Staphylococcal enterotoxin B, Sigma), CD1a-positive Raji-A2 cells to induce PD-1 expression. Pre-activated CD4 PD-1' T cells were subsequently restimulated with SEB-loaded Raji CD1a-positive or Raji CD1a-negative cells in the presence or absence of wild-type CD1a-PD-1 bispecific agonist ImmTAAIs or the CD1a antibody CR2113 (disclosed in U.S. Pat. No. 7,968,092B2). Supernatants were collected after 48 h and IL-2 levels were measured by ELISA (IL2 Ready-SET-Go! ELISA, Invitrogen). IL-2 release was normalized against SEB-stimulated controls and dose response data was analyzed in Prism (GraphPad) using a four-parameter, non-linear, least squares fit to determine IC50 values. As shown in FIG. 7B, Ab002-H5 using CD1a-positive cells showed inhibition of SEB-stimulated primary human CD4 T cells, and showed increased inhibition as compared to CR2113. FIG. 7C shows results in this same assay for HLE versions of Ab002-H5, Ab007-H5, Ab052-H5, Ab092-H5, and Ab096-H5. All of these molecules demonstrated inhibition of SEB-stimulated primary human CD4 T cells with the relative level of inhibition indicated in FIG. 7C.

B. CD1a ImmTAAIs Specifically Bind to CD1a-Positive APCs

Figure 8:
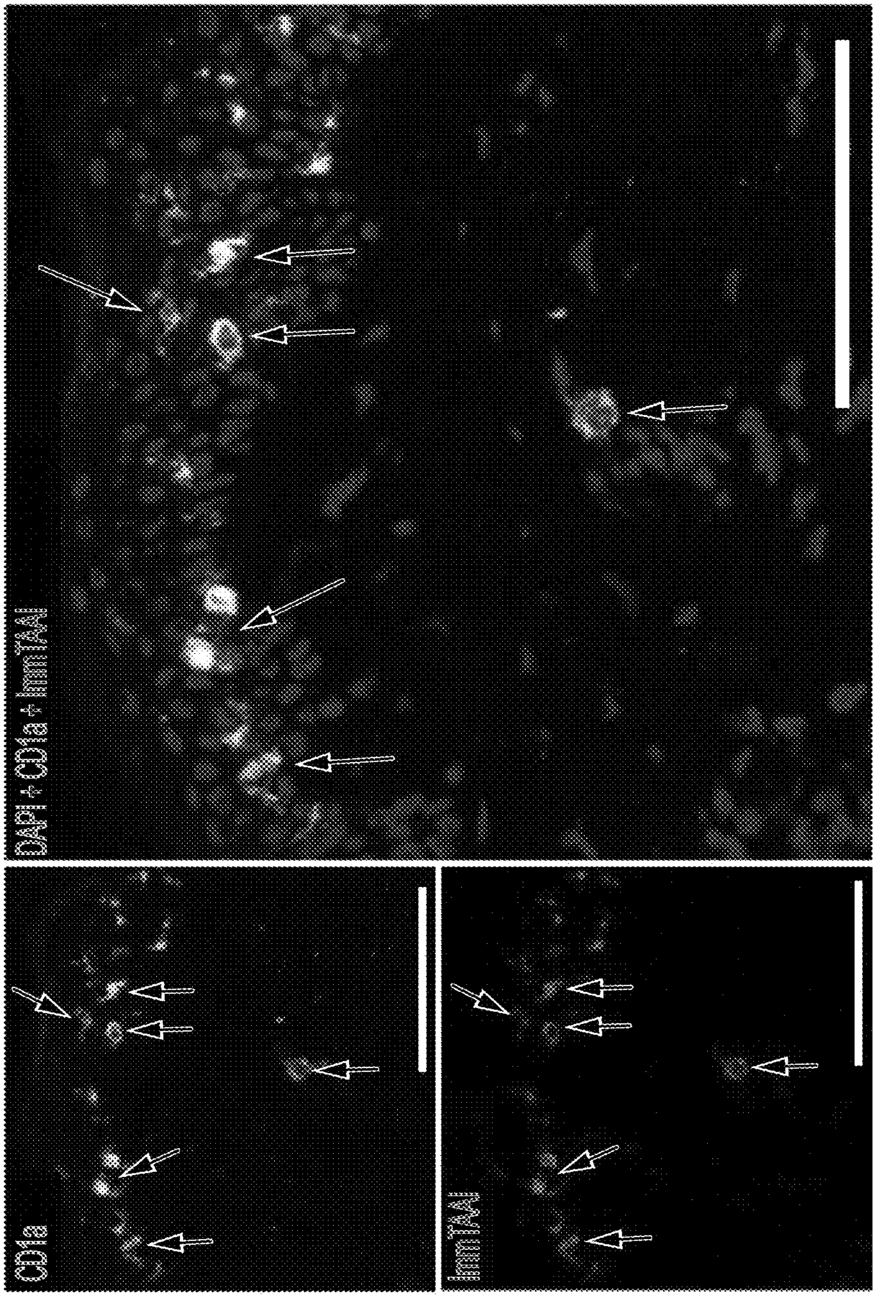
FIG. 8 shows tissue sections stained with a fluorescently labeled HLE Ab002 (anti-CD1a-AF488) and with DAPI indicating that the CD1a ImmTAAI bound specifically to CD1a-positive APCs in human skin cell explants.

Healthy human skin explants were incubated with 200 nM AF647-labelled CD1a ImmTAAI (the HLE version of Ab002: SEQ ID NO: 73 and SEQ ID NO: 58) for 24 h. Skin sections were stained with anti-CD1a-AF488 and DAPI. FIG. 8 shows that the HLE Ab002 CD1a ImmTAAI bound specifically to CD1a-positive APCs in human cell explants.

C. Inhibition of Primary Langerhans Cell-Stimulated T Cell Activation

Figure 9A:
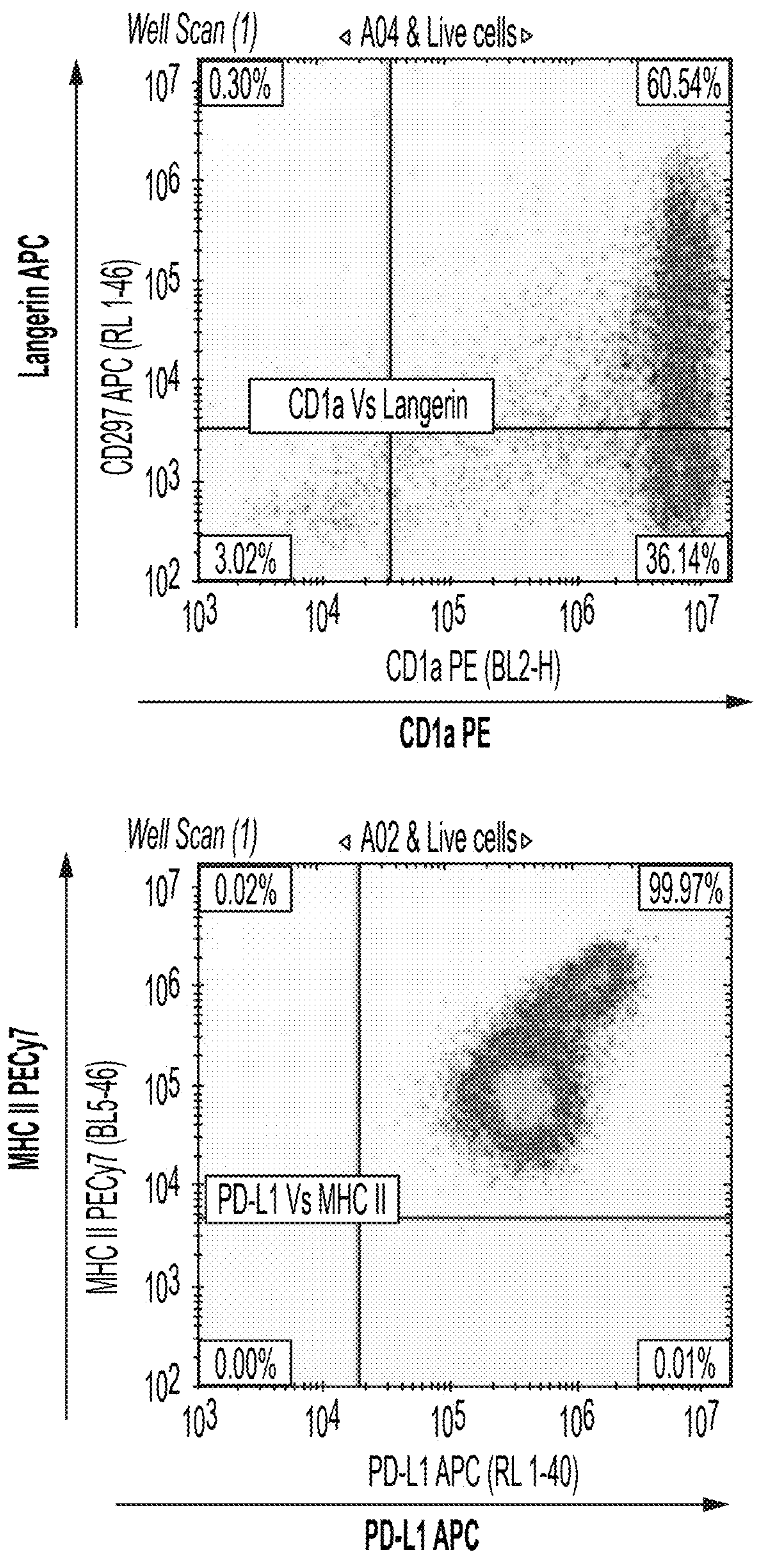
FIG. 9A displays flow cytometry data for the differentiated monocyte-derived Langerhans cells (MoLCs) as described in Example 4.
Figure 9B:
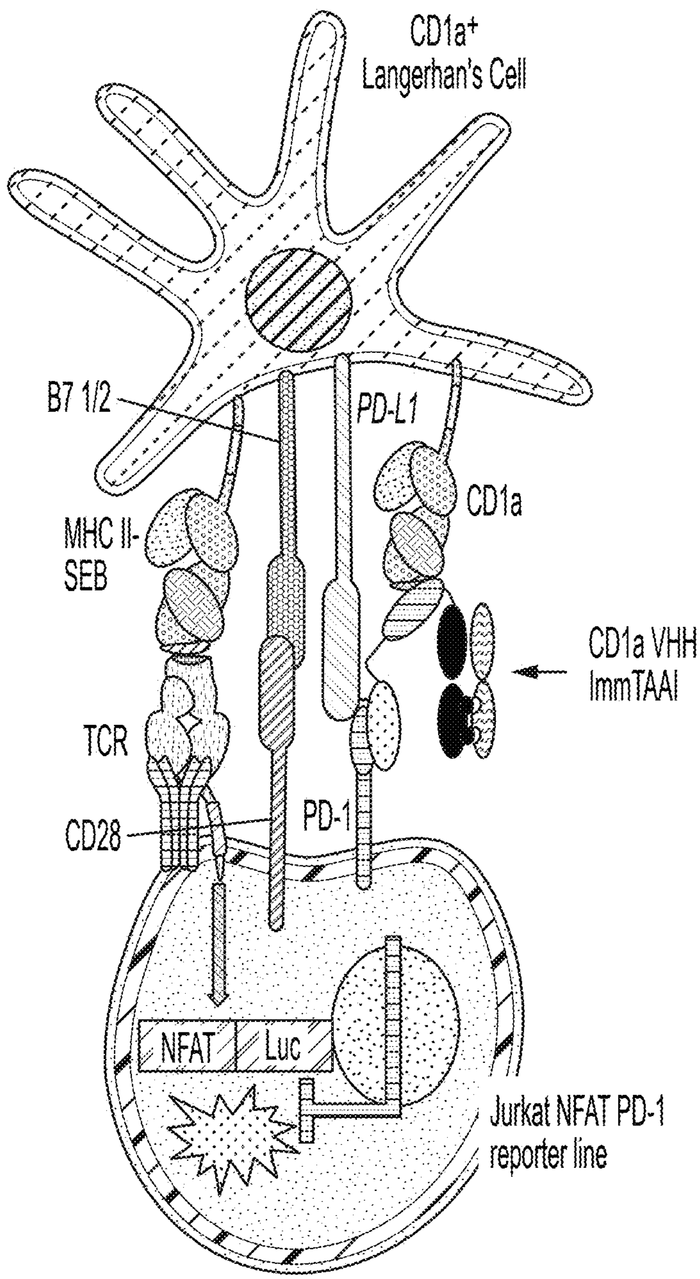
FIG. 9B is a schematic of a Jurkat NFAT PD-1 reporter cell assay with SEB-pulsed MoLCs.
Figure 9C:
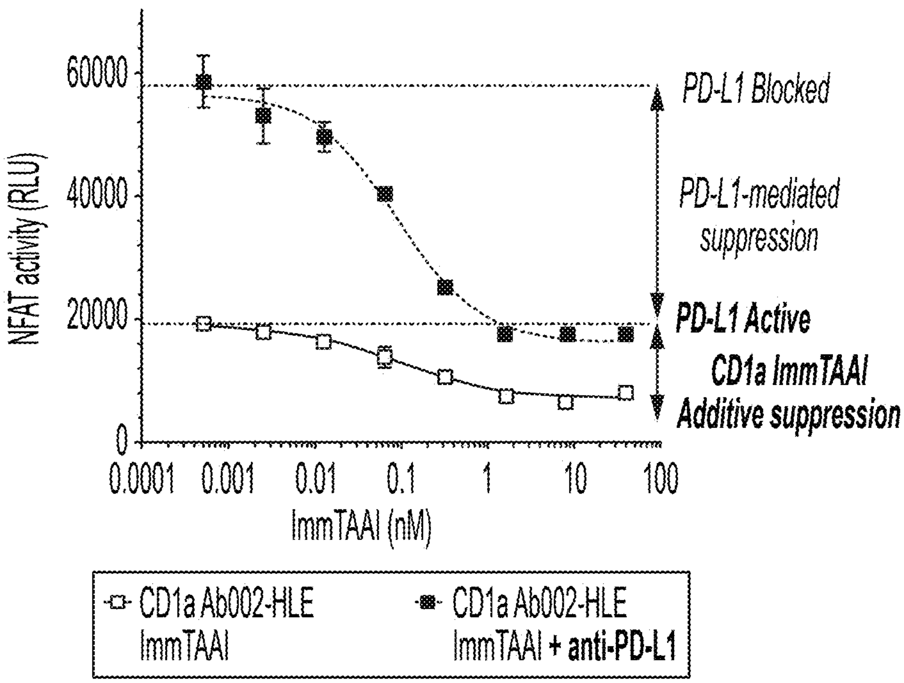
FIG. 9C displays a graph showing levels of percent inhibition of NFAT activity using CD1a-targeted wild-type Ab002-HLE ImmTAAIs, with and without PD-L1 blocking in a model using primary human Langerhans cells (LCs) with endogenous CD1a (FIG. 9B).

CD14− monocytes were differentiated into Langerhans cells (monocyte-derived Langerhan cells or MoLCs) for 6 days using a method adapted from Otsuka et al (J. Immunol, 2018, 201 (10): 3006-3016). Briefly, PBMCs were prepared from fresh blood donations and CD14 monocytes isolated using Miltenyi CD14 beads as per manufacturer's instructions. 500 μl CD14 monocytes at $2\times10^6$ cells/ml were plated into 24-well plates and 500 μl of 2× Langerhans cell (LC) differentiation media (200 ng/ml GM-CSF, 20 ng/ml IL-4, 20 ng/ml TGFβ, 40 ng/ml TNFα, 100 μM 2-ME) made up in R10 media added to 500 μl of cells. LC differentiation media was replaced on days 2 and 5, with IL-4 removed after 48 h. On day 5, LCs were detached, resuspended in LC differentiation media without IL-4 and plated at 20,000 cells/ml into white, flat-bottom 96-well assay plates and incubated for 24 hours at 37° C., 5% $CO_2$. On day 6, assay buffer alone or assay buffer containing titrations of CD1a-PD-1 bispecific agonist ImmTAAIs, in the presence or absence of a PD-L1 blocking antibody, was added. The assay was initiated by immediately adding 50,000 Jurkat NFAT Mel5 PD-1 $CD1a^-$ effector cells and incubating for 16-20 hours at 37° C., 5% $CO_2$. Bioluminescent signal was detected and quantified using Bio-Glo™ Luciferase Assay System (Promega) and a luminometer (CLARIOstar). NFAT activity was normalized against TCR-stimulated controls and dose-response data was analyzed in Prism (GraphPad) using a four-parameter, non-linear least-squares fit to determine IC50 values. Phenotyping of the MoLCs was conducted by flow cytometry. FIG. 9A contains flow cytometry data for the differentiated MoLCs. CD1a ImmTAAI dose-response studies were conducted in an assay where SEB-pulsed MoLCs stimulated Jurkat NFAT PD-1 reporter cells in the presence or absence of PD-L1 blocking antibody. FIG. 9B is a schematic representing the assay utilized for this experiment, and FIG. 9C presents data from the assay for the CD1a Ab002.10-HLE molecule under conditions where PD-L1 was either active or blocked (anti-PD-L1). When PD-L1 activity was blocked, the presence of the bispecific resulted in a dose-dependent suppression of NFAT activity. When PD-L1 was active, NFAT activity was suppressed as compared to PD-L1 being blocked. The presence of the bispecific under the PD-L1 active condition resulted in further additive suppression of NFAT activity in a dose-dependent manner. The results confirmed that CD1a-targeted ImmTAAIs tested, in particular, HLE versions of Ab002 WT, Ab007 WT and Ab096 WT, are active in a model that uses primary human LCs with endogenous CD1a.

d. Blockade of Primary CD1a Autoreactive T Cells

Figure 10A:
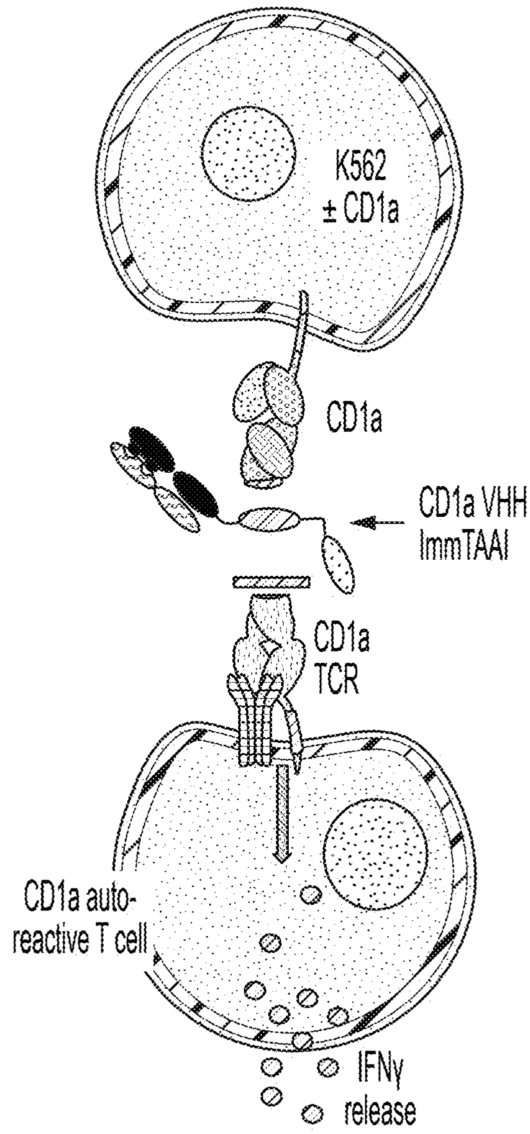
FIG. 10A is a schematic of an assay used to assess blockade of primary CD1a autoreactive T cells.
Figure 10B:
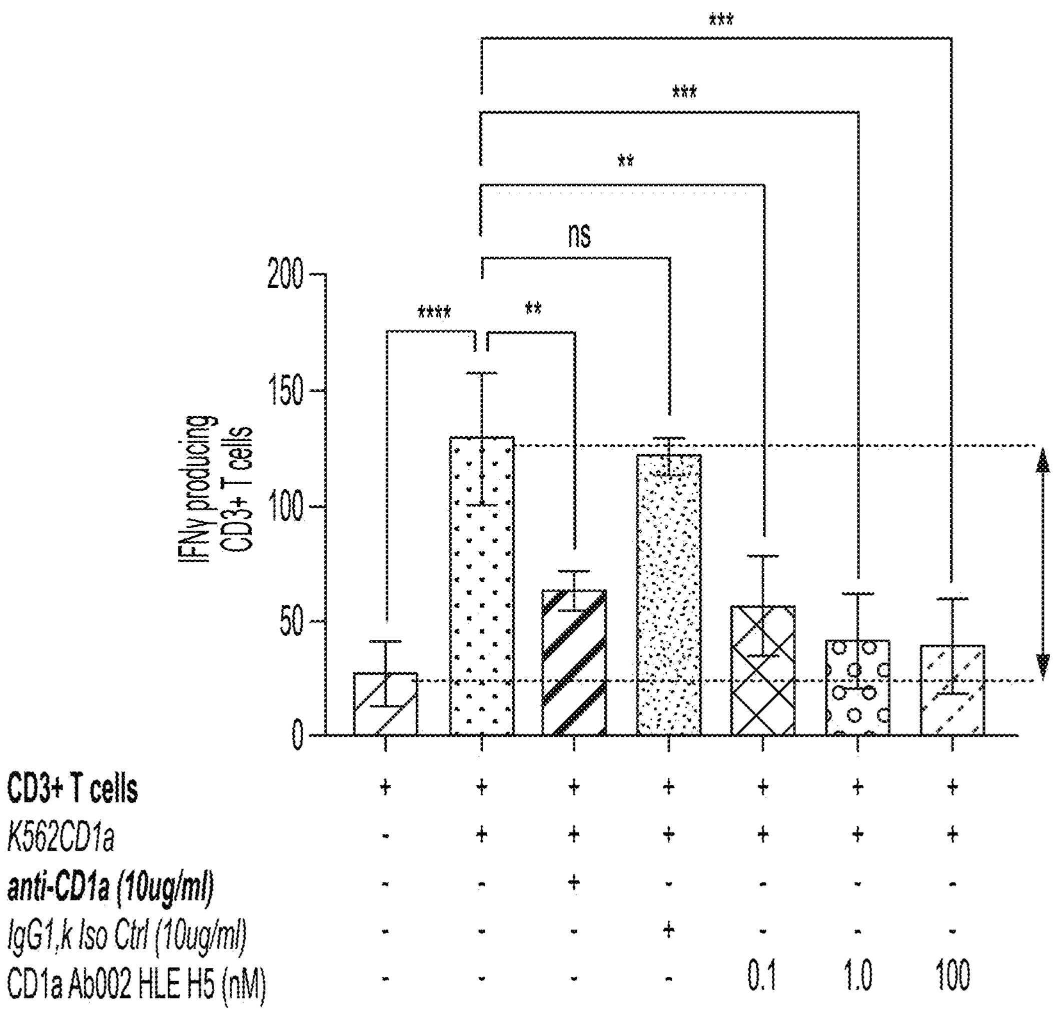
FIG. 10B shows a bar graph indicating the level of IFNγ-producing CD3+ T cell stimulation with CD3+ T cells alone (first bar from left), CD3+ T cells in the presence of CD1a+K562 cells (second bar from left), or further adding to CD3+ T cells and K562 cells an anti-CD1a antibody (third bar from left), or increasing doses of the CD1a/PD-1 bispecific Ab002.10-H5 HLE (fifth, six and seventh bars from left). The negative control (CD3+ T cells and K562 cells, further adding IgG1 isotype control) is shown as the fourth bar from left.

CD1a+ K562 cells were used to stimulate primary PBMC-derived CD1a autoreactive T cells. FIG. 10A is a schematic showing the biological mechanism for how CD1a+ K562 cells can be utilized to demonstrate blockade of primary CD1a autoreactive T cells. Briefly, polyclonal CD3+ T cells were isolated from frozen PBMCs from healthy volunteers and maintained in complete RPMI (1640 RPMI, 10% FBS, P/S, L-Glu) and 200 U/ml of IL-2 (Proteintech). After 48 hours, IL-2 was removed from the media and T cells rested overnight in complete RPMI. K562 cells lentivirally transduced with CD1a presenting undefined endogenous lipid antigen were used to stimulate polyclonal CD3+ T cells in an overnight culture at a 1:2 ratio of K562CD1a and T cells, respectively, in the presence or absence of CD1a-PD-1 bispecific agonist ImmTAAIs or a commercially available CD1a-blocking antibody (clone HI149). IFNγ-release was detected using IFNγ-ELISpot (BD Biosciences) and ELISpot plates scanned and IFNγ-release quantified on ImmunoSpot plate reader and software. FIG. 10B shows IFNγ producing CD3+ T cell stimulation in the absence of CD1a K562 cells (first bar from left). When CD1a+K562 cells are added, T cell stimulation is increased (second bar from left). This stimulation can be abrogated in the presence of an anti-CD1a antibody (third bar from the left), but not a negative control (fourth bar from left). This stimulation is also abrogated in a dose-dependent manner in the presence of the CD1a Ab002 WT HLE H5 molecule (fourth, fifth and sixth graphs from left).

Figure 11A:
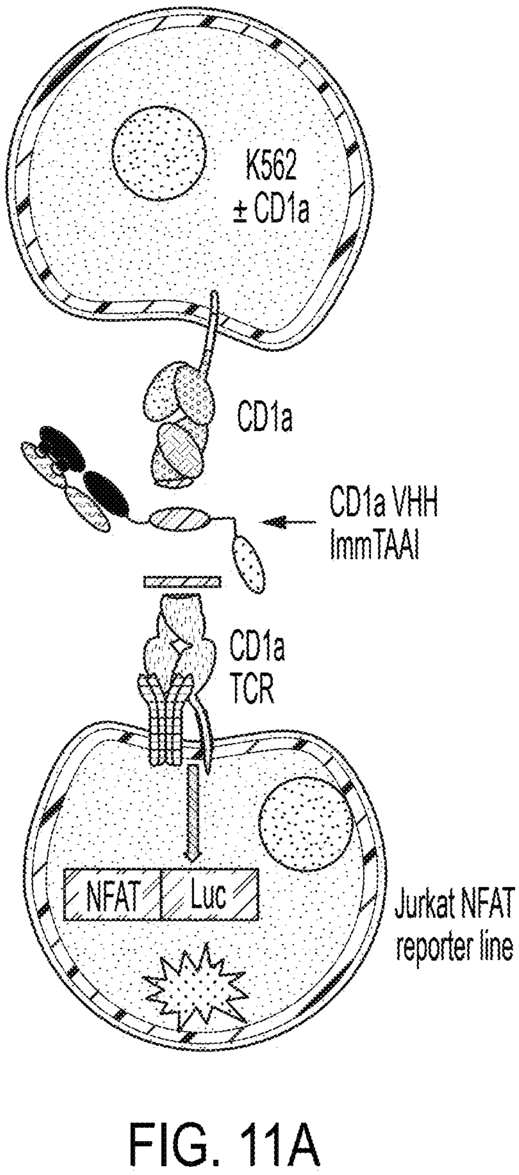
FIG. 11A is a schematic of an assay used to assess ImmTAAI-dose dependent blockade of CD1a TCR reporter.
Figure 11B:
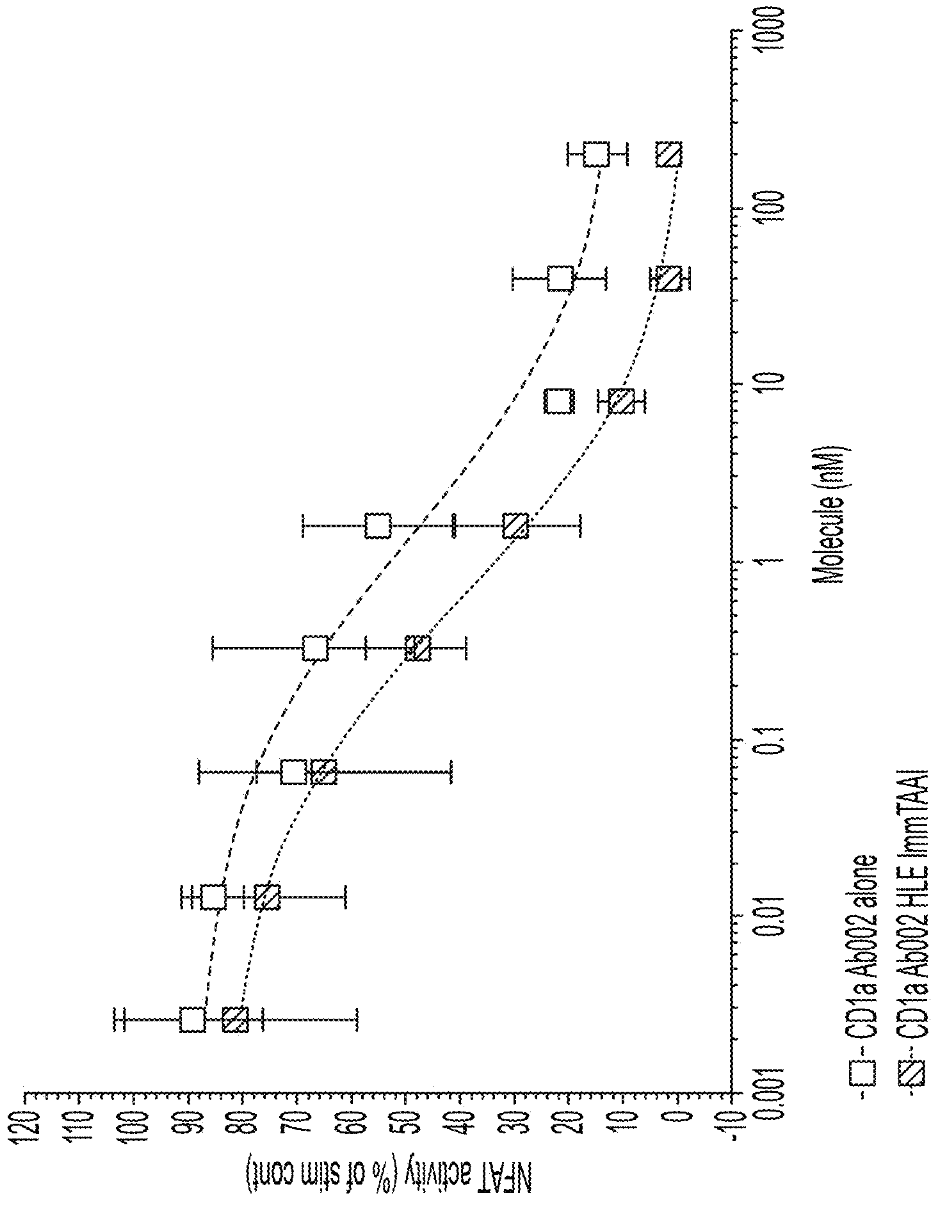
FIG. 11B and FIG. 11C presents NFAT activity from the CD1a TCR Jurkat NFAT reporter assay as diagrammed in FIG. 11A in the presence of the CD1a/PD-1 bispecific molecule Ab002.10-H5 or the half-life extended (HLE) version of Ab002.10-H5 (FIG. 11B), or in the presence of the HLE CD1a/PD-1 bispecific molecules indicated as compared to an anti-CD1a clone (H149) and an IgG1 isotype control (FIG. 11C).
Figure 11C:
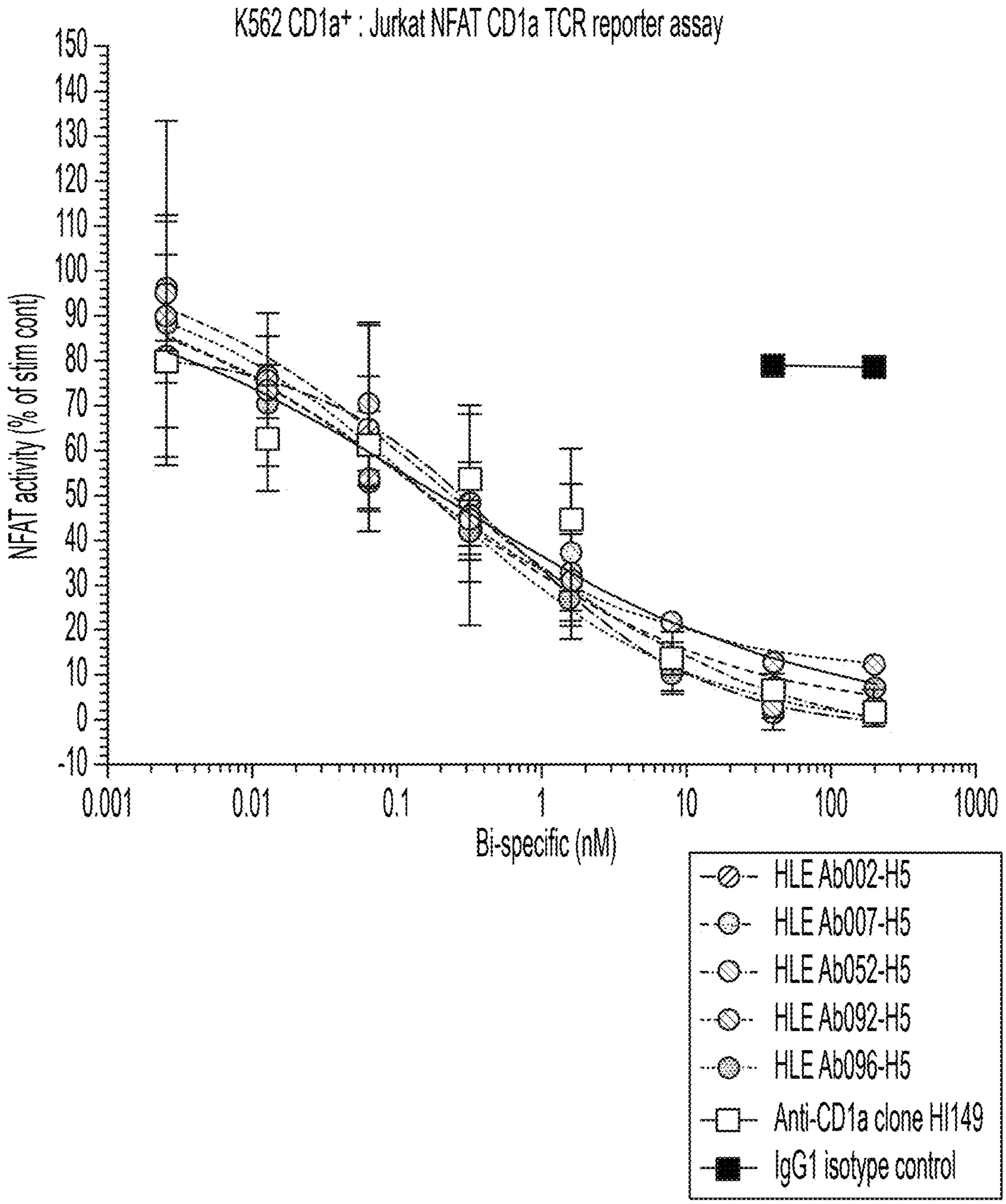

FIG. 11A is a schematic drawing showing the biological mechanism for how the assay assesses blockade of a CD1a TCR reporter construct. FIG. 11C presents NFAT activity from CD1a TCR Jurkat NFAT reporter cells. A CD1a-specific TCR was expressed in a TCR knockout Jurkat NFAT reporter line. K562 cells lentivirally transduced with CD1a were used to stimulate the Jurkat CD1a TCR NFAT reporter cell line in the presence or absence of HLE CD1a-PD-1 bispecific agonist ImmTAAIs (HLE-Ab002 WT-H5, HLE Ab007 WT-H5, HLE Ab052 WT-H5, HLE Ab092 WT-H5, or HLE Ab096 WT-H5), or a commercially available CD1a-blocking antibody (clone HI149). The Jurkat CD1a NFAT reporter cell line does not express PD-1 and allows interrogation of the CD1a TCR blockade. Bioluminescent signal was detected and quantified using Bio-Glo™ Luciferase Assay System (Promega) and a luminometer (CLARIOstar), as described above. NFAT activity was normalized against TCR-stimulated controls and dose-response data was analyzed in Prism (GraphPad) using a four-parameter, non-linear least-squares fit to determine IC50 values.

Example 5: Humanization of HLE CD1a-PD1 ImmTAAIs

Figures 12A, 12B:
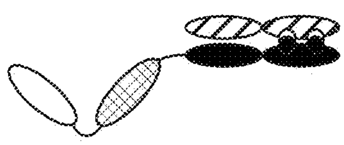
FIG. 12A. Schematic of mol427 bispecific ImmTAAI format.
FIG. 12B. Results of stability studies of Ab002.10, Ab007.11 and Ab052.9.

As described above in Example 2a, several of the selected CD1a-PD1 ImmTAAIs designed to be in the mol427 format (as depicted in FIG. 12A) were further humanized. The strategy for humanization that was undertaken included (1) grafting human framework (FW) (H' V3-23*01), (2) evaluating llama residues for stability, structure and CDR conformation, (3) designing a panel of back mutants, (4) checking expression, stability and binding of the humanized versions of the construct, and (5) refining humanization-single point mutations to identify key llama residues on selected clones. The stability and binding of humanized and half-life extended variants of Ab002.10, Ab007.11, Ab052.9, and Ab096.12 is shown in FIG. 12B.

Additional engineering of the molecules was performed to further humanize the selected ImmTAAI molecules. Ab002.10.18nR and Ab002.10.21nR each comprise a VHH CD1 domain humanized to about 94%, e.g., 94±1-2%. The further humanization of these molecules, such as Ab002.10, was performed to provide a more optimal molecule for the purposes of both manufacturing and for therapeutic treatment. The re-engineered Ab002.10.18nR molecule demonstrated a kD at 37° C. of about 1 nM (in the range of 904 pM to 1.50 nM), preserving the affinity of the previous optimized variant and the advantageous features of the HLE domain while also including additional humanization to minimize potential side effects for use in treatment. The Ab002.10.18nR and Ab002.10.21.nR variants demonstrated CD1a-targeting dependent inhibition using the Raji CD1a Jurkat reporter assay (as described above and shown in FIG. 4 and FIG. 5A-5D), dose- and targeting-dependent inhibition of primary CD4 T cell function using the Raji A2 CD1a SEB CD4 T cell IL-2 assay (as described above and shown in FIG. 7A-7D), activity in a model using human MoLCs with endogenous CD1a using a primary LC-stimulated T cell activation assay (as described above and shown in FIG. 9B), as well as blockade of primary CD1a TCR activity with picomolar potency (as described above and shown in FIG. 10A). Results from these assays are presented below:

TABLE 2

Figure 4:
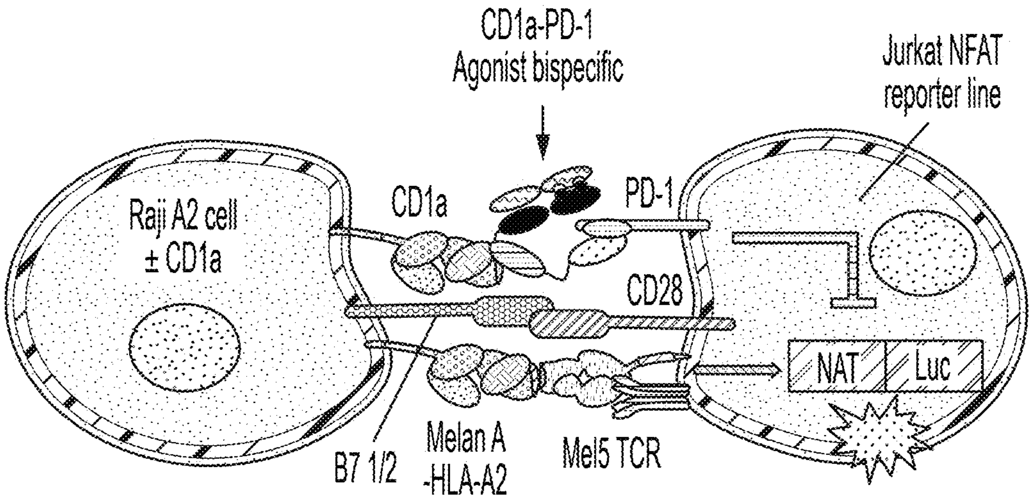
FIG. 4. Schematic of the Raji CD1a: Jurkat NFAT PD-1 reporter assay utilized to assess percent CD1a targeting-dependent inhibition of NFAT activity by CD1a-PD1 ImmTAAI molecules. Inhibition of NFAT activity is an indicator of inhibition of TCR activation.
Figure 5B:
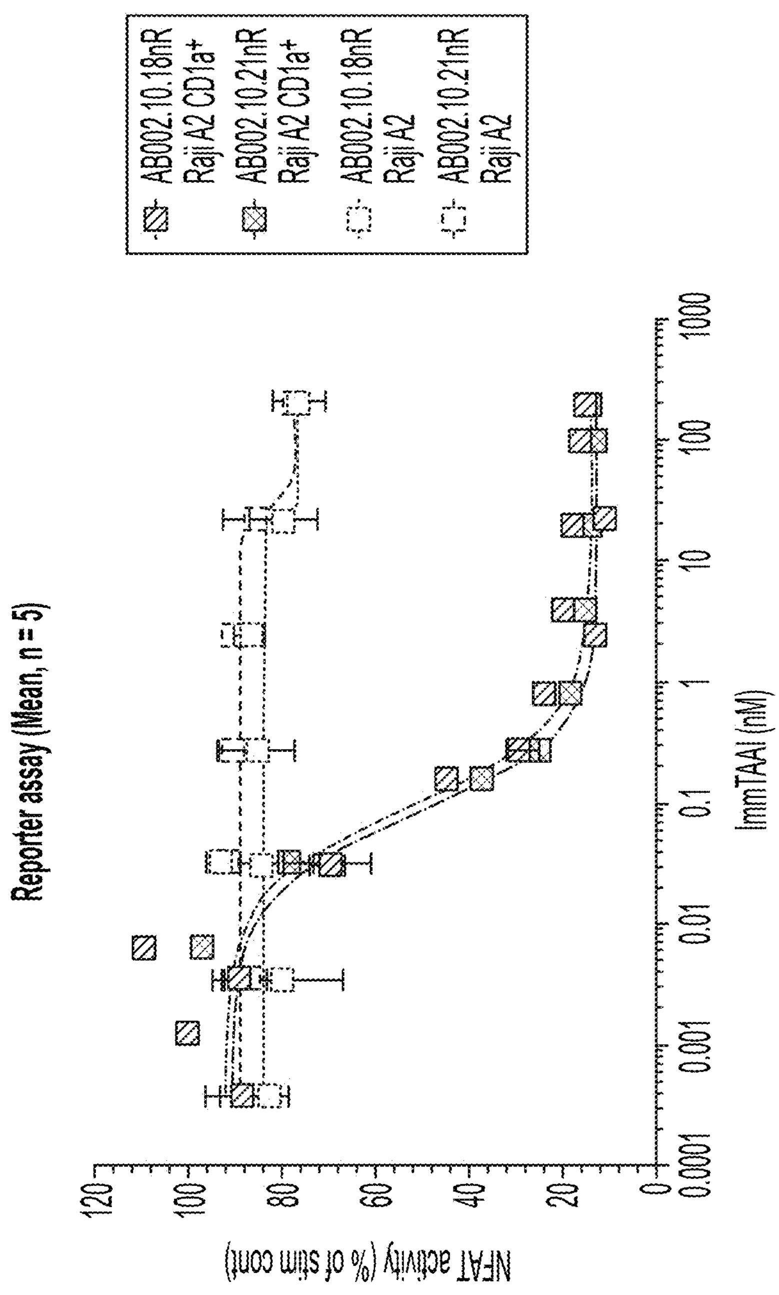
FIG. 5B. Graph showing levels of percent inhibition of NFAT activity as demonstrated by the Jurkat NFAT PD-1 reporter assay (as diagrammed in FIG. 4) using humanized half-life extended (HLE) CD1a targeting bispecific molecules (Ab002.10.18nR-H5 and Ab002.10.21nR-H5), in the presence CD1a-positive (CD1a+) or CD1a-negative antigen presenting cells (APCs).
Figure 5C:
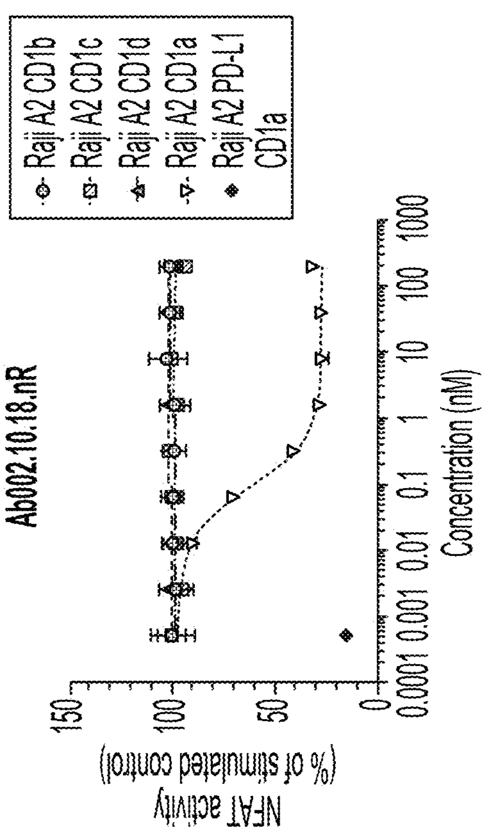
FIG. 5C and FIG. 5D. Graphs showing levels of percent inhibition of NFAT activity as demonstrated by the Jurkat NFAT PD-1 reporter assay (as diagrammed in FIG. 4) using humanized half-life extended (HLE) CD1a targeting bispecific molecules Ab002.10.18nR-H5 (FIG. 5C) and Ab002.10.21nR-H5 (FIG. 5D) in the presence or absence of CD1a/b/c/d in the Raji A2 cells.
Figure 5D:
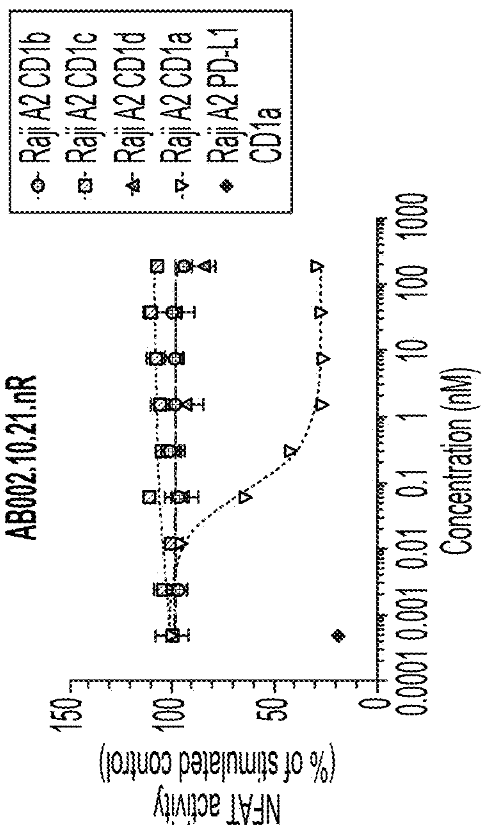

Raji CD1a: Jurkat Report Assay (assay schema: FIG. 4; results: FIG. 5B)

| Molecule | % Max. Inhibition | IC50 (pM) |
|---|---|---|
| AB002.10.18nR | 85.85 | 92.25 |
| AB002.10.21nR | 87.08 | 77.91 |

TABLE 3

Figure 7D:
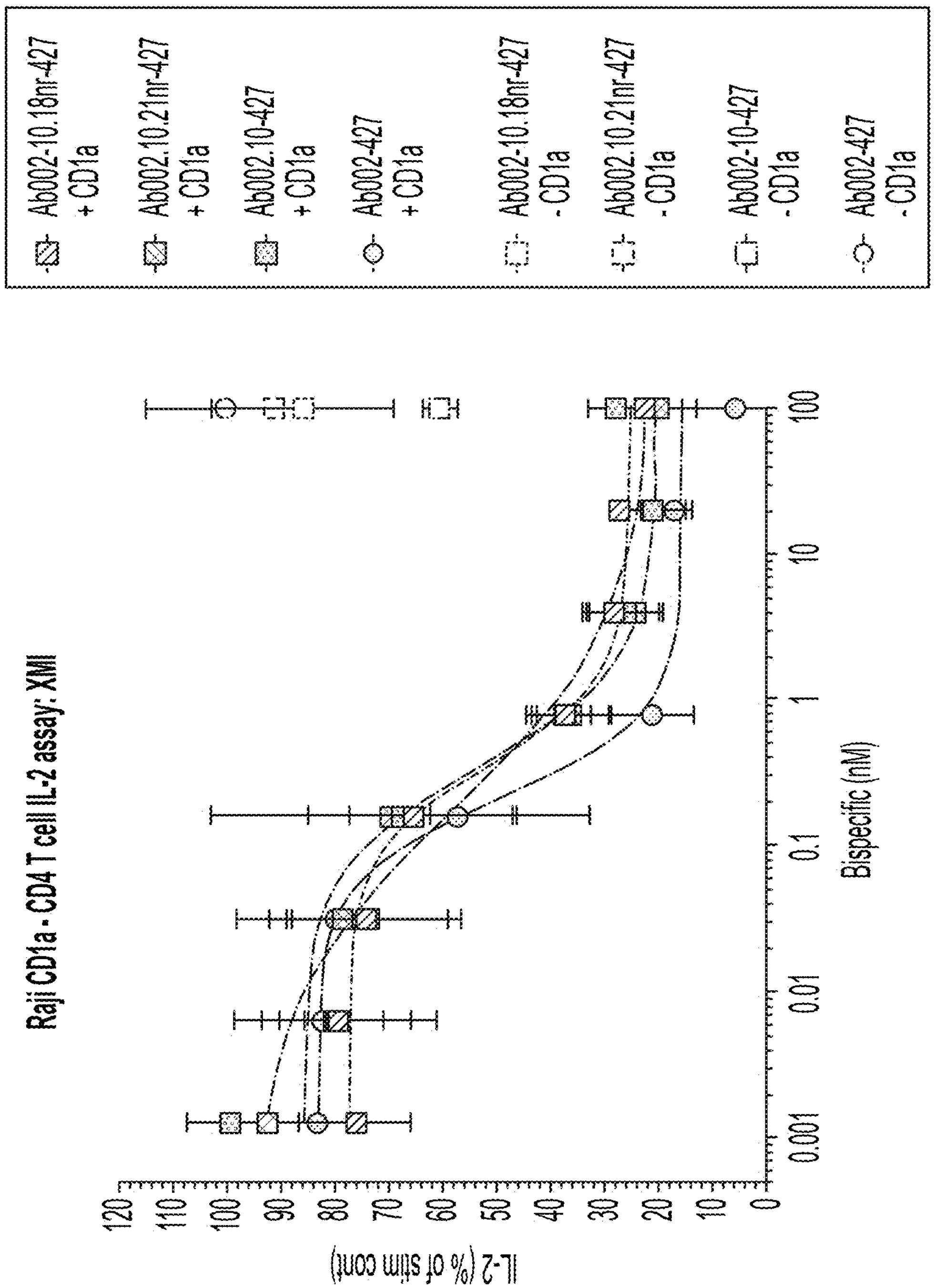
FIG. 7D presents the results of dose response studies, as diagrammed in FIG. 7A, of the variant PD-1/CD1a HLE constructs Ab002-10.18nr-H5, Ab002.10.21nr-H5, and Ab002.10-H5, and the wild-type PD-1/CD1a HLE construct Ab002-H5, using the Raji SEB human CD4 T cell IL-2 assay with CD1a+ or CD1a-Raji cells. Each of the PD-1/CD1a HLE constructs comprise the specified CD1a VHH domain, a half-life extending (HLE) domain, and the PD-1 agonist H5 domain.

| Raji A2 CD1a SEB: CD4 T cell IL-2 Assay (assay schema FIG. 7A; results: FIG. 7D) | | | | | | | | | | | | | |
|---|---|---|---|---|---|---|---|---|---|---|---|---|---|
| | Donor VFI | | | Donor WEI | | | Donor XMI | | | | | | |
| | Raji A2 CD1a (targeted) | | Raji A2 (non-targeted) | Raji A2 CD1a (targeted) | | Raji A2 (non-targeted) | Raji A2 CD1a (targeted) | | Raji A2 (non-targeted) | Collated Data | | | |
| | | | | | | | | | | IC50 (pM) | | Max Inhib (%) | |
| ImmTAAI | IC50 (pM) | Maximal Inhibition (%) | Maximal Inhibition (%) | IC50 (pM) | Maximal Inhibition (%) | Maximal Inhibition (%) | IC50 (pM) | Maximal Inhibition (%) | Maximal Inhibition (%) | Mean | SD | Mean | SD |
| AB002.10.18nR | 179 | 78 | −10 | 143 | 73 | 3 | 361 | 77 | 14 | 227.6 | 117.0 | 75.9 | 2.7 |
| AB002.10.21nR | 124 | 82 | −18 | 162 | 79 | −8 | 349 | 77 | 6 | 211.4 | 120.3 | 79.2 | 2.4 |
| AB002.10 | 174 | 78 | −5 | 94 | 74 | −9 | 175 | 72 | 37 | 147.5 | 46.4 | 74.5 | 3.0 |
| AB002 | Poor data | 78 | −6 | 78 | 79 | −20 | 214 | 82 | −1 | 145.9 | 96.6 | 80.1 | 2.2 |

TABLE 4

Figure 9D:
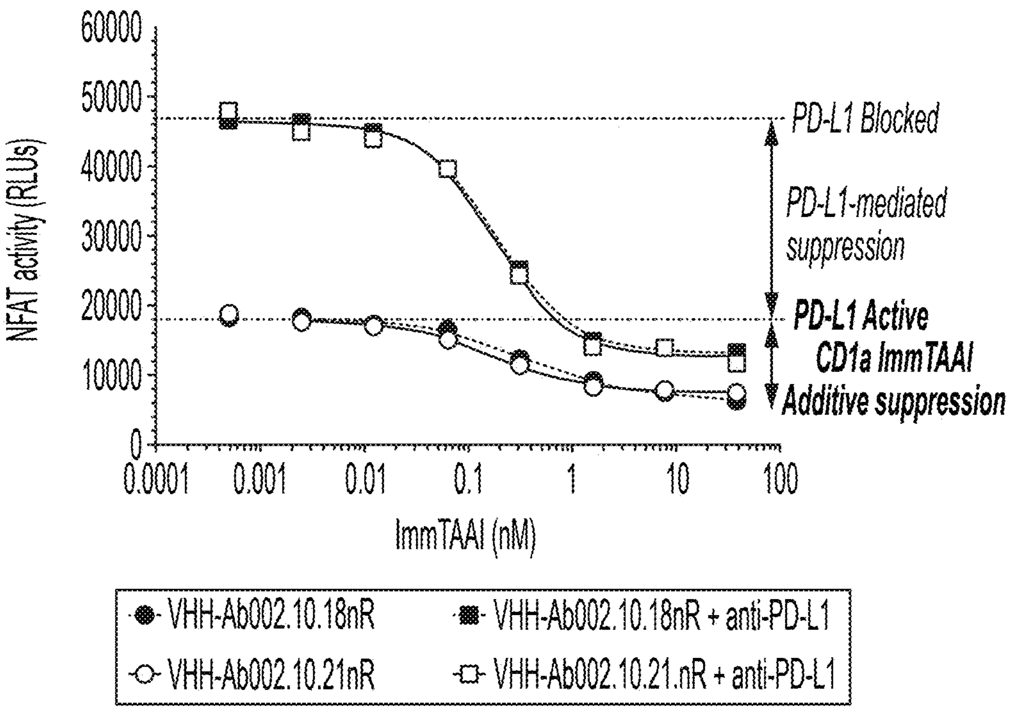
FIG. 9D displays a graph showing levels of percent inhibition of NFAT activity using CD1a-targeted variant Ab002.10.18nR VHH and Ab002.10.21nR VHH constructs, with and without PD-L1 blocking in a model using primary human Langerhans cells (LCs) with endogenous CD1a (FIG. 9B).

| Jurkat NFAT PD-1 Report Assay (assay schema FIG. 9B; results: FIG. 9D) | | | | | |
|---|---|---|---|---|---|
| | | SRI | | XTI | |
| Donors | | Max inhibition | IC50 | Max inhibition | IC50 |
| Molecule | Stimulation | (%) | (nM) | (%) | (nM) |
| Ab002.10.18nR | SEB | 66.94 | 0.375 | 64.08 | 0.218 |
| | SEB + anti-PD-L1 | 71.87 | 0.193 | 72.08 | 0.234 |
| Ab002.10.21nR | SEB | 61.14 | 0.168 | 67.89 | 0.195 |
| | SEB + anti-PD-L1 | 74.57 | 0.186 | 71.62 | 0.164 |

TABLE 5

| K562 +/− CD1a: Jurkat NFL S1 CD1a TCR Reporter Assay | | |
|---|---|---|
| ImmTAAI | IC50 (pM) | Maximal Inhibition (%) |
| AB002.10.18nR | 298 | 100 |
| AB002.10.21nR | 230 | 96 |
| AB002.10 | 306 | 94 |
| AB002 | 192 | 100 |

Ab002.10.18nR and Ab00210.21.nR also exhibited minimal cross-reactivity in CD1b-d reporter assays and exhibited stable cell surface binding.

TABLE 6

| Raji A2 CD1b-d: Jurkat NFAT PD-1 reporter assays (schema represented in FIG. 4 except that CD1b/c/d present or absent in Raji A2 cells instead of CD1a; results in FIG. 5C and FIG. 5D). | | | |
|---|---|---|---|
| | CD1b-d | | |
| Molecule | Raji CD1b$^{hi}$ Max inhibition (%) | Raji CD1c$^{hi}$ Max inhibition (%) | Raji CD1d$^{hi}$ Max inhibition (%) |
| AB002.10.18nR | 5.62 | −0.185 | 7.00 |
| AB002.10.21nR | 6.84 | −12.17 | 8.97 |

Microarray screening against over 6500 membrane and secreted proteins individually overexpressed on HEK cells (Retrogenix) also confirmed very minimal cross-reactivity in a handful of instances that were subsequently de-risked using live cells, confirming a high degree of specificity for the Ab002.10.18nR molecule.

Example 6. Long Term Effect of CD1a-PD-1-ImmTAAI on CD4 T Cell Activation and Exhaustion As described above, the PD-1 receptor is a key inhibitory immune checkpoint that regulates T cell activation and is involved in T cell exhaustion, a state of cellular paralysis. As autoreactive T cells are often main drivers of autoimmunity and T cell exhaustion correlates with good prognosis, there is strong rationale to develop targeted PD-1 agonists, called ImmTAAIs, as new therapeutics to inhibit T cells and treat autoimmune diseases.

Previous studies indicated that PD-1-ImmTAAIs, once bound to target cells, activate the PD-1 pathway on interacting T cells and achieve potent immune suppression. Curnock et al., JCI Insight 6 (20): e152468 (2021).

Figure 13A:
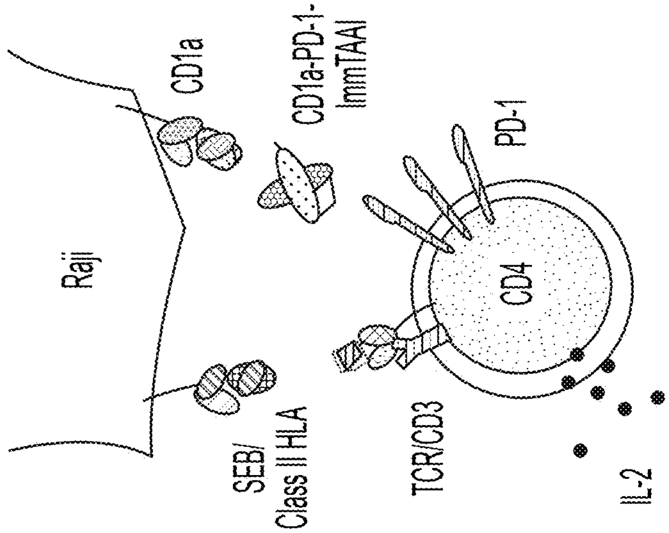
FIG. 13A. Schematic of a T cell exhaustion assay.
Figure 13B:
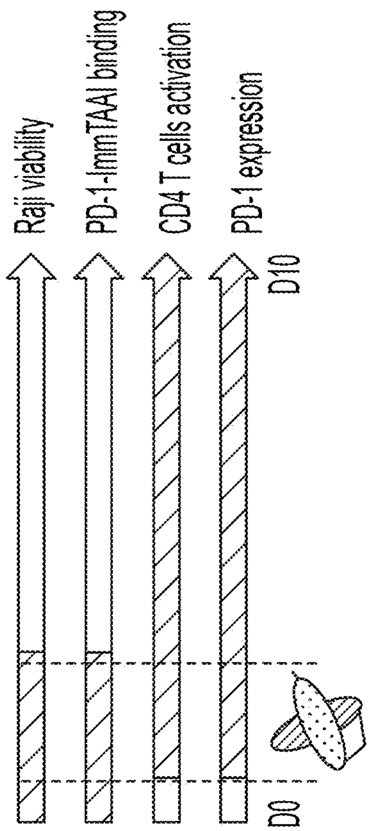
FIG. 13B. T Cell exhaustion determined by primary CD4 T cell activation. Raji viability, CD1a/PD-1 ImmTAAI binding, CD4 T cell activation, and PD-1 expression were noted over the course of ten days (D0 to D10) when assay (as diagrammed in FIG. 13A) was performed.
Figure 13D:
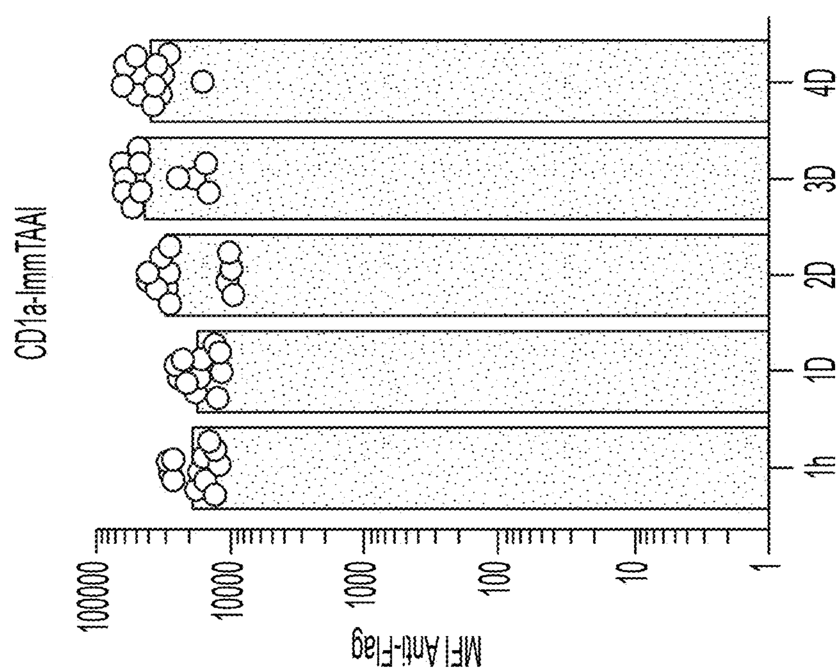
FIG. 13C and FIG. 13D. Stability measurements of CD1a-PD-1-1mmTAAI binding to Raji-CD1a at 1 hour, 1 day, 2 day, 3 day and 4 day time points during the course of T cell exhaustion (assay performed as shown in FIG. 13A and FIG. 13B).
Figure 13C:
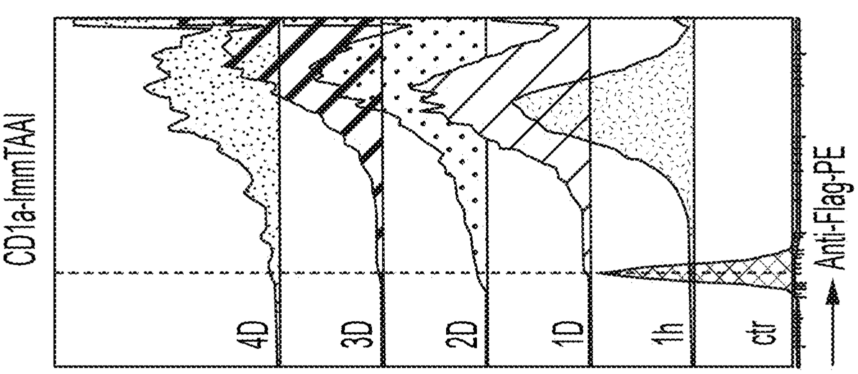
Figure 13E:
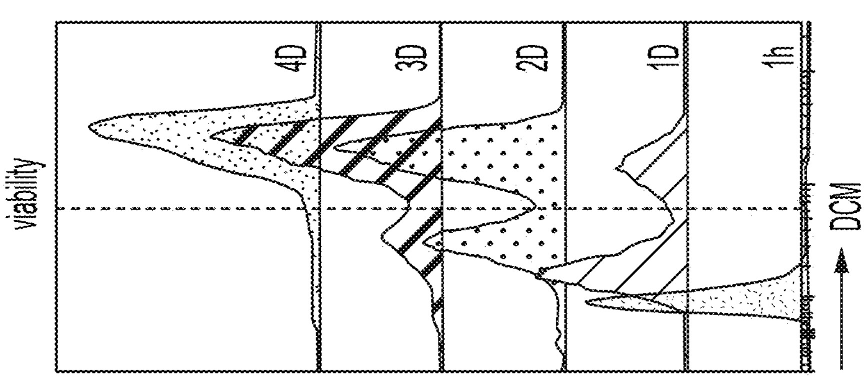
FIG. 13E, FIG. 13F. Stability of irradiated Raji-CD1a cells shown at 1 hour, 1 day, 2 day, 3 day and 4 day time points during the course of T cell exhaustion (assay performed as shown in FIG. 13A and FIG. 13B).
Figure 13F:
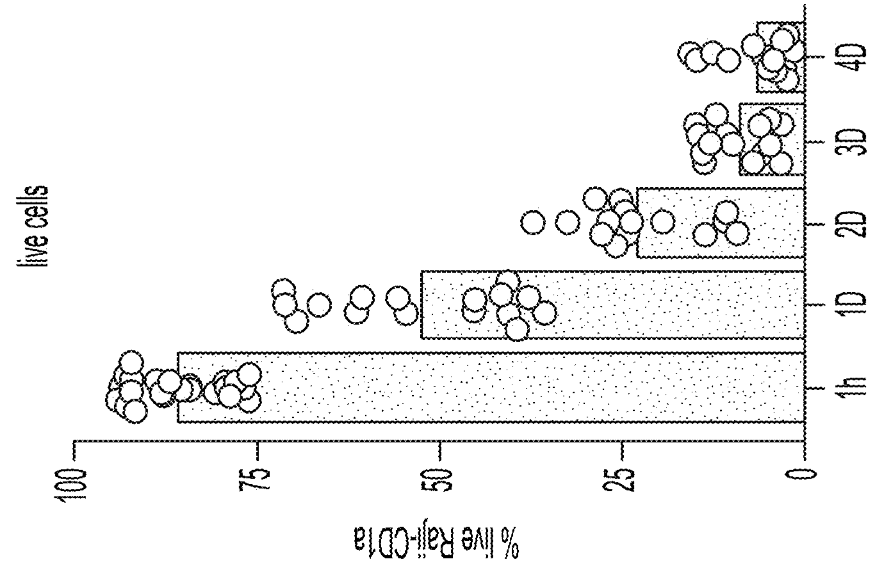
Figure 13G:
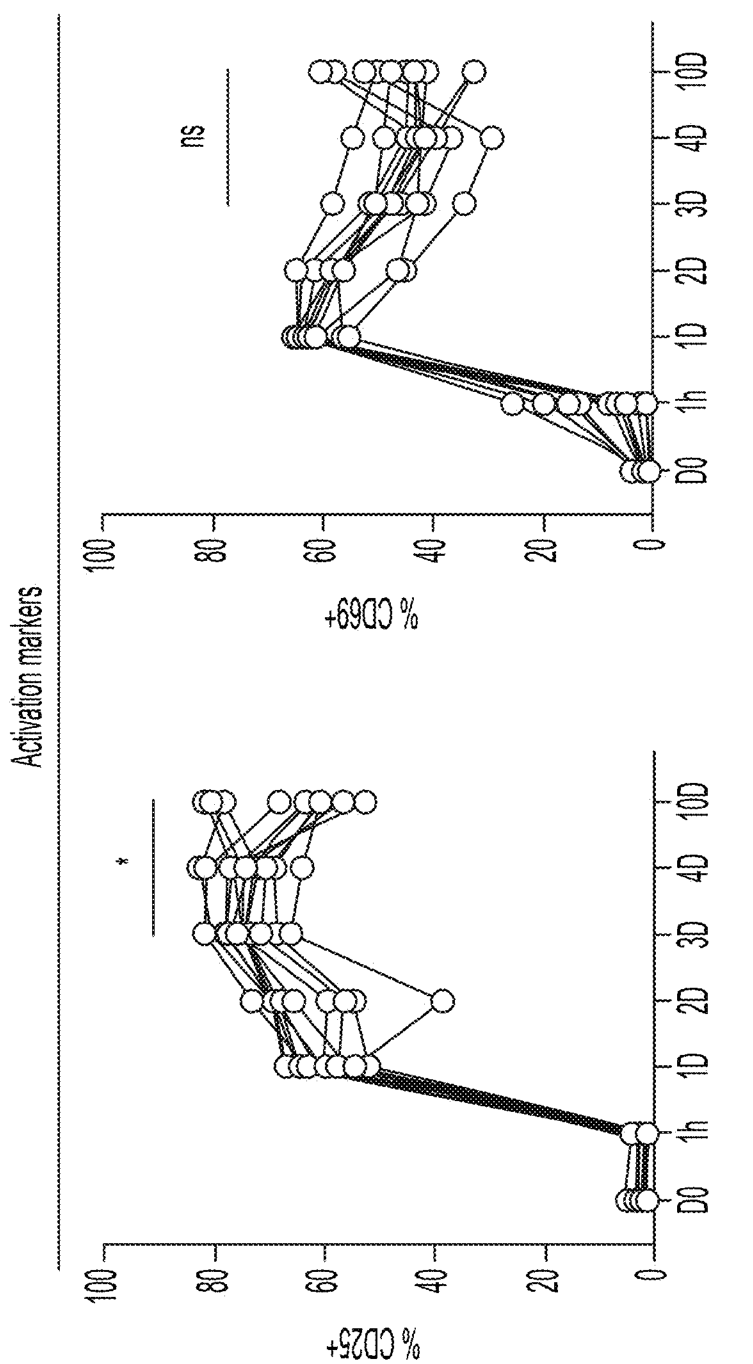
FIG. 13G. CD25 and CD69 activation marker expression shown at 1 hour, 1 day, 2 day, 3 day, 4 day, and 10 day time points during the course of T cell exhaustion (assay performed as shown in FIG. 13A and FIG. 13B).
Figure 13H:
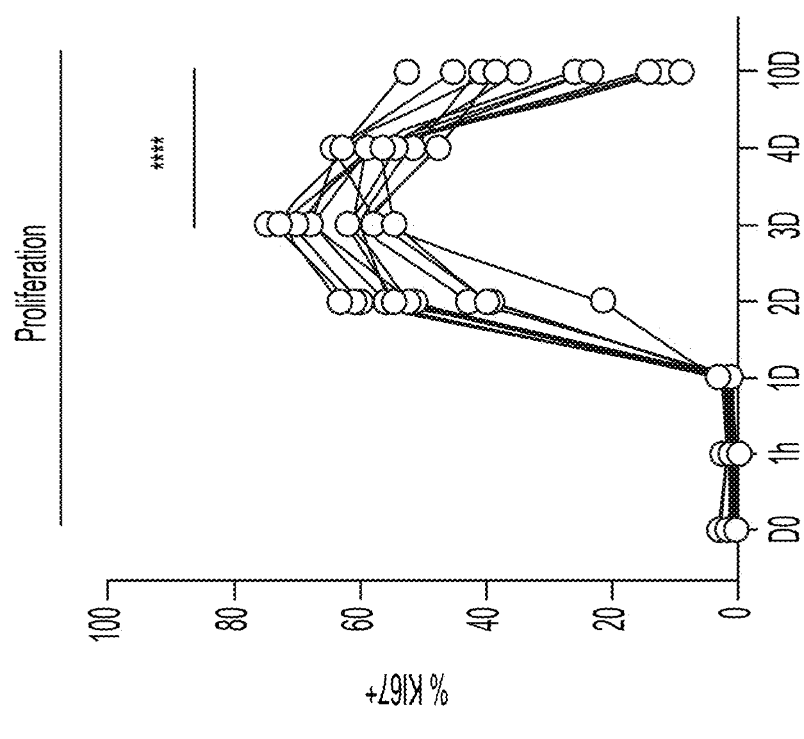
FIG. 13H, FIG. 13I, and FIG. 13J. Graphs representing levels of proliferation (via Ki67 expression) (FIG. 13H), IL-2 cytokine secretion (FIG. 13I) and TIM-3 and PD1 expression (FIG. 13J) shown at 1 hour, 1 day, 2 day, 3 day, 4 day, and 10 day time points during the course of T cell exhaustion (assay performed as shown in FIG. 13A and FIG. 13B).
Figure 13I:
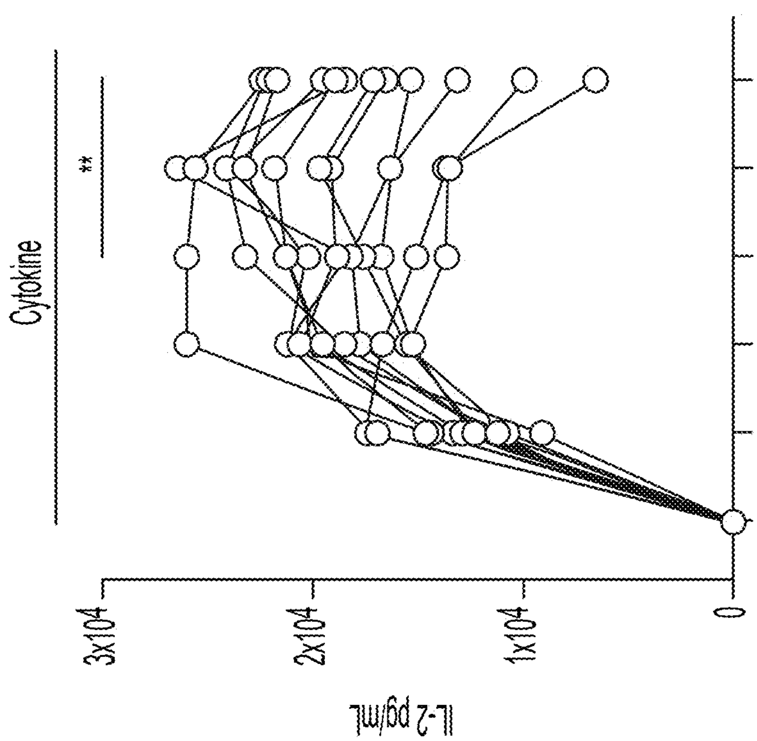
Figure 13J:
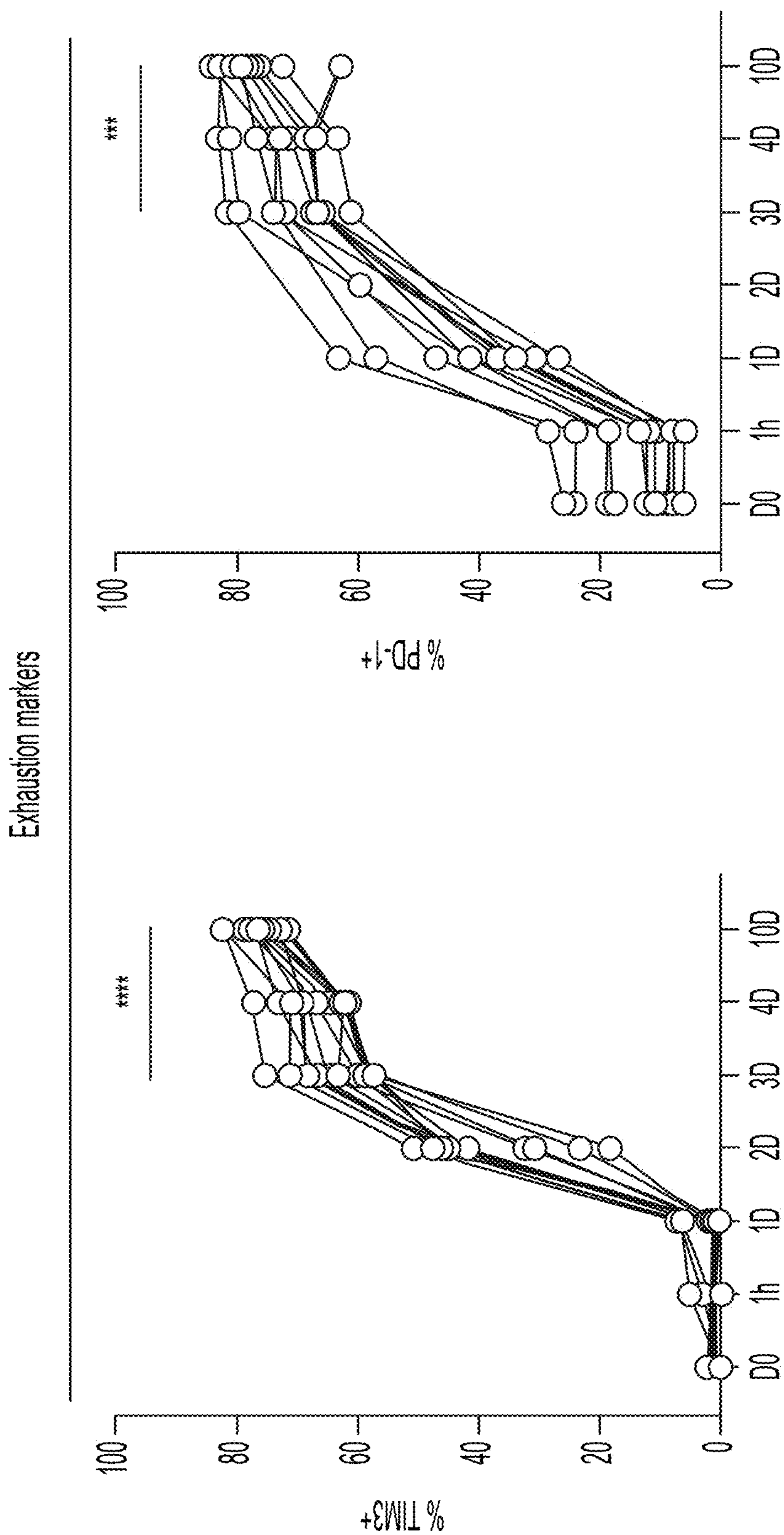

Exhaustion of CD4 T cells in the presence of a CD1a-PD-1 ImmTAAI in a CD4 T cell activation model: T cell exhaustion was determined by primary CD4 T cell activation with Raji-CD1a loaded with SEB peptide for 10 days. See FIG. 13A and FIG. 13B. It was found that CD1a-PD-1-ImmTAAI binding to Raji-CD1a is stable as shown in FIG. 13C and FIG. 13D. Irradiated Raji-CD1a cells died before day 4 as shown in FIG. 13E and FIG. 13F. CD25 and CD69 activation marker expression were stable throughout the activation as shown in FIG. 13G. Between day 3 and 10, a decrease of proliferation (as indicated by Ki67 expression) and IL-2 secretion were demonstrated (see FIGS. 13H and 13I. An increase of TIM-3 and PD1 expression, indicators of CD4 T cell exhaustion were also demonstrated between day 3 and 10 (see FIG. 13J).

Figure 14A:
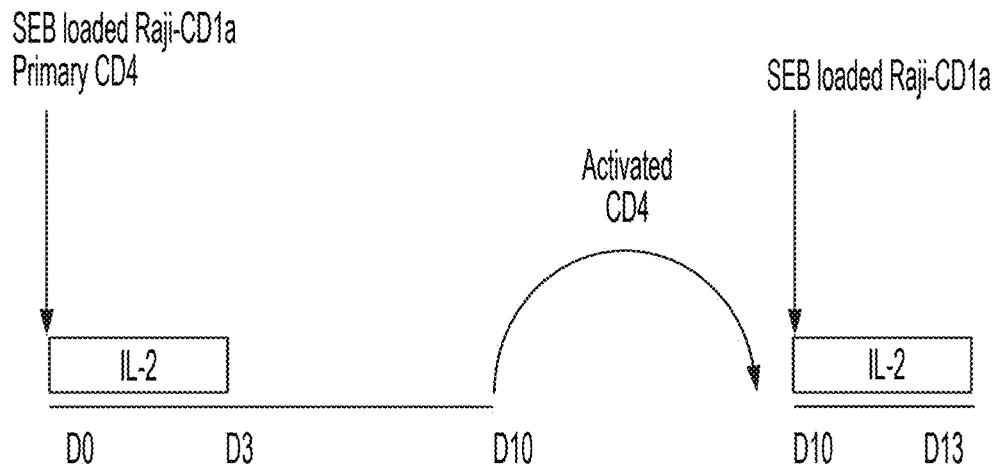
FIG. 14A and FIG. 14B. Schematic of a T cell exhaustion assay protocol (FIG. 14A) where IL-2 is provided initially between Day 0 (D0) and Day 3 (D3), and following activation of CD4 between Day 10 (D10) and Day 13 (D13). Graphs representing levels of IL-2, TNF-α, and IFN-γ on day 3 as compared to day 13 from the T cell exhaustion assay (FIG. 14B).
Figure 14B:
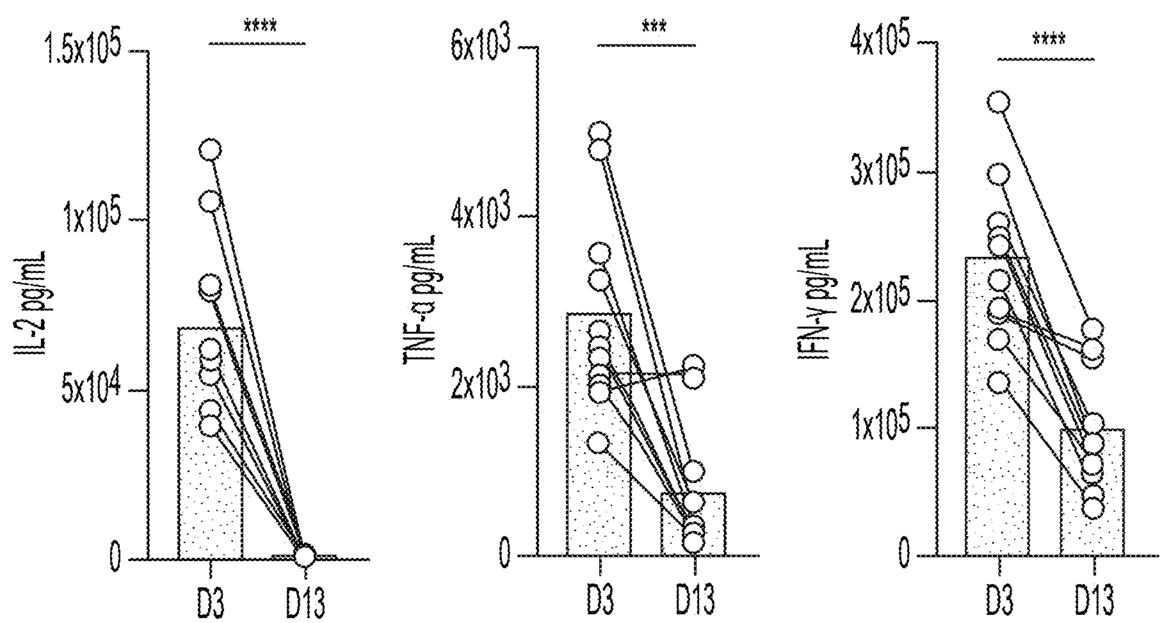

Exhausted CD4 T cells were then tested to determine cytokine secretion. Comparison cytokines secretion between activated primary CD4 T cells (day O to 3) and reactivated exhausted CD4 T cells (day 10 to 13) was determined. It was found that exhausted CD4 T cells secreted significantly less IL-2, IFNγ and TNFα than activated CD4 T cell (See FIG. 14A and FIG. 14B).

Thus, CD1a-PD-1-ImmTAAIs of the present disclosure were demonstrated to effectively inhibit CD4 T cell activation and enhance T cell exhaustion.

Figure 15A:
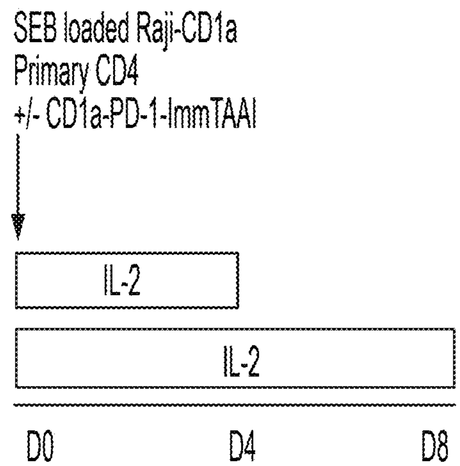
FIG. 15A, FIG. 15B and FIG. 15C. IL-2 is provided in a T cell exhaustion assay from D0 to D4, or from D0 to D8 (FIG. 15A). CD1 a-PD-1-1mmTAAI decreases IL-2 and TNFα secretion throughout CD4 T cell activation either when IL-2 provided from D0 to D4 (FIG. 15B) or when provided between D0 to D8 (FIG. 15C)
Figure 15B:
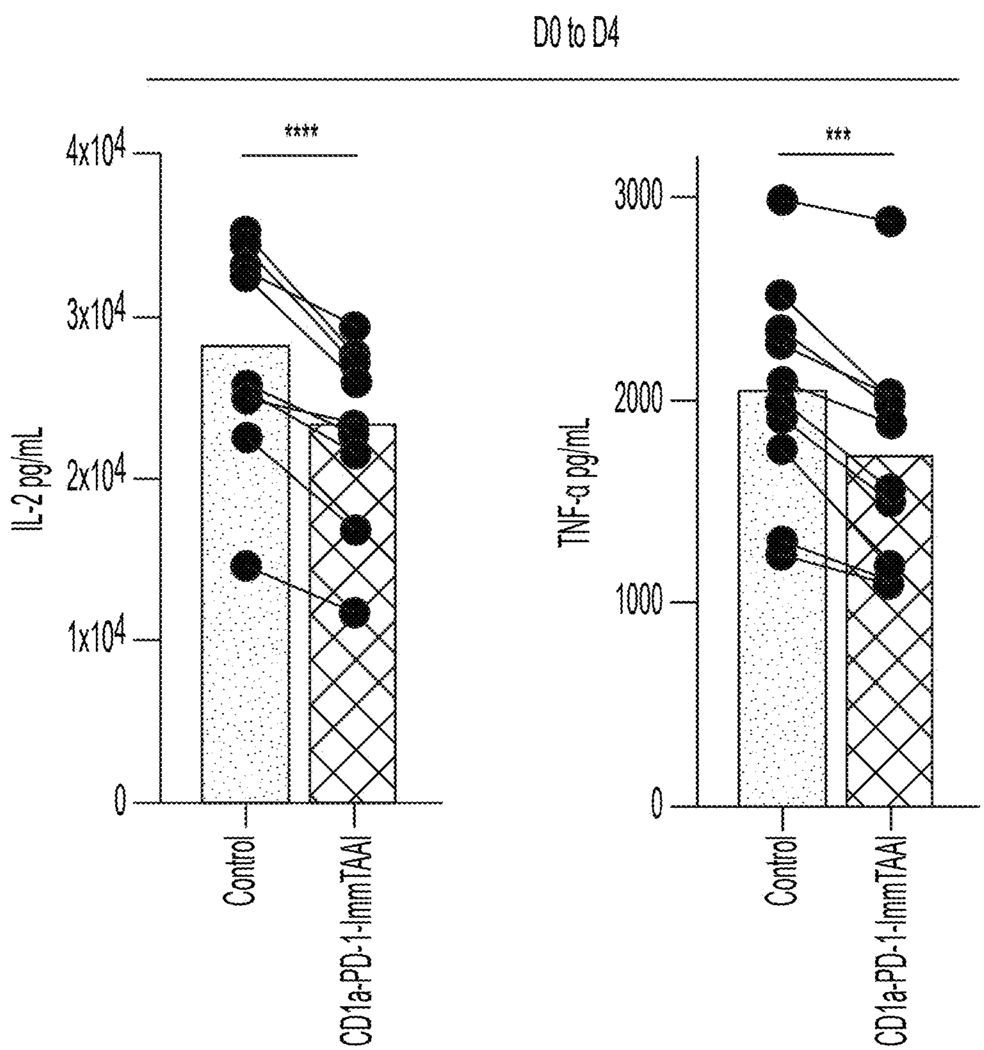
Figure 15C:
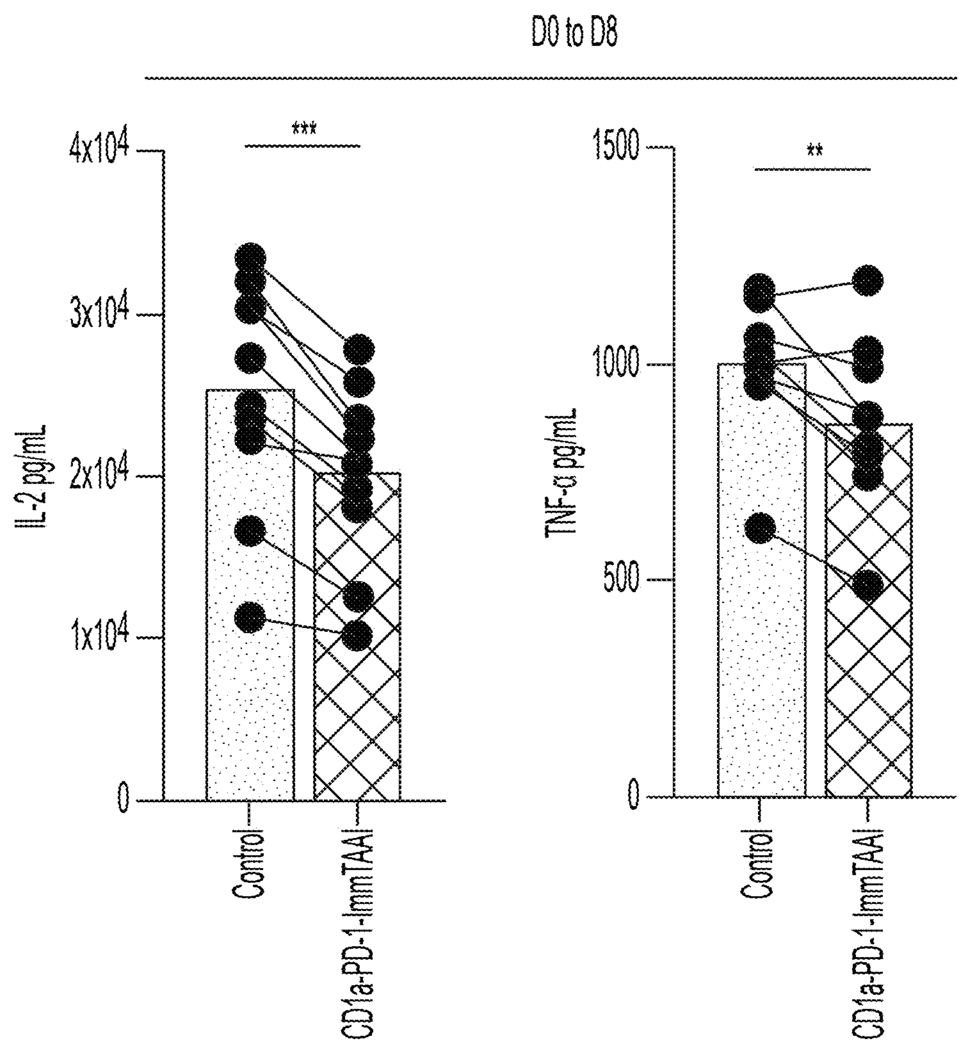

The long-term effect of CD1a-PD-1-ImmTAAI on CD4 cells was also determined. Primary CD4 T cell activation was ascertained with Raji-CD1a loaded with SEB for 8 days in the presence or absence of CD1a-PD-1-1mmTAAI for the 3 first days. CD1a-PD-1-1mmTAAI decreased IL-2 and TNFα secretion throughout the course of CD4 T cell activation. FIG. 15A, FIG. 15B and FIG. 15C. These experiments thus showed that CD1a-PD-1-ImmTAAI of the present disclosure can mediate inhibition of CD4 T cell activation.

Figure 16A:
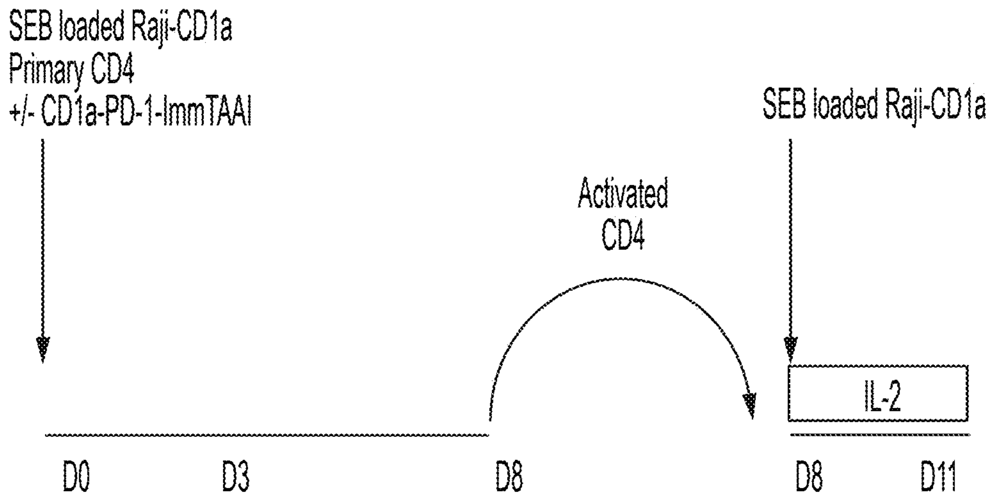
FIG. 16A. Schematic of assay with CD4 cells activated in the presence of CD1a-PD-1-ImmTAAI.
Figure 16B:
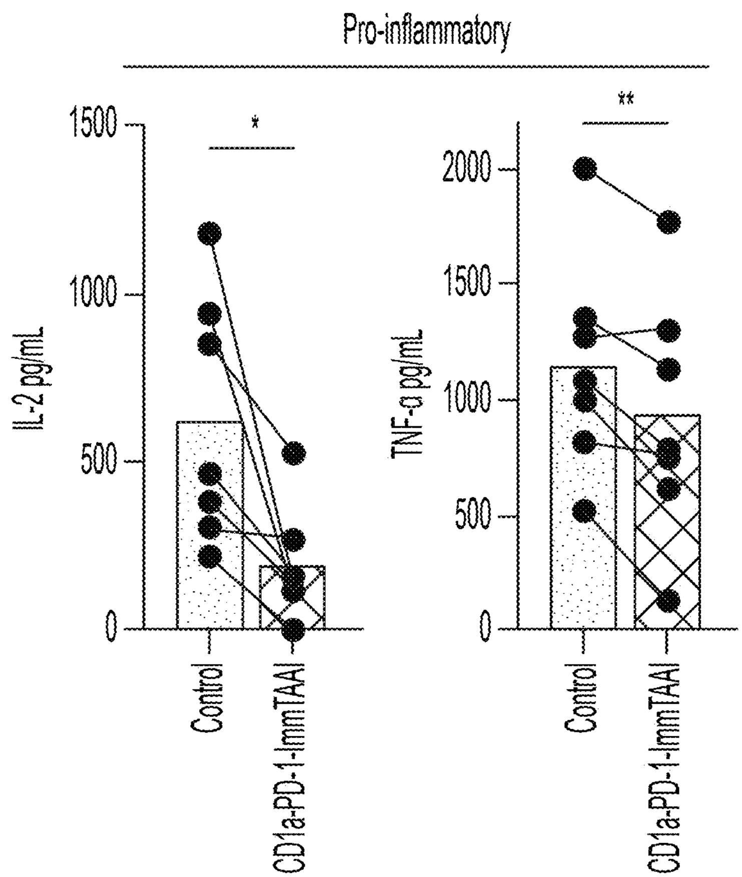
FIG. 16B. CD4 T cells activated in the presence of CD1a-PD-1-1mmTAAI produce significantly less proinflammatory (IL-2 and TNF-α) cytokines during re-activation.
Figure 16C:
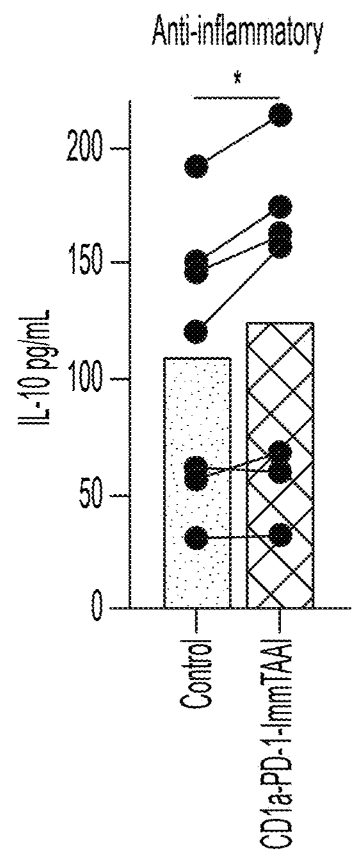
FIG. 16C. CD4 T cells activated in the presence of CD1a-PD-1-1mmTAAI produced significantly more anti-inflammatory (IL-10) cytokines during re-activation.
Figure 16D:
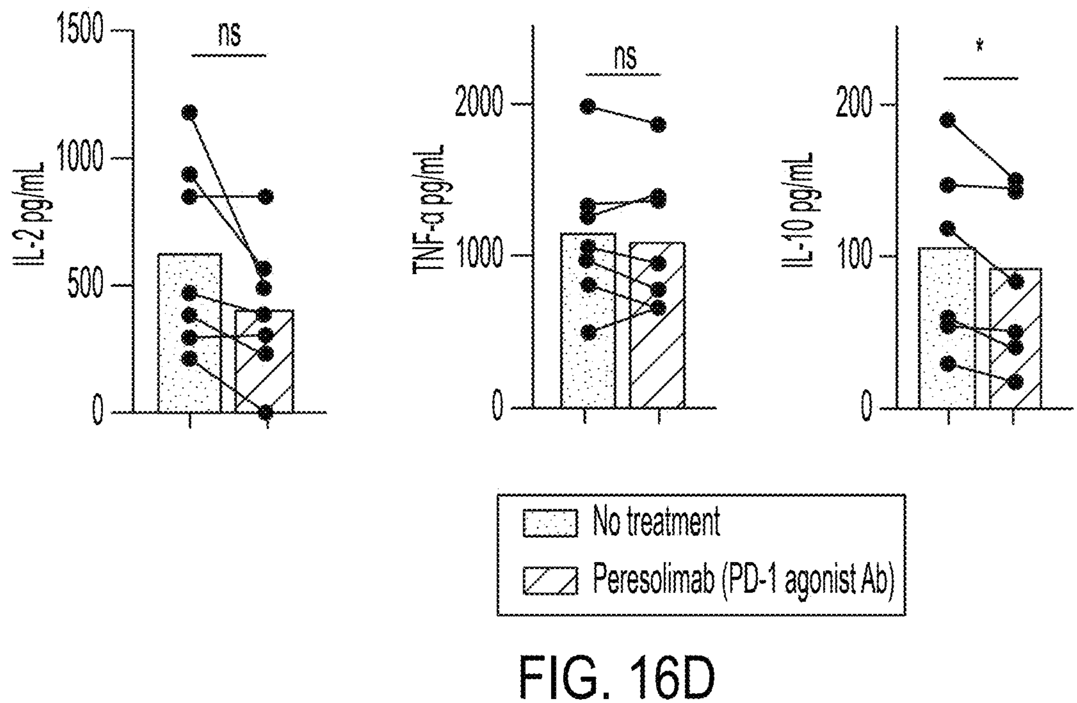
FIG. 16D. Levels of proinflammatory and anti-inflammatory cytokines when primary CD4 T cells were treated with the PD-1 agonist antibody, peresolimab, compared to CD4 T cells with no treatment.

To determine whether CD1a-PD-1-ImmTAAIs enhance T cell exhaustion, primary CD4 T cells treated with or without a CD1a-PD-1-1mmTAAI and activated with CD4 after 8 days were re-stimulated, in the absence of ImmTAAI, with Raji-CD1a loaded with SEB (See FIG. 16A). Comparison of cytokine levels produced during the re-activation is shown. CD4 T cells activated in the presence of CD1a-PD-1-1mmTAAI produced significantly less proinflammatory (IL-2 and TNF-α) and more anti-inflammatory (IL-10) cytokines during re-activation (See FIG. 16B and FIG. 16C). This was comparable to the levels of proinflammatory and anti-inflammatory cytokines seen when primary CD4 T cells were treated with the PD-1 agonist antibody, peresolimab (See FIG. 16D).

The T cell exhaustion experiment described above demonstrated that the effect of a target-directed 1mmTAA1s on CD4 T cell exhaustion can be studied in the in-vitro model established. It was found that exhausted CD4 T cells secrete significantly less IL-2, IFNγ and TNFα than activated T cells.

The results of additional experiments showed that cell-bound CD1a-PD-1-1mmTAAI inhibited CD4 T cell activation and enhanced CD4 T cell exhaustion. Thus, this long-term pharmacodynamic effect resulting from the presence of CD1a ImmTAAIs is potentially beneficial for the treatment of autoimmune diseases, including atopic dermatitis, as it demonstrates the potential for a prolonged, disease modifying effect.

Example 7: CD1a/PD-1 Bispecific Molecules Function in Atopic Dermatitis (AD) Explants The function of CD1a/PD-1 bispecific molecules were evaluated in atopic dermatitis (AD) explants. Four (4) mm lesional and perilesional skin punches from AD donors were cultured ex vivo and treated for 48 or 96 hours with either a CD1a/PD-1 bispecific molecule (WT Ab002-H5 HLE; SEQ ID NO: 73 and 58) or a control vehicle (each experimental arm in duplicate). After the prescribed time periods, the cultured and treated skin was frozen in optimal cutting temperature (OCT) for cryosectioning and immunofluorescence (IF). The culture media was also collected for cytokine analysis.

Figure 17:
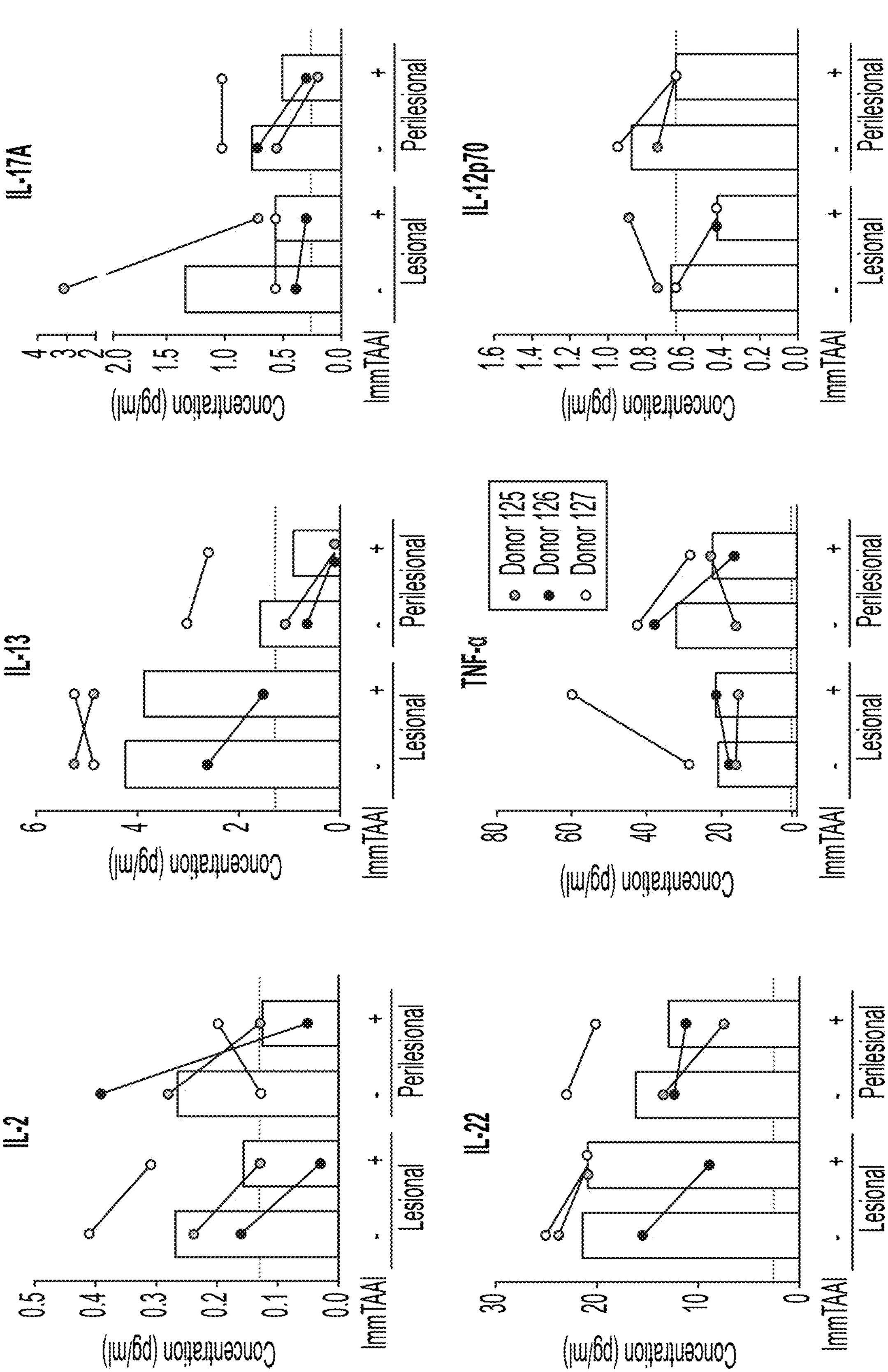
FIG. 17. Graphs showing levels of IL-2, IL-13, IL17A, IL-22, TNF-α, and IL012p70 using Luminex analysis of explant culture media from atopic dermatitis lesional or perilesional skin punches treated with either a CD1a/PD-1 bispecific molecule or a control vehicle as described in Example 7.
Figure 18:
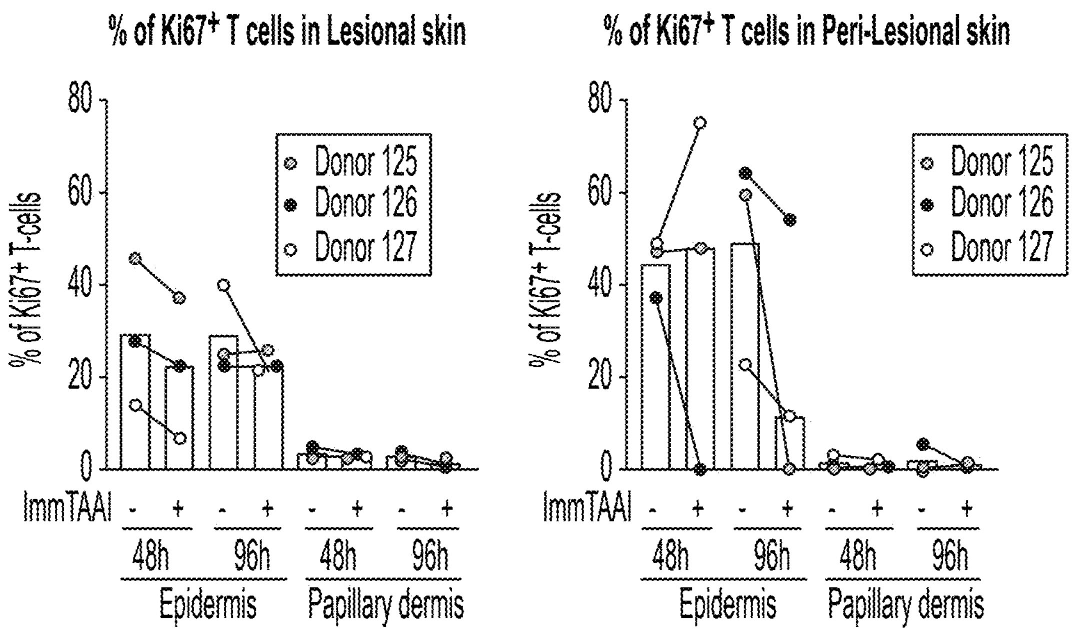
FIG. 18. The percentage of proliferating (Ki67+) T cells calculated by staining T cells with an anti-CD3 Ab (Invitrogen A51001) and staining proliferating cells with an anti-Ki67 ab (Cell Signaling 94495) in epidermis or papillary dermis of lesional or perilesional skin punches treated with either a CD1a/PD-1 bispecific molecule or a control vehicle as described in Example 7.
Figure 19:
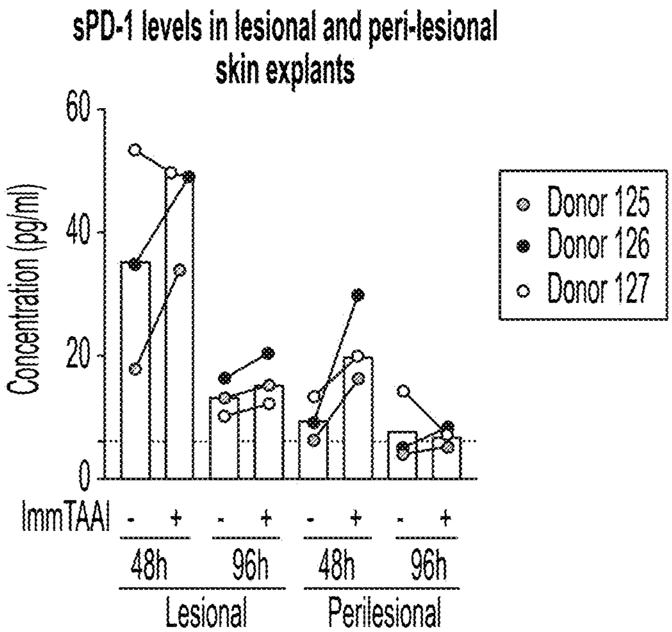
FIG. 19. Graph showing levels of soluble PD-1 using Luminex analysis of explant culture media from atopic dermatitis lesional or perilesional skin punches treated with either a CD1a/PD-1 bispecific molecule or a control vehicle as described in Example 7.
Figure 20A:
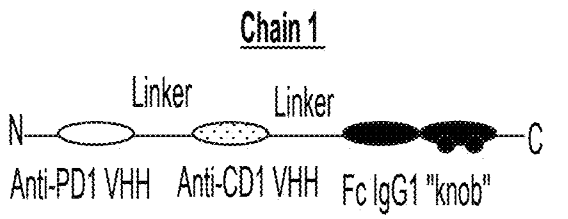
FIG. 20A, FIG. 20B, and FIG. 20C. A schematic of the CD1a/PD-1 bispecific molecule illustrating Chain 1 of the bispecific molecule in FIG. 20A, Chain 2 in FIG. 20B, and the complete folded structure in FIG. 20C.
Figure 20B:
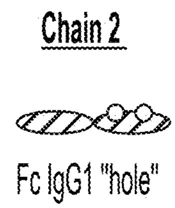
Figure 20C:
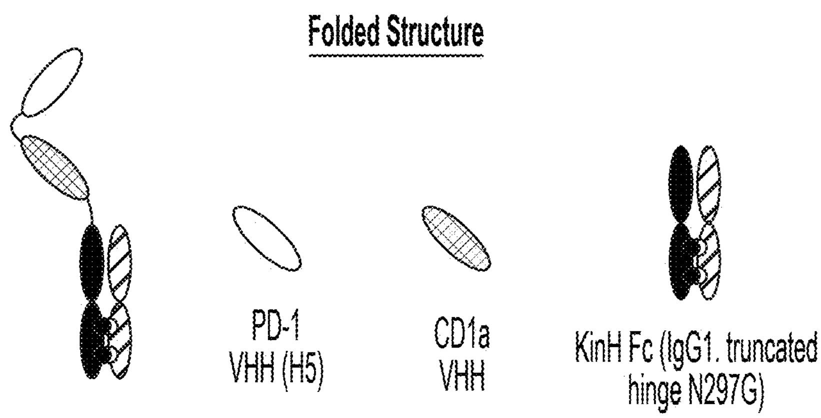

As shown in FIG. 17, treatment with the CD1a/PD-1 bispecific molecule demonstrated a reduction of Th1, Th2, Th17 and Th22 cytokines in lesional and perilesional skin. A reduction in proliferating T cells was also observed in the perilesional epidermis following treatment with the CD1a/PD-1 bispecific molecule (See FIG. 18). Treatment with the CD1a/PD-1 bispecific molecule also demonstrated an increase in soluble PD-1 (sPD-1) levels in both lesional and perilesional skin explants, indicating that sPD-1 may serve as an indicator of target engagement (See FIG. 19).

CONCLUSION

As described above, the CD1a/PD-1 ImmTAAI molecules of the present disclosure are unique for various reasons including (i) lipid independent binding to CD1a; (ii) picomolar potency in cellular assays of PD-1-mediated T cell suppression and CD1a autoreactive T cell blockade; (iii) high level of selectivity in biochemical and cellular assays; and (iv) CD1a target engagement in human skin explants.

The CD1a targeting arm of these molecules have been shown to demonstrate affinities with a kD of less than or about 1 nM, and the ability to block CD1a autoreactive T cell activity in their bispecific formats. The PD-1 arm has been shown to demonstrate targeting-depending PD-1 agonist activity and has been optimized for efficacy. The molecules of the present disclosure also demonstrate selectivity that provides a potentially favorable therapeutic window over other CD1 targeting molecules. The molecules have also been engineered and optimized to increase their half-lives (with inclusion of an HLE domain) and reduce their immunogenicity (with further humanization) while maintaining the unique attributes set forth above.

SEQUENCE LISTING

```
Sequence total quantity: 133
SEQ ID NO: 1            moltype = AA  length = 8
FEATURE                 Location/Qualifiers
REGION                  1..8
                        note = Synthetic: First binding domain, CDR1
source                  1..8
                        mol_type = protein
                        organism = synthetic construct
SEQUENCE: 1
GFTFSSYA                                                            8

SEQ ID NO: 2            moltype = AA  length = 8
FEATURE                 Location/Qualifiers
REGION                  1..8
                        note = Synthetic: First binding domain, CDR2
source                  1..8
                        mol_type = protein
                        organism = synthetic construct
SEQUENCE: 2
IASDGAST                                                            8

SEQ ID NO: 3            moltype = AA  length = 12
FEATURE                 Location/Qualifiers
REGION                  1..12
                        note = Synthetic: First binding domain, CDR3
```

-continued

```
source                  1..12
                        mol_type = protein
                        organism = synthetic construct
SEQUENCE: 3
CARGGYLTYD RY                                                           12

SEQ ID NO: 4            moltype = AA  length = 11
FEATURE                 Location/Qualifiers
REGION                  1..11
                        note = Synthetic: Second binding domain, CDR1 Ab002
source                  1..11
                        mol_type = protein
                        organism = synthetic construct
SEQUENCE: 4
GRTFNPGDLM G                                                            11

SEQ ID NO: 5            moltype = AA  length = 11
FEATURE                 Location/Qualifiers
REGION                  1..11
                        note = Synthetic: Second binding domain, CDR1 Ab007
source                  1..11
                        mol_type = protein
                        organism = synthetic construct
SEQUENCE: 5
GRAFRPHNVM A                                                            11

SEQ ID NO: 6            moltype = AA  length = 11
FEATURE                 Location/Qualifiers
REGION                  1..11
                        note = Synthetic: Second binding domain, CDR1 Ab052
source                  1..11
                        mol_type = protein
                        organism = synthetic construct
SEQUENCE: 6
GRTFSPSDLM G                                                            11

SEQ ID NO: 7            moltype = AA  length = 15
FEATURE                 Location/Qualifiers
REGION                  1..15
                        note = Synthetic: Second binding domain, CDR2 Ab002
source                  1..15
                        mol_type = protein
                        organism = synthetic construct
SEQUENCE: 7
AIKWGPTYYA DSVKG                                                        15

SEQ ID NO: 8            moltype = AA  length = 15
FEATURE                 Location/Qualifiers
REGION                  1..15
                        note = Synthetic: Second binding domain, CDR2 Ab007
source                  1..15
                        mol_type = protein
                        organism = synthetic construct
SEQUENCE: 8
AARWSGIYYA ESVKG                                                        15

SEQ ID NO: 9            moltype = AA  length = 15
FEATURE                 Location/Qualifiers
REGION                  1..15
                        note = Synthetic: Second binding domain, CDR2 Ab052
source                  1..15
                        mol_type = protein
                        organism = synthetic construct
SEQUENCE: 9
AIKWGPTYYS DSVKG                                                        15

SEQ ID NO: 10           moltype = AA  length = 14
FEATURE                 Location/Qualifiers
REGION                  1..14
                        note = Synthetic: Second binding domain, CDR3 Ab002
source                  1..14
                        mol_type = protein
                        organism = synthetic construct
SEQUENCE: 10
GSGTFSSNYR DFEY                                                         14

SEQ ID NO: 11           moltype = AA  length = 16
FEATURE                 Location/Qualifiers
REGION                  1..16
```

-continued

```
                         note = Synthetic: Second binding domain, CDR3 Ab007
source                   1..16
                         mol_type = protein
                         organism = synthetic construct
SEQUENCE: 11
STAQDMTLAL MSDYDY                                                 16

SEQ ID NO: 12            moltype = AA  length = 14
FEATURE                  Location/Qualifiers
REGION                   1..14
                         note = Synthetic: Second binding domain, CDR3 Ab052
source                   1..14
                         mol_type = protein
                         organism = synthetic construct
SEQUENCE: 12
GSSTFSANYR DYEY                                                   14

SEQ ID NO: 13            moltype = AA  length = 147
FEATURE                  Location/Qualifiers
REGION                   1..147
                         note = Synthetic: amino acid sequence of the extracellular
                          region of human PD-1
source                   1..147
                         mol_type = protein
                         organism = synthetic construct
SEQUENCE: 13
FLDSPDRPWN PPTFSPALLV VTEGDNATFT CSFSNTSESF VLNWYRMSPS NQTDKLAAFP  60
EDRSQPGQDC RFRVTQLPNG RDFHMSVVRA RRNDSGTYLC GAISLAPKAQ IKESLRAELR  120
VTERRAEVPT AHPSPSPRPA GQFQTLV                                     147

SEQ ID NO: 14            moltype = AA  length = 25
FEATURE                  Location/Qualifiers
REGION                   1..25
                         note = Synthetic: First binding domain, FR1
source                   1..25
                         mol_type = protein
                         organism = synthetic construct
SEQUENCE: 14
AVQLVESGGG LVQPGGSLRL SCAAS                                       25

SEQ ID NO: 15            moltype = AA  length = 17
FEATURE                  Location/Qualifiers
REGION                   1..17
                         note = Synthetic: First binding domain, FR2
source                   1..17
                         mol_type = protein
                         organism = synthetic construct
SEQUENCE: 15
MTWVRQAPGK GPEWVSA                                                17

SEQ ID NO: 16            moltype = AA  length = 37
FEATURE                  Location/Qualifiers
REGION                   1..37
                         note = Synthetic: First binding domain, FR3
source                   1..37
                         mol_type = protein
                         organism = synthetic construct
SEQUENCE: 16
SYADSVKGRF TISRDNSKNT LYLQMNSLRP EDTAVYY                          37

SEQ ID NO: 17            moltype = AA  length = 17
FEATURE                  Location/Qualifiers
REGION                   1..17
                         note = Synthetic: First binding domain, FR4
source                   1..17
                         mol_type = protein
                         organism = synthetic construct
SEQUENCE: 17
YLTYDRYGQG TLVTVSS                                                17

SEQ ID NO: 18            moltype = AA  length = 117
FEATURE                  Location/Qualifiers
REGION                   1..117
                         note = Synthetic: amino acid sequence of an exemplary
                          camelid PD-1 agonist VHH
source                   1..117
                         mol_type = protein
                         organism = synthetic construct
SEQUENCE: 18
```

-continued

```
EVQLVESGGA LVQPGGSLRL SCAASGFTFS SYAMTWVRQA PGKGPEWVSA IASDGASTSY  60
LDSVKGRFTV SRDNAKNTLY LQMNSLKPED TAVYYCARGG YLTYDRYGQG TQVTVSS     117

SEQ ID NO: 19          moltype = AA  length = 115
FEATURE                Location/Qualifiers
REGION                 1..115
                       note = Synthetic: amino acid sequence of a soluble fragment
                        of human PD-L1 that is capable of binding to PD-1
source                 1..115
                       mol_type = protein
                       organism = synthetic construct
SEQUENCE: 19
FTVTVPKDLY WEYGSNMTIE CKFPVEKQLD LAALIVYWEM EDKNIIQFVH GEEDLKVQHS  60
SYRQRARLLK DQLSLGNAAL QITDVKLQDA GVYRCMISYG GADYKRITVK VNAPY       115

SEQ ID NO: 20          moltype = AA  length = 117
FEATURE                Location/Qualifiers
REGION                 1..117
                       note = Synthetic: SEQ ID NO: 20 (H5) is the amino acid
                        sequence of a humanized version of the exemplary PD-1
                        agonist VHH of SEQ ID NO: 18
source                 1..117
                       mol_type = protein
                       organism = synthetic construct
SEQUENCE: 20
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSS     117

SEQ ID NO: 21          moltype = AA  length = 123
FEATURE                Location/Qualifiers
REGION                 1..123
                       note = Synthetic: Second binding domain, Ab002.10
source                 1..123
                       mol_type = protein
                       organism = synthetic construct
SEQUENCE: 21
EVQLLESGGG LVQPGGSLRL SCAPSGRTFN PGDLMGWFRQ APGKEREFVA AIKWGPTYYA  60
DSVKGRFTIS RDYSKNTVYL QMNSLRAEDT AVYYCAGKGS GTFSSNYRDF EYWGQGTLVT  120
VSS                                                               123

SEQ ID NO: 22          moltype = AA  length = 123
FEATURE                Location/Qualifiers
REGION                 1..123
                       note = Synthetic: Second binding domain, Ab002.10.5nR:
source                 1..123
                       mol_type = protein
                       organism = synthetic construct
SEQUENCE: 22
EVQLLESGGG LVQPGGSLRL SCAPSGRTFN PGDLMGWFRQ APGKEREFVS AIKWGPTYYA  60
DSVKGRFTIS RDYSRNTLYL QMNSLRAEDT AVYYCAAKGS GTFSSNYRDF EYWGQGTLVT  120
VSS                                                               123

SEQ ID NO: 23          moltype = AA  length = 123
FEATURE                Location/Qualifiers
REGION                 1..123
                       note = Synthetic: Second binding domain, Ab002.10.5n:
source                 1..123
                       mol_type = protein
                       organism = synthetic construct
SEQUENCE: 23
EVQLLESGGG LVQPGGSLRL SCAPSGRTFN PGDLMGWFRQ APGKEREFVS AIKWGPTYYA  60
DSVKGRFTIS RDYSKNTLYL QMNSLRAEDT AVYYCAAKGS GTFSSNYRDF EYWGQGTLVT  120
VSS                                                               123

SEQ ID NO: 24          moltype = AA  length = 123
FEATURE                Location/Qualifiers
REGION                 1..123
                       note = Synthetic: Second binding domain, Ab002.10.17nR:
source                 1..123
                       mol_type = protein
                       organism = synthetic construct
SEQUENCE: 24
EVQLLESGGG LVQPGGSLRL SCAPSGRTFN PGDLMGWFRQ APGKGREFVS AIKWGPTYYA  60
DSVKGRFTIS RDYSRNTVYL QMNSLRAEDT AVYYCAAKGS GTFSSNYRDF EYWGQGTLVT  120
VSS                                                               123

SEQ ID NO: 25          moltype = AA  length = 123
FEATURE                Location/Qualifiers
REGION                 1..123
```

-continued

```
                        note = Synthetic: Second binding domain, Ab002.10.18nR:
source                  1..123
                        mol_type = protein
                        organism = synthetic construct
SEQUENCE: 25
EVQLLESGGG LVQPGGSLRL SCAPSGRTFN PGDLMGWFRQ APGKGLEFVS AIKWGPTYYA  60
DSVKGRFTIS RDYSRNTVYL QMNSLRAEDT AVYYCAAKGS GTFSSNYRDF EYWGQGTLVT  120
VSS                                                                123

SEQ ID NO: 26           moltype = AA  length = 123
FEATURE                 Location/Qualifiers
REGION                  1..123
                        note = Synthetic: Second binding domain, Ab002.10.21nR:
source                  1..123
                        mol_type = protein
                        organism = synthetic construct
SEQUENCE: 26
EVQLLESGGG LVQPGGSLRL SCAPSGRTFN PGDLMGWFRQ APGKGREFVS AIKWGPTYYA  60
DSVKGRFTIS RDYSRNTLYL QMNSLRAEDT AVYYCAAKGS GTFSSNYRDF EYWGQGTLVT  120
VSS                                                                123

SEQ ID NO: 27           moltype = AA  length = 123
FEATURE                 Location/Qualifiers
REGION                  1..123
                        note = Synthetic: Second binding domain, Ab002.10.21n:
source                  1..123
                        mol_type = protein
                        organism = synthetic construct
SEQUENCE: 27
EVQLLESGGG LVQPGGSLRL SCAPSGRTFN PGDLMGWFRQ APGKGREFVS AIKWGPTYYA  60
DSVKGRFTIS RDYSKNTLYL QMNSLRAEDT AVYYCAAKGS GTFSSNYRDF EYWGQGTLVT  120
VSS                                                                123

SEQ ID NO: 28           moltype = AA  length = 124
FEATURE                 Location/Qualifiers
REGION                  1..124
                        note = Synthetic: Second binding domain, Ab007.11
source                  1..124
                        mol_type = protein
                        organism = synthetic construct
SEQUENCE: 28
EVQLLESGGG LVQPGGSLRL SCAASGRAFR PHNVMAWFRQ APGKEREFVA AARWSGIYYA  60
ESVKGRFTIS RDYSKNTVYL QMNSLRPEDT AVYYCAVSTA QDMTLALMSD YDYWGQGTLV  120
TVSS                                                               124

SEQ ID NO: 29           moltype = AA  length = 123
FEATURE                 Location/Qualifiers
REGION                  1..123
                        note = Synthetic: Second binding domain, Ab052.9
source                  1..123
                        mol_type = protein
                        organism = synthetic construct
SEQUENCE: 29
EVQLLESGGG LVQPGGSLRL SCAASGRTFS PSDLMGWFRQ APGKEREFVA AIKWGPTYYS  60
DSVKGRFTIS RDYSKNTVYL QMNSLRAEDT AVYYCAGKGS STFSANYRDY EYWGQGTLVT  120
VSS                                                                123

SEQ ID NO: 30           moltype = AA  length = 25
FEATURE                 Location/Qualifiers
REGION                  1..25
                        note = Synthetic: Second binding domain, FR1 (most
                         humanized form)
source                  1..25
                        mol_type = protein
                        organism = synthetic construct
SEQUENCE: 30
EVQLLESGGG LVQPGGSLRL SCAAS                                       25

SEQ ID NO: 31           moltype = AA  length = 14
FEATURE                 Location/Qualifiers
REGION                  1..14
                        note = Synthetic: Second binding domain, FR2 (most
                         humanized form)
source                  1..14
                        mol_type = protein
                        organism = synthetic construct
SEQUENCE: 31
WVRQAPGKGL EWVS                                                   14
```

-continued

```
SEQ ID NO: 32          moltype = AA  length = 33
FEATURE                Location/Qualifiers
REGION                 1..33
                       note = Synthetic: Second binding domain, FR3 (most
                        humanized form)
source                 1..33
                       mol_type = protein
                       organism = synthetic construct
SEQUENCE: 32
RFTISRDNSK NTLYLQMNSL RAEDTAVYYC AAK                              33

SEQ ID NO: 33          moltype = AA  length = 11
FEATURE                Location/Qualifiers
REGION                 1..11
                       note = Synthetic: Second binding domain, FR4 (most
                        humanized form)
source                 1..11
                       mol_type = protein
                       organism = synthetic construct
SEQUENCE: 33
WGQGTLVTVS S                                                      11

SEQ ID NO: 34          moltype = AA  length = 123
FEATURE                Location/Qualifiers
REGION                 1..123
                       note = Synthetic: Second binding domain, Ab002 Llama WT
source                 1..123
                       mol_type = protein
                       organism = synthetic construct
SEQUENCE: 34
EVQLVESGGG LVQAGGSLRL SCAPSGRTFN PGDLMGWFRQ APGKEREFVA AIKWGPTYYA  60
DSVKGRFTIS RDYVRNTVYV QMNDLKAEDT AVYYCAGKGS GTFSSNYRDF EYWGQGTQVT  120
VSS                                                               123

SEQ ID NO: 35          moltype = AA  length = 124
FEATURE                Location/Qualifiers
REGION                 1..124
                       note = Synthetic: Second binding domain, Ab007 Llama WT
source                 1..124
                       mol_type = protein
                       organism = synthetic construct
SEQUENCE: 35
EVQLVESGGR LAQAGGSLRL SCAASGRAFR PHNVMAWFRQ APEKEREFVA AARWSGIYYA  60
ESVKGRFSVS RDYDKNAVFL QMNGLKPEDT AVYYCAVSTA QDMTLALMSD YDYWGQGIQV  120
TVSS                                                              124

SEQ ID NO: 36          moltype = AA  length = 123
FEATURE                Location/Qualifiers
REGION                 1..123
                       note = Synthetic: Second binding domain, Ab052 Llama WT
source                 1..123
                       mol_type = protein
                       organism = synthetic construct
SEQUENCE: 36
EVQLVESGGG LVQAGGSLRL SCAASGRTFS PSDLMGWFRQ APGKEREFVA AIKWGPTYYS  60
DSVKGRFTTS RDYVGNTVYL QMNDLKAEDT AVYHCAGKGS STFSANYRDY EYWGQGTQVT  120
VSS                                                               123

SEQ ID NO: 37          moltype = AA  length = 217
FEATURE                Location/Qualifiers
REGION                 1..217
                       note = Synthetic: Human IgG1 Fc region (CH2 and CH3
                        domains), unmodified
source                 1..217
                       mol_type = protein
                       organism = synthetic construct
SEQUENCE: 37
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                          217

SEQ ID NO: 38          moltype = AA  length = 217
FEATURE                Location/Qualifiers
REGION                 1..217
                       note = Synthetic: IgG1 Fc region sequence with four
                        substitutions, (bold), relative to the above unmodified
                        IgG1 Fc sequence. These are an N297G substitution for
                        inhibiting binding to Fc?R as well as a T366S, L368A, and
```

```
                       Y407V substitutions (hole-forming substitutions) for
                       enhancing dimerization with another Fc region (e.g., SEQ
                       ID NO: 40)
source                1..217
                      mol_type = protein
                      organism = synthetic construct
SEQUENCE: 38
APELLGGPSV FLFPPKPKDT LMISRTPEVT CVVVDVSHED PEVKFNWYVD GVEVHNAKTK  60
PREEQYGSTY RVVSVLTVLH QDWLNGKEYK CKVSNKALPA PIEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                           217

SEQ ID NO: 39         moltype = AA  length = 217
FEATURE               Location/Qualifiers
REGION                1..217
                      note = Synthetic: IgG1 Fc region sequence identical to SEQ
                       ID NO: 38 above except that it has additional M252Y, S254T
                       and T256E substitutions (EU numbering scheme as set forth
                       in Kabat), shown in bold, to enhance binding to FcRn
source                1..217
                      mol_type = protein
                      organism = synthetic construct
SEQUENCE: 39
APELLGGPSV FLFPPKPKDT LYITREPEVT CVVVDVSHED PEVKFNWYVD GVEVHNAKTK  60
PREEQYGSTY RVVSVLTVLH QDWLNGKEYK CKVSNKALPA PIEKTISKAK GQPREPQVYT  120
LPPSRDELTK NQVSLSCAVK GFYPSDIAVE WESNGQPENN YKTTPPVLDS DGSFFLVSKL  180
TVDKSRWQQG NVFSCSVMHE ALHNHYTQKS LSLSPGK                           217

SEQ ID NO: 40         moltype = AA  length = 217
FEATURE               Location/Qualifiers
REGION                1..217
                      note = Synthetic: IgG1 Fc region sequence having two
                       substitutions, (bold), relative to the above unmodified
                       IgG1 Fc sequence (SEQ ID NO: 37). These are an N297G
                       substitution for inhibiting binding to Fc?R as well as a
                       T366W substitution (knob-forming substitution) for
                       enhancing dimerization with another Fc region (e.g., SEQ
                       ID NO: 38) containing T366S, L368A, and Y407V
                       substitutions (hole-forming substitutions).
source                1..217
                      mol_type = protein
                      organism = synthetic construct
SEQUENCE: 40
APELLGGPSV FLFPPKPKDT LMISRTPEVT CVVVDVSHED PEVKFNWYVD GVEVHNAKTK  60
PREEQYGSTY RVVSVLTVLH QDWLNGKEYK CKVSNKALPA PIEKTISKAK GQPREPQVYT  120
LPPSRDELTK NQVSLWCLVK GFYPSDIAVE WESNGQPENN YKTTPPVLDS DGSFFLYSKL  180
TVDKSRWQQG NVFSCSVMHE ALHNHYTQKS LSLSPGK                           217

SEQ ID NO: 41         moltype = AA  length = 217
FEATURE               Location/Qualifiers
REGION                1..217
                      note = Synthetic: IgG1 Fc region sequence identical to SEQ
                       ID NO: 40 above except that it has additional M252Y, S254T
                       and T256E substitutions to enhance binding to FcRn
source                1..217
                      mol_type = protein
                      organism = synthetic construct
SEQUENCE: 41
APELLGGPSV FLFPPKPKDT LYITREPEVT CVVVDVSHED PEVKFNWYVD GVEVHNAKTK  60
PREEQYGSTY RVVSVLTVLH QDWLNGKEYK CKVSNKALPA PIEKTISKAK GQPREPQVYT  120
LPPSRDELTK NQVSLWCLVK GFYPSDIAVE WESNGQPENN YKTTPPVLDS DGSFFLYSKL  180
TVDKSRWQQG NVFSCSVMHE ALHNHYTQKS LSLSPGK                           217

SEQ ID NO: 42         moltype = AA  length = 15
FEATURE               Location/Qualifiers
REGION                1..15
                      note = Synthetic: IgG hinge sequence at the N-terminus of
                       FC1 or 2
source                1..15
                      mol_type = protein
                      organism = synthetic construct
SEQUENCE: 42
EPKSSDKTHT CPPCP                                                  15

SEQ ID NO: 43         moltype = AA  length = 10
FEATURE               Location/Qualifiers
REGION                1..10
                      note = Synthetic: IgG hinge sequence at the N-terminus of
                       FC1 or 2
```

```
source                  1..10
                        mol_type = protein
                        organism = synthetic construct
SEQUENCE: 43
DKTHTCPPCP                                                    10

SEQ ID NO: 44           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 44
GGGGS                                                         5

SEQ ID NO: 45           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 45
GGGSG                                                         5

SEQ ID NO: 46           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 46
GGSGG                                                         5

SEQ ID NO: 47           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 47
GSGGG                                                         5

SEQ ID NO: 48           moltype = AA  length = 6
FEATURE                 Location/Qualifiers
REGION                  1..6
                        note = Synthetic: Linker between N-terminus of second
                         binding domain and C-terminus of the first binding domain
source                  1..6
                        mol_type = protein
                        organism = synthetic construct
SEQUENCE: 48
GSGGGP                                                        6

SEQ ID NO: 49           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 49
GGEPS                                                         5

SEQ ID NO: 50           moltype = AA  length = 7
FEATURE                 Location/Qualifiers
REGION                  1..7
                        note = Synthetic: Linker between N-terminus of second
                         binding domain and C-terminus of the first binding domain
source                  1..7
                        mol_type = protein
```

```
                        organism = synthetic construct
SEQUENCE: 50
GGEGGGP                                                       7

SEQ ID NO: 51           moltype = AA  length = 12
FEATURE                 Location/Qualifiers
REGION                  1..12
                        note = Synthetic: Linker between N-terminus of second
                         binding domain and C-terminus of the first binding domain
source                  1..12
                        mol_type = protein
                        organism = synthetic construct
SEQUENCE: 51
GGEGGGSEGG GS                                                 12

SEQ ID NO: 52           moltype = AA  length = 8
FEATURE                 Location/Qualifiers
REGION                  1..8
                        note = Synthetic: Linker between N-terminus of second
                         binding domain and C-terminus of the first binding domain
source                  1..8
                        mol_type = protein
                        organism = synthetic construct
SEQUENCE: 52
GGGSGGGG                                                      8

SEQ ID NO: 53           moltype = AA  length = 24
FEATURE                 Location/Qualifiers
REGION                  1..24
                        note = Synthetic: Linker between N-terminus of second
                         binding domain and C-terminus of the first binding domain
source                  1..24
                        mol_type = protein
                        organism = synthetic construct
SEQUENCE: 53
GGGGSGGGGS GGGGSGGGGS GGGS                                    24

SEQ ID NO: 54           moltype = AA  length = 20
FEATURE                 Location/Qualifiers
REGION                  1..20
                        note = Synthetic: Linker between N-terminus of second
                         binding domain and C-terminus of the first binding domain
source                  1..20
                        mol_type = protein
                        organism = synthetic construct
SEQUENCE: 54
GGGGSGGGGS GGGGSGGGGS                                         20

SEQ ID NO: 55           moltype = AA  length = 5
FEATURE                 Location/Qualifiers
REGION                  1..5
                        note = Synthetic: Linker between N-terminus of second
                         binding domain and C-terminus of the first binding domain
source                  1..5
                        mol_type = protein
                        organism = synthetic construct
SEQUENCE: 55
EAAAK                                                         5

SEQ ID NO: 56           moltype = AA  length = 15
FEATURE                 Location/Qualifiers
REGION                  1..15
                        note = Synthetic: Linker between N-terminus of second
                         binding domain and C-terminus of the first binding domain
source                  1..15
                        mol_type = protein
                        organism = synthetic construct
SEQUENCE: 56
EAAAKEAAAK EAAAK                                              15

SEQ ID NO: 57           moltype = AA  length = 472
FEATURE                 Location/Qualifiers
REGION                  1..472
                        note = Synthetic: Fc Chain 1: E3.12.25-ab002.10-H5-Fc chain
                         (IgG1 truncated hinge N297G knob) (HLE)
source                  1..472
                        mol_type = protein
                        organism = synthetic construct
SEQUENCE: 57
```

```
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKEREF VAAIKWGPTY  180
YADSVKGRFT ISRDYSKNTV YLQMNSLRAE DTAVYYCAGK GSGTFSSNYR DFEYWGQGTL  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 58          moltype = AA  length = 227
FEATURE                Location/Qualifiers
REGION                 1..227
                       note = Synthetic: Fc Chain 2: Fc (IgG1 truncated hinge
                        N297G hole)
source                 1..227
                       mol_type = protein
                       organism = synthetic construct
SEQUENCE: 58
DKTHTCPPCP APELLGGPSV FLFPPKPKDT LMISRTPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 59          moltype = AA  length = 472
FEATURE                Location/Qualifiers
REGION                 1..472
                       note = Synthetic: Fc Chain 1: E3.12.25-ab002.10.18nR-H5-Fc
                        chain (IgG1 truncated hinge N297G knob) (HLE)
source                 1..472
                       mol_type = protein
                       organism = synthetic construct
SEQUENCE: 59
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKGLEF VSAIKWGPTY  180
YADSVKGRFT ISRDYSRNTV YLQMNSLRAE DTAVYYCAAK GSGTFSSNYR DFEYWGQGTL  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 60          moltype = AA  length = 472
FEATURE                Location/Qualifiers
REGION                 1..472
                       note = Synthetic: Fc Chain 1: E3.12.25-ab002.10.18nR-H5-Fc
                        chain (IgG1 truncated hinge N297G knob with YTE mutation)
                        (HLE)
source                 1..472
                       mol_type = protein
                       organism = synthetic construct
SEQUENCE: 60
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKGLEF VSAIKWGPTY  180
YADSVKGRFT ISRDYSRNTV YLQMNSLRAE DTAVYYCAAK GSGTFSSNYR DFEYWGQGTL  240
VTVSSDKTHT CPPCPAPELL GGPSVFLFPP KPKDTLYITR EPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 61          moltype = AA  length = 227
FEATURE                Location/Qualifiers
REGION                 1..227
                       note = Synthetic: Fc Chain 2: Fc (IgG1 truncated hinge
                        N297G hole with YTE mutations)
source                 1..227
                       mol_type = protein
                       organism = synthetic construct
SEQUENCE: 61
DKTHTCPPCP APELLGGPSV FLFPPKPKDT LYITREPEVT CVVVDVSHED PEVKFNWYVD  60
GVEVHNAKTK PREEQYGSTY RVVSVLTVLH QDWLNGKEYK CKVSNKALPA PIEKTISKAK  120
GQPREPQVYT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 62          moltype = AA  length = 472
FEATURE                Location/Qualifiers
REGION                 1..472
                       note = Synthetic: Fc Chain 1: E3.12.25- Ab002.10-H5-Fc
                        chain (IgG1 truncated hinge N297G knob with YTE mutation)
```

```
                          (HLE)
source                    1..472
                          mol_type = protein
                          organism = synthetic construct
SEQUENCE: 62
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKEREF VAAIKWGPTY  180
YADSVKGRFT ISRDYSKNTV YLQMNSLRAE DTAVYYCAGK GSGTFSSNYR DFEYWGQGTL  240
VTVSSDKTHT CPPCPAPELL GGPSVFLFPP KPKDTLYITR EPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 63             moltype = AA  length = 472
FEATURE                   Location/Qualifiers
REGION                    1..472
                          note = Synthetic: Fc Chain 1: E3.12.25-ab002.10.21nR-H5-Fc
                           chain (IgG1 truncated hinge N297G knob) (HLE)
source                    1..472
                          mol_type = protein
                          organism = synthetic construct
SEQUENCE: 63
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKGREF VSAIKWGPTY  180
YADSVKGRFT ISRDYSRNTL YLQMNSLRAE DTAVYYCAAK GSGTFSSNYR DFEYWGQGTL  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 64             moltype = AA  length = 472
FEATURE                   Location/Qualifiers
REGION                    1..472
                          note = Synthetic: Fc Chain 1: E3.12.25-ab002.10.21nR-H5-Fc
                           chain (IgG1 truncated hinge N297G knob with YTE mutation)
                           (HLE)
source                    1..472
                          mol_type = protein
                          organism = synthetic construct
SEQUENCE: 64
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAPSGRT FNPGDLMGWF RQAPGKGREF VSAIKWGPTY  180
YADSVKGRFT ISRDYSRNTL YLQMNSLRAE DTAVYYCAAK GSGTFSSNYR DFEYWGQGTL  240
VTVSSDKTHT CPPCPAPELL GGPSVFLFPP KPKDTLYITR EPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 65             moltype = AA  length = 126
FEATURE                   Location/Qualifiers
REGION                    1..126
                          note = Synthetic: Second binding domain, Ab092.6
source                    1..126
                          mol_type = protein
                          organism = synthetic construct
SEQUENCE: 65
EVQLLESGGG LVQPGGSLRL SCAASGHAFS DLHMGWFRQA PGKGLEFVSY INWSGRDSKY  60
ADSVKDRFTI SRDNSKNTLY LQMNSLRAED TAVYYCAAEK VYYSIVVSDG SQYDYWGQGT  120
LVTVSS                                                             126

SEQ ID NO: 66             moltype = AA  length = 126
FEATURE                   Location/Qualifiers
REGION                    1..126
                          note = Synthetic: Second binding domain, Ab092 Llama WT
source                    1..126
                          mol_type = protein
                          organism = synthetic construct
SEQUENCE: 66
EVQLVESGGG LVQTGGSLRL SCTASGHAFS DLHMGWFRQA PGKEREFVSY INWSGRDSKY  60
ADSVKDRFTI SRDNAKSTVY LQMNSLKPED TAVYYCAAEK VYYSIVVSDG SQYDYWGQGT  120
QVTVSS                                                             126

SEQ ID NO: 67             moltype = AA  length = 126
FEATURE                   Location/Qualifiers
REGION                    1..126
                          note = Synthetic: Second binding domain, Ab096.12
```

```
source                  1..126
                        mol_type = protein
                        organism = synthetic construct
SEQUENCE: 67
EVQLLESGGG LVQPGGSLRL SCAASGRTSA HIPMGWFRQA PGKEREFVSA VSWGGTYYAD  60
SVKGRFTISR VYAEDNSKNT VYLQMNSLRA EDTAVYYCAT RKYATFSTEN VDYDYWGQGT  120
LVTVSS                                                             126

SEQ ID NO: 68           moltype = AA  length = 126
FEATURE                 Location/Qualifiers
REGION                  1..126
                        note = Synthetic: Second binding domain, Ab096 Llama WT
source                  1..126
                        mol_type = protein
                        organism = synthetic construct
SEQUENCE: 68
EVQLVESGGG LVQAGGSLRL SCTASGRTSA HIPMGWFRQA PGKEREFVAA VSWGGTYYAD  60
SVKGRFTISR VYAEDNVENT VYLQMNSLKR EDTAVYYCAT RKYATFSTEN VDYDYWGQGT  120
QVTVSS                                                             126

SEQ ID NO: 69           moltype = AA  length = 473
FEATURE                 Location/Qualifiers
REGION                  1..473
                        note = Synthetic: Fc Chain 1: Ab007.11-H5 HLE
source                  1..473
                        mol_type = protein
                        organism = synthetic construct
SEQUENCE: 69
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAASGRA FRPHNVMAWF RQAPGKEREF VAAARWSGIY  180
YAESVKGRFT ISRDYSKNTV YLQMNSLRPE DTAVYYCAVS TAQDMTLALM SDYDYWGQGT  240
LVTVSSDKTH TCPPCPAPEL LGGPSVFLFP PKPKDTLMIS RTPEVTCVVV DVSHEDPEVK  300
FNWYVDGVEV HNAKTKPREE QYGSTYRVVS VLTVLHQDWL NGKEYKCKVS NKALPAPIEK  360
TISKAKGQPR EPQVYTLPPS RDELTKNQVS LWCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 70           moltype = AA  length = 472
FEATURE                 Location/Qualifiers
REGION                  1..472
                        note = Synthetic: Fc Chain 1: Ab052.9-H5 HLE
source                  1..472
                        mol_type = protein
                        organism = synthetic construct
SEQUENCE: 70
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAASGRT FSPSDLMGWF RQAPGKEREF VAAIKWGPTY  180
YSDSVKGRFT ISRDYSKNTV YLQMNSLRAE DTAVYYCAGK GSSTFSANYR DYEYWGQGTL  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 71           moltype = AA  length = 475
FEATURE                 Location/Qualifiers
REGION                  1..475
                        note = Synthetic: Fc Chain 1: Ab092.6-H5 HLE
source                  1..475
                        mol_type = protein
                        organism = synthetic construct
SEQUENCE: 71
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAASGHA FSDLHMGWFR QAPGKGLEFV SYINWSGRDS  180
KYADSVKDRF TISRDNSKNT LYLQMNSLRA EDTAVYYCAA EKVYYSIVVS DGSQYDYWGQ  240
GTLVTVSSDK THTCPPCPAP ELLGGPSVFL FPPKPKDTLM ISRTPEVTCV VVDVSHEDPE  300
VKFNWYVDGV EVHNAKTKPR EEQYGSTYRV VSVLTVLHQD WLNGKEYKCK VSNKALPAPI  360
EKTISKAKGQ PREPQVYTLP PSRDELTKNQ VSLWCLVKGF YPSDIAVEWE SNGQPENNYK  420
TTPPVLDSDG SFFLYSKLTV DKSRWQQGNV FSCSVMHEAL HNHYTQKSLS LSPGK       475

SEQ ID NO: 72           moltype = AA  length = 475
FEATURE                 Location/Qualifiers
REGION                  1..475
                        note = Synthetic: Fc Chain 1: Ab096.12-H5 HLE
source                  1..475
                        mol_type = protein
                        organism = synthetic construct
SEQUENCE: 72
```

-continued

```
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLLESG GGLVQPGGSL RLSCAASGRT SAHIPMGWFR QAPGKEREFV SAVSWGGTYY  180
ADSVKGRFTI SRVYAEDNSK NTVYLQMNSL RAEDTAVYYC ATRKYATFST ENVDYDYWGQ  240
GTLVTVSSDK THTCPPCPAP ELLGGPSVFL FPPKPKDTLM ISRTPEVTCV VVDVSHEDPE  300
VKFNWYVDGV EVHNAKTKPR EEQYGSTYRV VSVLTVLHQD WLNGKEYKCK VSNKALPAPI  360
EKTISKAKGQ PREPQVYTLP PSRDELTKNQ VSLWCLVKGF YPSDIAVEWE SNGQPENNYK  420
TTPPVLDSDG SFFLYSKLTV DKSRWQQGNV FSCSVMHEAL HNHYTQKSLS LSPGK       475

SEQ ID NO: 73          moltype = AA  length = 472
FEATURE                Location/Qualifiers
REGION                 1..472
                       note = Synthetic: Fc Chain 1: Ab002-H5 (HLE)
source                 1..472
                       mol_type = protein
                       organism = synthetic construct
SEQUENCE: 73
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLVESG GGLVQAGGSL RLSCAPSGRT FNPGDLMGWF RQAPGKEREF VAAIKWGPTY  180
YADSVKGRFT ISRDYVRNTV YVQMNDLKAE DTAVYYCAGK GSGTFSSNYR DFEYWGQGTQ  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 74          moltype = AA  length = 473
FEATURE                Location/Qualifiers
REGION                 1..473
                       note = Synthetic: Fc Chain 1: Ab007-H5 (HLE)
source                 1..473
                       mol_type = protein
                       organism = synthetic construct
SEQUENCE: 74
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLVESG GRLAQAGGSL RLSCAASGRA FRPHNVMAWF RQAPEKEREF VAAARWSGIY  180
YAESVKGRFS VSRDYDKNAV FLQMNGLKPE DTAVYYCAVS TAQDMTLALM SDYDYWGQGI  240
QVTVSSDKTH TCPPCPAPEL LGGPSVFLFP PKPKDTLMIS RTPEVTCVVV DVSHEDPEVK  300
FNWYVDGVEV HNAKTKPREE QYGSTYRVVS VLTVLHQDWL NGKEYKCKVS NKALPAPIEK  360
TISKAKGQPR EPQVYTLPPS RDELTKNQVS LWCLVKGFYP SDIAVEWESN GQPENNYKTT  420
PPVLDSDGSF FLYSKLTVDK SRWQQGNVFS CSVMHEALHN HYTQKSLSLS PGK         473

SEQ ID NO: 75          moltype = AA  length = 472
FEATURE                Location/Qualifiers
REGION                 1..472
                       note = Synthetic: Fc Chain 1: Ab052-H5 (HLE)
source                 1..472
                       mol_type = protein
                       organism = synthetic construct
SEQUENCE: 75
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLVESG GGLVQAGGSL RLSCAASGRT FSPSDLMGWF RQAPGKEREF VAAIKWGPTY  180
YSDSVKGRFT TSRDYVGNTV YLQMNDLKAE DTAVYHCAGK GSSTFSANYR DYEYWGQGTQ  240
VTVSSDKTHT CPPCPAPELL GGPSVFLFPP KPKDTLMISR TPEVTCVVVD VSHEDPEVKF  300
NWYVDGVEVH NAKTKPREEQ YGSTYRVVSV LTVLHQDWLN GKEYKCKVSN KALPAPIEKT  360
ISKAKGQPRE PQVYTLPPSR DELTKNQVSL WCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 76          moltype = AA  length = 475
FEATURE                Location/Qualifiers
REGION                 1..475
                       note = Synthetic: Fc Chain 1: Ab092-H5 (HLE)
source                 1..475
                       mol_type = protein
                       organism = synthetic construct
SEQUENCE: 76
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLVESG GGLVQTGGSL RLSCTASGHA FSDLHMGWFR QAPGKEREFV SYINWSGRDS  180
KYADSVKDRF TISRDNAKST VYLQMNSLKP EDTAVYYCAA EKVYYSIVVS DGSQYDYWGQ  240
GTQVTVSSDK THTCPPCPAP ELLGGPSVFL FPPKPKDTLM ISRTPEVTCV VVDVSHEDPE  300
VKFNWYVDGV EVHNAKTKPR EEQYGSTYRV VSVLTVLHQD WLNGKEYKCK VSNKALPAPI  360
EKTISKAKGQ PREPQVYTLP PSRDELTKNQ VSLWCLVKGF YPSDIAVEWE SNGQPENNYK  420
TTPPVLDSDG SFFLYSKLTV DKSRWQQGNV FSCSVMHEAL HNHYTQKSLS LSPGK       475

SEQ ID NO: 77          moltype = AA  length = 475
FEATURE                Location/Qualifiers
```

-continued

```
REGION                  1..475
                        note = Synthetic: Fc Chain 1: Ab096-H5 (HLE)
source                  1..475
                        mol_type = protein
                        organism = synthetic construct
SEQUENCE: 77
AVQLVESGGG LVQPGGSLRL SCAASGFTFS SYAMTWVRQA PGKGPEWVSA IASDGASTSY  60
ADSVKGRFTI SRDNSKNTLY LQMNSLRPED TAVYYCARGG YLTYDRYGQG TLVTVSSGGG  120
GSEVQLVESG GGLVQAGGSL RLSCTASGRT SAHIPMGWFR QAPGKEREFV AAVSWGGTYY  180
ADSVKGRFTI SRVYAEDNVE NTVYLQMNSL KREDTAVYYC ATRKYATFST ENVDYDYWGQ  240
GTQVTVSSDK THTCPPCPAP ELLGGPSVFL FPPKPKDTLM ISRTPEVTCV VVDVSHEDPE  300
VKFNWYVDGV EVHNAKTKPR EEQYGSTYRV VSVLTVLHQD WLNGKEYKCK VSNKALPAPI  360
EKTISKAKGQ PREPQVYTLP PSRDELTKNQ VSLWCLVKGF YPSDIAVEWE SNGQPENNYK  420
TTPPVLDSDG SFFLYSKLTV DKSRWQQGNV FSCSVMHEAL HNHYTQKSLS LSPGK       475

SEQ ID NO: 78           moltype = AA  length = 123
FEATURE                 Location/Qualifiers
REGION                  1..123
                        note = Synthetic: Second binding domain Ab002   IMGT
                         numbering scheme
source                  1..123
                        mol_type = protein
                        organism = synthetic construct
SEQUENCE: 78
EVQLVESGGG LVQAGGSLRL SCAPSGRTFN PGDLMGWFRQ APGKEREFVA AIKWGPTYYA  60
DSVKGRFTIS RDYVRNTVYV QMNDLKAEDT AVYYCAGKGS GTFSSNYRDF EYWGQGTQVT  120
VSS                                                               123

SEQ ID NO: 79           moltype = AA  length = 123
FEATURE                 Location/Qualifiers
REGION                  1..123
                        note = Synthetic: Second binding domain Ab002.10   IMGT
                         numbering scheme
source                  1..123
                        mol_type = protein
                        organism = synthetic construct
SEQUENCE: 79
EVQLLESGGG LVQPGGSLRL SCAPSGRTFN PGDLMGWFRQ APGKEREFVA AIKWGPTYYA  60
DSVKGRFTIS RDYSKNTVYL QMNSLRAEDT AVYYCAGKGS GTFSSNYRDF EYWGQGTLVT  120
VSS                                                               123

SEQ ID NO: 80           moltype = AA  length = 123
FEATURE                 Location/Qualifiers
REGION                  1..123
                        note = Synthetic: Second binding domain Ab002.5nR   IMGT
                         numbering scheme
source                  1..123
                        mol_type = protein
                        organism = synthetic construct
SEQUENCE: 80
EVQLLESGGG LVQPGGSLRL SCAPSGRTFN PGDLMGWFRQ APGKEREFVS AIKWGPTYYA  60
DSVKGRFTIS RDYSRNTLYL QMNSLRAEDT AVYYCAAKGS GTFSSNYRDF EYWGQGTLVT  120
VSS                                                               123

SEQ ID NO: 81           moltype = AA  length = 123
FEATURE                 Location/Qualifiers
REGION                  1..123
                        note = Synthetic: Second binding domain Ab002.5n   IMGT
                         numbering scheme
source                  1..123
                        mol_type = protein
                        organism = synthetic construct
SEQUENCE: 81
EVQLLESGGG LVQPGGSLRL SCAPSGRTFN PGDLMGWFRQ APGKEREFVS AIKWGPTYYA  60
DSVKGRFTIS RDYSKNTLYL QMNSLRAEDT AVYYCAAKGS GTFSSNYRDF EYWGQGTLVT  120
VSS                                                               123

SEQ ID NO: 82           moltype = AA  length = 123
FEATURE                 Location/Qualifiers
REGION                  1..123
                        note = Synthetic: Second binding domain Ab002.17nR   IMGT
                         numbering scheme
source                  1..123
                        mol_type = protein
                        organism = synthetic construct
SEQUENCE: 82
EVQLLESGGG LVQPGGSLRL SCAPSGRTFN PGDLMGWFRQ APGKGREFVS AIKWGPTYYA  60
DSVKGRFTIS RDYSRNTVYL QMNSLRAEDT AVYYCAAKGS GTFSSNYRDF EYWGQGTLVT  120
VSS                                                               123
```

```
SEQ ID NO: 83           moltype = AA  length = 123
FEATURE                 Location/Qualifiers
REGION                  1..123
                        note = Synthetic: Second binding domain Ab002.18nR   IMGT
                         numbering scheme
source                  1..123
                        mol_type = protein
                        organism = synthetic construct
SEQUENCE: 83
EVQLLESGGG LVQPGGSLRL SCAPSGRTFN PGDLMGWFRQ APGKGLEFVS AIKWGPTYYA  60
DSVKGRFTIS RDYSRNTVYL QMNSLRAEDT AVYYCAAKGS GTFSSNYRDF EYWGQGTLVT  120
VSS                                                               123

SEQ ID NO: 84           moltype = AA  length = 123
FEATURE                 Location/Qualifiers
REGION                  1..123
                        note = Synthetic: Second binding domain Ab002.21nR   IMGT
                         numbering scheme
source                  1..123
                        mol_type = protein
                        organism = synthetic construct
SEQUENCE: 84
EVQLLESGGG LVQPGGSLRL SCAPSGRTFN PGDLMGWFRQ APGKGREFVS AIKWGPTYYA  60
DSVKGRFTIS RDYSRNTLYL QMNSLRAEDT AVYYCAAKGS GTFSSNYRDF EYWGQGTLVT  120
VSS                                                               123

SEQ ID NO: 85           moltype = AA  length = 123
FEATURE                 Location/Qualifiers
REGION                  1..123
                        note = Synthetic: Second binding domain Ab002.21n   IMGT
                         numbering scheme
source                  1..123
                        mol_type = protein
                        organism = synthetic construct
SEQUENCE: 85
EVQLLESGGG LVQPGGSLRL SCAPSGRTFN PGDLMGWFRQ APGKGREFVS AIKWGPTYYA  60
DSVKGRFTIS RDYSKNTLYL QMNSLRAEDT AVYYCAAKGS GTFSSNYRDF EYWGQGTLVT  120
VSS                                                               123

SEQ ID NO: 86           moltype = AA  length = 124
FEATURE                 Location/Qualifiers
REGION                  1..124
                        note = Synthetic: Second binding domain Ab007   IMGT
                         numbering scheme
source                  1..124
                        mol_type = protein
                        organism = synthetic construct
SEQUENCE: 86
EVQLVESGGR LAQAGGSLRL SCAASGRAFR PHNVMAWFRQ APEKEREFVA AARWSGIYYA  60
ESVKGRFSVS RDYDKNAVFL QMNGLKPEDT AVYYCAVSTA QDMTLALMSD YDYWGQGIQV  120
TVSS                                                              124

SEQ ID NO: 87           moltype = AA  length = 124
FEATURE                 Location/Qualifiers
REGION                  1..124
                        note = Synthetic: Second binding domain Ab007.11   IMGT
                         numbering scheme
source                  1..124
                        mol_type = protein
                        organism = synthetic construct
SEQUENCE: 87
EVQLLESGGG LVQPGGSLRL SCAASGRAFR PHNVMAWFRQ APGKEREFVA AARWSGIYYA  60
ESVKGRFTIS RDYSKNTVYL QMNSLRPEDT AVYYCAVSTA QDMTLALMSD YDYWGQGTLV  120
TVSS                                                              124

SEQ ID NO: 88           moltype = AA  length = 123
FEATURE                 Location/Qualifiers
REGION                  1..123
                        note = Synthetic: Second binding domain Ab052   IMGT
                         numbering scheme
source                  1..123
                        mol_type = protein
                        organism = synthetic construct
SEQUENCE: 88
EVQLVESGGG LVQAGGSLRL SCAASGRTFS PSDLMGWFRQ APGKEREFVA AIKWGPTYYS  60
DSVKGRFTTS RDYVGNTVYL QMNDLKAEDT AVYHCAGKGS STFSANYRDY EYWGQGTQVT  120
VSS                                                               123
```

-continued

```
SEQ ID NO: 89          moltype = AA  length = 123
FEATURE                Location/Qualifiers
REGION                 1..123
                       note = Synthetic: Second binding domain Ab052.9   IMGT
                        numbering scheme
source                 1..123
                       mol_type = protein
                       organism = synthetic construct
SEQUENCE: 89
EVQLLESGGG LVQPGGSLRL SCAASGRTFS PSDLMGWFRQ APGKEREFVA AIKWGPTYYS  60
DSVKGRFTIS RDYSKNTVYL QMNSLRAEDT AVYYCAGKGS STFSANYRDY EYWGQGTLVT  120
VSS                                                                123

SEQ ID NO: 90          moltype = AA  length = 126
FEATURE                Location/Qualifiers
REGION                 1..126
                       note = Synthetic: Second binding domain Ab0092   IMGT
                        numbering scheme
source                 1..126
                       mol_type = protein
                       organism = synthetic construct
SEQUENCE: 90
EVQLVESGGG LVQTGGSLRL SCTASGHAFS DLHMGWFRQA PGKEREFVSY INWSGRDSKY  60
ADSVKDRFTI SRDNAKSTVY LQMNSLKPED TAVYYCAAEK VYYSIVVSDG SQYDYWGQGT  120
QVTVSS                                                             126

SEQ ID NO: 91          moltype = AA  length = 126
FEATURE                Location/Qualifiers
REGION                 1..126
                       note = Synthetic: Second binding domain Ab0092.6   IMGT
                        numbering scheme
source                 1..126
                       mol_type = protein
                       organism = synthetic construct
SEQUENCE: 91
EVQLLESGGG LVQPGGSLRL SCAASGHAFS DLHMGWFRQA PGKGLEFVSY INWSGRDSKY  60
ADSVKDRFTI SRDNSKNTLY LQMNSLRAED TAVYYCAAEK VYYSIVVSDG SQYDYWGQGT  120
LVTVSS                                                             126

SEQ ID NO: 92          moltype = AA  length = 126
FEATURE                Location/Qualifiers
REGION                 1..126
                       note = Synthetic: Second binding domain Ab0096   IMGT
                        numbering scheme
source                 1..126
                       mol_type = protein
                       organism = synthetic construct
SEQUENCE: 92
EVQLVESGGG LVQAGGSLRL SCTASGRTSA HIPMGWFRQA PGKEREFVAA VSWGGTYYAD  60
SVKGRFTISR VYAEDNVENT VYLQMNSLKR EDTAVYYCAT RKYATFSTEN VDYDYWGQGT  120
QVTVSS                                                             126

SEQ ID NO: 93          moltype = AA  length = 126
FEATURE                Location/Qualifiers
REGION                 1..126
                       note = Synthetic: Second binding domain Ab0096.12   IMGT
                        numbering scheme
source                 1..126
                       mol_type = protein
                       organism = synthetic construct
SEQUENCE: 93
EVQLLESGGG LVQPGGSLRL SCAASGRTSA HIPMGWFRQA PGKEREFVSA VSWGGTYYAD  60
SVKGRFTISR VYAEDNSKNT VYLQMNSLRA EDTAVYYCAT RKYATFSTEN VDYDYWGQGT  120
LVTVSS                                                             126

SEQ ID NO: 94          moltype = AA  length = 9
FEATURE                Location/Qualifiers
REGION                 1..9
                       note = Synthetic: scFv light chain CDR1 Ab106   IMGT
                        numbering scheme
source                 1..9
                       mol_type = protein
                       organism = synthetic construct
SEQUENCE: 94
SSDVGSYNL                                                          9

SEQ ID NO: 95          moltype = AA  length = 9
FEATURE                Location/Qualifiers
REGION                 1..9
```

```
                        note = Synthetic: scFv light chain CDR1 Ab108  IMGT
                         numbering scheme
source                  1..9
                        mol_type = protein
                        organism = synthetic construct
SEQUENCE: 95
SSDVGGYNF                                                                9

SEQ ID NO: 96           moltype = AA  length = 8
FEATURE                 Location/Qualifiers
REGION                  1..8
                        note = Synthetic: scFv light chain CDR1 Ab114  IMGT
                         numbering scheme
source                  1..8
                        mol_type = protein
                        organism = synthetic construct
SEQUENCE: 96
SSNIGNNY                                                                 8

SEQ ID NO: 97           moltype = AA  length = 9
FEATURE                 Location/Qualifiers
REGION                  1..9
                        note = Synthetic: scFv light chain CDR1 Ab116  IMGT
                         numbering scheme
source                  1..9
                        mol_type = protein
                        organism = synthetic construct
SEQUENCE: 97
SSNIGAGYA                                                                9

SEQ ID NO: 98           moltype =   length =
SEQUENCE: 98
000

SEQ ID NO: 99           moltype =   length =
SEQUENCE: 99
000

SEQ ID NO: 100          moltype =   length =
SEQUENCE: 100
000

SEQ ID NO: 101          moltype =   length =
SEQUENCE: 101
000

SEQ ID NO: 102          moltype = AA  length = 10
FEATURE                 Location/Qualifiers
REGION                  1..10
                        note = Synthetic: scFv light chain CDR3 Ab106   IMGT
                         numbering scheme
source                  1..10
                        mol_type = protein
                        organism = synthetic construct
SEQUENCE: 102
SSYRNHYTGV                                                               10

SEQ ID NO: 103          moltype = AA  length = 13
FEATURE                 Location/Qualifiers
REGION                  1..13
                        note = Synthetic: scFv light chain CDR3 Ab108  IMGT
                         numbering scheme
source                  1..13
                        mol_type = protein
                        organism = synthetic construct
SEQUENCE: 103
CGTWDGSLSV VVF                                                           13

SEQ ID NO: 104          moltype = AA  length = 13
FEATURE                 Location/Qualifiers
REGION                  1..13
                        note = Synthetic: scFv light chain CDR3 Ab114  IMGT
                         numbering scheme
source                  1..13
                        mol_type = protein
                        organism = synthetic construct
SEQUENCE: 104
GTWDSSLSAG WVF                                                           13
```

-continued

```
SEQ ID NO: 105          moltype = AA  length = 12
FEATURE                 Location/Qualifiers
REGION                  1..12
                        note = Synthetic: scFv light chain CDR3 Ab116  IMGT
                         numbering scheme
source                  1..12
                        mol_type = protein
                        organism = synthetic construct
SEQUENCE: 105
QSYDSSLSEY VF                                                12

SEQ ID NO: 106          moltype = AA  length = 7
FEATURE                 Location/Qualifiers
REGION                  1..7
                        note = Synthetic: scFv heavy chain CDR1 Ab106   IMGT
                         numbering scheme
source                  1..7
                        mol_type = protein
                        organism = synthetic construct
SEQUENCE: 106
YTFTSYG                                                      7

SEQ ID NO: 107          moltype = AA  length = 8
FEATURE                 Location/Qualifiers
REGION                  1..8
                        note = Synthetic: scFv heavy chain CDR1 Ab108  IMGT
                         numbering scheme  IMGT numbering scheme
source                  1..8
                        mol_type = protein
                        organism = synthetic construct
SEQUENCE: 107
GYTFTSYG                                                     8

SEQ ID NO: 108          moltype = AA  length = 8
FEATURE                 Location/Qualifiers
REGION                  1..8
                        note = Synthetic: scFv heavy chain CDR1 Ab114  IMGT
                         numbering scheme
source                  1..8
                        mol_type = protein
                        organism = synthetic construct
SEQUENCE: 108
GYTFTSYG                                                     8

SEQ ID NO: 109          moltype = AA  length = 8
FEATURE                 Location/Qualifiers
REGION                  1..8
                        note = Synthetic: scFv heavy chain CDR1 Ab116  IMGT
                         numbering scheme
source                  1..8
                        mol_type = protein
                        organism = synthetic construct
SEQUENCE: 109
GYTFTSYY                                                     8

SEQ ID NO: 110          moltype = AA  length = 8
FEATURE                 Location/Qualifiers
REGION                  1..8
                        note = Synthetic: scFv heavy chain CDR2 Ab106   IMGT
                         numbering scheme
source                  1..8
                        mol_type = protein
                        organism = synthetic construct
SEQUENCE: 110
IYPSRGDT                                                     8

SEQ ID NO: 111          moltype = AA  length = 8
FEATURE                 Location/Qualifiers
REGION                  1..8
                        note = Synthetic: scFv heavy chain CDR2 Ab108  IMGT
                         numbering scheme
source                  1..8
                        mol_type = protein
                        organism = synthetic construct
SEQUENCE: 111
ISAYNGNT                                                     8

SEQ ID NO: 112          moltype = AA  length = 8
FEATURE                 Location/Qualifiers
```

-continued

```
REGION               1..8
                     note = Synthetic: scFv heavy chain CDR2 Ab114  IMGT
                      numbering scheme
source               1..8
                     mol_type = protein
                     organism = synthetic construct
SEQUENCE: 112
ISAYNGNT                                                                 8

SEQ ID NO: 113       moltype = AA  length = 8
FEATURE              Location/Qualifiers
REGION               1..8
                     note = Synthetic: scFv heavy chain CDR2 Ab116  IMGT
                      numbering scheme
source               1..8
                     mol_type = protein
                     organism = synthetic construct
SEQUENCE: 113
ISAYNGNT                                                                 8

SEQ ID NO: 114       moltype = AA  length = 12
FEATURE              Location/Qualifiers
REGION               1..12
                     note = Synthetic: scFv heavy chain CDR3 Ab106   IMGT
                      numbering scheme
source               1..12
                     mol_type = protein
                     organism = synthetic construct
SEQUENCE: 114
AKGGDYGDYL DT                                                            12

SEQ ID NO: 115       moltype = AA  length = 13
FEATURE              Location/Qualifiers
REGION               1..13
                     note = Synthetic: scFv heavy chain CDR3 Ab108  IMGT
                      numbering scheme
source               1..13
                     mol_type = protein
                     organism = synthetic construct
SEQUENCE: 115
ARAMGYSYGL GYW                                                           13

SEQ ID NO: 116       moltype = AA  length = 13
FEATURE              Location/Qualifiers
REGION               1..13
                     note = Synthetic: scFv heavy chain CDR3 Ab114  IMGT
                      numbering scheme
source               1..13
                     mol_type = protein
                     organism = synthetic construct
SEQUENCE: 116
ARAMGYSYGL GYW                                                           13

SEQ ID NO: 117       moltype = AA  length = 16
FEATURE              Location/Qualifiers
REGION               1..16
                     note = Synthetic: scFv heavy chain CDR3 Ab116  IMGT
                      numbering scheme
source               1..16
                     mol_type = protein
                     organism = synthetic construct
SEQUENCE: 117
ARDYSSSSSG FGTDYW                                                        16

SEQ ID NO: 118       moltype = AA  length = 246
FEATURE              Location/Qualifiers
REGION               1..246
                     note = Synthetic: Ab106 scFv   IMGT numbering scheme
source               1..246
                     mol_type = protein
                     organism = synthetic construct
SEQUENCE: 118
QSALTQPASV SGSPGQSITI SCTGTSSDVG SYNLVSWYQQ VPDKAPKLII YEVTERPSGI  60
SNRFSGSKSG NTASLTISGL QAEDEGDYYC SSYRNHYTGV FGTGTKVTVL SGGGGGSGGG  120
GSGGGRSEVQ LVQSGAEVKK PGASVKVSCK ASGYTFTSYG ISWVRQAPGQ GLEWMGGIYP  180
SRGDTNYAQK FQGRVTMTRD TSISTAYMEL SRLTSDDTAV YYCAKGGDYG DYLDTWGQGT  240
LVTVSS                                                                   246

SEQ ID NO: 119       moltype = AA  length = 247
```

-continued

```
FEATURE                Location/Qualifiers
REGION                 1..247
                       note = Synthetic: Ab108 scFv  IMGT numbering scheme
source                 1..247
                       mol_type = protein
                       organism = synthetic construct
SEQUENCE: 119
QSVLTQPASA SGSPGQSITI SCTGTSSDVG GYNFVSWYQQ LPGTAPKLLI YDNDKRPSGI  60
SDRFSGSKSG TSATLGITGL QTGDEADYYC GTWDGSLSVV VFGGGTKVTV LSGGGGGSGG  120
GGSGGGRSEV QLVQSGAEVK KPGASVKVSC KASGYTFTSY GISWVRQAPG QGLEWMGWIS  180
AYNGNTNYAQ KLQGRVTMTR DTSTSTAYME LRSLRSEDTA VYYCARAMGY SYGLGYWGQG  240
TMVTVSS                                                           247

SEQ ID NO: 120         moltype = AA  length = 247
FEATURE                Location/Qualifiers
REGION                 1..247
                       note = Synthetic: Ab114 scFv  IMGT numbering scheme
source                 1..247
                       mol_type = protein
                       organism = synthetic construct
SEQUENCE: 120
QSVLTQPPSV SVAPGQKVTI SCSGSSSNIG NNYVSWYQQL PGTAPKLLIY DNNKRPSGIP  60
DRFSGSKSGT SATLGITGLQ TGDEADYYCG TWDSSLSAGW VFGGGTQLII LSGGGGGSGG  120
GGSGGGRSEV QLVQSGAEVK KPGVSVKVSC KASGYTFTSY GISWVRQAPG QGLEWMGWIS  180
AYNGNTNYAQ KLQGRVTMTT DTSTSTAYME LSRLRSDDTA VYYCARAMGY SYGLGYWGQG  240
TLVTVSS                                                           247

SEQ ID NO: 121         moltype = AA  length = 250
FEATURE                Location/Qualifiers
REGION                 1..250
                       note = Synthetic: Ab116 scFv  IMGT numbering scheme
source                 1..250
                       mol_type = protein
                       organism = synthetic construct
SEQUENCE: 121
QSVLTQPPSV SGAPGQRVTI SCTGSSSNIG AGYAVHWYQQ LPGVAPKLLI YGNSNRPSGV  60
PDRFSGSKSG TSASLGITGL LAEDEADYYC QSYDSSLSEY VFGTGTKVTV LSGGGGGSGG  120
GGSGGGRSQV QLVQSGAEVK KPGASVKVSC KASGYTFTSY YMHWVRQAPG QGLEWMGWIS  180
AYNGNTNYAQ KLQGRVTMTT DTSTSTAYME LRSLRSDDTA VYYCARDYSS SSSGFGTDYW  240
GQGTLVTVSS                                                        250

SEQ ID NO: 122         moltype = AA  length = 117
FEATURE                Location/Qualifiers
REGION                 1..117
                       note = Synthetic: Ab062
source                 1..117
                       mol_type = protein
                       organism = synthetic construct
SEQUENCE: 122
EVQLVESGGD LVQAGGSLRL SCAASGSISS TNTMGWYRQV PGKQREPVAS ITSGGTTNYD  60
DSVKGRFTIS TDNAKKEVYL QMNSLSPEDT AVYYCYLRSS LSWRTYWGQG TQVTVSS     117

SEQ ID NO: 123         moltype = AA  length = 8
FEATURE                Location/Qualifiers
REGION                 1..8
                       note = Synthetic: Ab062 CDR1
source                 1..8
                       mol_type = protein
                       organism = synthetic construct
SEQUENCE: 123
GSISSTNT                                                          8

SEQ ID NO: 124         moltype = AA  length = 7
FEATURE                Location/Qualifiers
REGION                 1..7
                       note = Synthetic: Ab062 CDR2
source                 1..7
                       mol_type = protein
                       organism = synthetic construct
SEQUENCE: 124
ITSGGTT                                                           7

SEQ ID NO: 125         moltype = AA  length = 11
FEATURE                Location/Qualifiers
REGION                 1..11
                       note = Synthetic: Ab062 CDR3
source                 1..11
                       mol_type = protein
                       organism = synthetic construct
```

-continued

```
SEQUENCE: 125
YLRSSLSWRT Y                                                     11

SEQ ID NO: 126          moltype = AA  length = 123
FEATURE                 Location/Qualifiers
REGION                  1..123
                        note = Synthetic: Ab073
source                  1..123
                        mol_type = protein
                        organism = synthetic construct
SEQUENCE: 126
EVQLVESGGG LVQPGGSLRL SCVASGFTFG TYAMSWVRQA PGKGSEWVSH ITSSGGFTYY  60
ADSVKGRFTI SRDNAKNTLY LQMNSLKPED TAVYYCARGH WAFYNITTPE EVRGQGTQVT  120
VSS                                                              123

SEQ ID NO: 127          moltype = AA  length = 8
FEATURE                 Location/Qualifiers
REGION                  1..8
                        note = Synthetic: Ab073 CDR1
source                  1..8
                        mol_type = protein
                        organism = synthetic construct
SEQUENCE: 127
GFTFGTYA                                                         8

SEQ ID NO: 128          moltype = AA  length = 8
FEATURE                 Location/Qualifiers
REGION                  1..8
                        note = Synthetic: Ab073 CDR2
source                  1..8
                        mol_type = protein
                        organism = synthetic construct
SEQUENCE: 128
ITSSGGFT                                                         8

SEQ ID NO: 129          moltype = AA  length = 17
FEATURE                 Location/Qualifiers
REGION                  1..17
                        note = Synthetic: Ab073 CDR3
source                  1..17
                        mol_type = protein
                        organism = synthetic construct
SEQUENCE: 129
ARGHWAFYNI TTPEEVR                                               17

SEQ ID NO: 130          moltype = AA  length = 117
FEATURE                 Location/Qualifiers
REGION                  1..117
                        note = Synthetic: Ab077
source                  1..117
                        mol_type = protein
                        organism = synthetic construct
SEQUENCE: 130
EVQLVESGGD LVQAGGSLRL SCAASGSISS TITMGWYRQA PGKQREPLAS ITSGGTTNYD  60
DSVKGRFTIS RDNAKKEVYL QMNSLAPEDT AVYYCYLRSS LSWRTYWGQG TQVTVSS     117

SEQ ID NO: 131          moltype = AA  length = 8
FEATURE                 Location/Qualifiers
REGION                  1..8
                        note = Synthetic: Ab077 CDR1
source                  1..8
                        mol_type = protein
                        organism = synthetic construct
SEQUENCE: 131
GSISSTIT                                                         8

SEQ ID NO: 132          moltype = AA  length = 7
FEATURE                 Location/Qualifiers
REGION                  1..7
                        note = Synthetic: Ab077 CDR2
source                  1..7
                        mol_type = protein
                        organism = synthetic construct
SEQUENCE: 132
ITSGGTT                                                          7

SEQ ID NO: 133          moltype = AA  length = 11
FEATURE                 Location/Qualifiers
REGION                  1..11
```

-continued

```
                        note = Synthetic: Ab077 CDR3
source                  1..11
                        mol_type = protein
                        organism = synthetic construct
SEQUENCE: 133
YLRSSLSWRT Y                                              11
```

What is claimed is:

1. A multi-domain molecule comprising:

(i) a first binding domain that binds to PD-1, wherein the first binding domain comprises a CDR1, a CDR2, and a CDR3 comprising the following sequences:

```
                                    (SEQ ID NO: 1)
CDR1 - GFTFSSYA,
                                    (SEQ ID NO: 2)
CDR2 - IASDGAST, and
                                    (SEQ ID NO: 3)
CDR3 - CARGGYLTYDRY,
```

and (ii) a second binding domain that binds to CD1a, wherein the second binding domain comprises a CDR1, a CDR2, and a CDR3 comprising the following sequences:

CDR1—GRTFNPGDLMG (SEQ ID NO: 4),

CDR2—AIKWGPTYYADSVKG (SEQ ID NO: 7), and

CDR3—GSGTFSSNYRDFEY (SEQ ID NO: 10), wherein the C-terminus of the first binding domain is linked to the N-terminus of the second binding domain.

2. The multi-domain molecule of claim 1, wherein the first binding domain binds to an epitope in PD-1 comprising one or more or all of the following amino acids: E38, F59, P60, E61, T75, Q76, L77, P78, N79 and G80, numbered according to SEQ ID NO: 13.

3. The multi-domain molecule of claim 1, wherein the first binding domain comprises FR1-CDR1-FR2-CDR2-FR3-CDR3-FR4, wherein FR is a framework region, and wherein FR1, FR2, FR3 and FR4 comprise the following sequences:

FR1—AVQLVESGGGLVQPGGSLRLSCAAS (SEQ ID NO: 14), with zero, one, two or three mutations therein, FR2—MTWVRQAPGKGPEWVSA (SEQ ID NO: 15), with zero, one, two or three mutations therein, FR3—SYADSVKGRFTISRDNSKNTLYLQMNSLRPEDTAVYY (SEQ ID NO: 16), with zero, one, two or three mutations therein, and FR4—YLTYDRYGQGTLVTVSS (SEQ ID NO: 17), with zero, one, two or three mutations therein.

4. The multi-domain molecule of claim 1, wherein the first binding domain comprises:

(a) the amino acid sequence provided in SEQ ID NO: 18 or a humanized version thereof, or an amino acid sequence having at least 90% sequence identity to SEQ ID NO: 18; or (b) the amino acid sequence of SEQ ID NO: 20, or an amino acid sequence having at least 90% sequence identity to SEQ ID NO: 20.

5. The multi-domain molecule of claim 1, wherein the second binding domain is a humanized llama anti-CD1a VHH.

6. The multi-domain molecule of claim 5, wherein the humanized llama anti-CD1a VHH comprises one or more or all of the following amino acids:

(a) P24, F38, E45, R46, F48, A50, Y73, R75, V78, and G97, numbered according to SEQ ID NO: 21;

(b) P24, F38, F48, Y73, R75, and V78, numbered according to SEQ ID NO: 25;

(c) F38, E45, R46, F48, A50, Y73, K75, V78, P87 and V97, numbered according to SEQ ID NO: 28; or (d) F38, E45, R46, F48, A50, Y73, K75, V78, and G97, numbered according to SEQ ID NO: 29.

7. The multi-domain molecule of claim 1, wherein the second binding domain comprises FR1-CDR1-FR2-CDR2-FR3-CDR3-FR4, wherein FR is a framework region, and wherein FR1, FR2, FR3 and FR4 comprise the following sequences:

FR1—EVQLLESGGGLVQPGGSLRLSCAAS (SEQ ID NO: 30), with zero, one, two or three mutations therein, FR2—WVRQAPGKGLEWVS (SEQ ID NO: 31), with zero, one, two or three mutations therein, FR3—RFTISRDNSKNTLYLQMNSLRAEDTAVYYCAAK (SEQ ID NO: 32), with zero, one, two or three mutations therein, and FR4—WGQGTLVTVSS (SEQ ID NO: 33), with zero, one, two or three mutations therein.

8. The multi-domain molecule of claim 7, wherein the mutation(s) in the second binding domain framework regions are selected from:

(a) A24P, V38F, G45E, L46R, W48F, S50A, N73Y, K75R, L78V and A97G numbered according to SEQ ID NO: 21; or (b) A24P, V38F, W48F, N73Y, K75R, and L78V numbered according to SEQ ID NO: 25.

9. The multi-domain molecule of claim 1, wherein the second binding domain comprises the amino acid sequence provided in SEQ ID NO: 34 or a humanized version thereof.

10. The multi-domain molecule of claim 1, further comprising (iii) a half-life extending domain, wherein the half-life extending domain comprises a first IgG Fc chain (FC1) and a second IgG Fc chain (FC2), wherein the FC1 chain and FC2 chain dimerise to form an Fc domain, and wherein the C-terminus of the second binding domain is linked to the N-terminus of FC1.

11. The multi-domain molecule of claim 10, wherein the half-life extending domain comprises:

(a) one or more amino acid substitutions which facilitate dimerisation of FC1 and FC2;

(b) one or more amino acid substitutions which prevent or reduce binding to FcγR;

(c) one or more amino acid substitutions which promote binding to FcRn;

(d) one or more amino acid substitutions which attenuate an effector function of the Fc domain.

12. The multi-domain molecule of claim 1, wherein, the first binding domain is linked to the N-terminus of the second binding domain by a linker and/or IgG hinge sequence.

13. The multi-domain molecule of claim 1, wherein the multi-domain molecule comprises the amino acid sequence of:

(a) (i) SEQ ID NO: 57; and (ii) SEQ ID NO: 58;

(b) (i) SEQ ID NO: 59; and (ii) SEQ ID NO: 58; or (c) (i) SEQ ID NO: 63; and (ii) SEQ ID NO: 58.

14. A nucleic acid encoding the multi-domain molecule of claim 1, wherein the first and second binding domains are encoded within a single open reading frame, or within two distinct open reading frames.

15. An expression vector comprising the nucleic acid of claim 14.

16. A cell comprising the expression vector of claim 15.

17. A purified and/or engineered cell presenting the multi-domain molecule of claim 1.

18. A pharmaceutical composition comprising the multi-domain molecule of claim 1, together with one or more pharmaceutically acceptable carriers or excipients.

19. A method of producing a multi-domain molecule, the method comprising a) maintaining a cell comprising the nucleic acid of claim 14 under optimal conditions for expression of the multi-domain molecule and b) isolating the multi-domain molecule.

20. The multi-domain molecule of claim 1, wherein the second binding domain comprises an amino acid sequence having at least 90% sequence identity to SEQ ID NO: 21.

21. The multi-domain molecule of claim 1, wherein the second binding domain comprises an amino acid sequence having at least 90% sequence identity to SEQ ID NO: 22.

22. The multi-domain molecule of claim 1, wherein the second binding domain comprises an amino acid sequence having at least 90% sequence identity to SEQ ID NO: 23.

23. The multi-domain molecule of claim 1, wherein the second binding domain comprises an amino acid sequence having at least 90% sequence identity to SEQ ID NO: 24.

24. The multi-domain molecule of claim 1, wherein the second binding domain comprises an amino acid sequence having at least 90% sequence identity to SEQ ID NO: 25.

25. The multi-domain molecule of claim 1, wherein the second binding domain comprises an amino acid sequence having at least 90% sequence identity to SEQ ID NO: 26.

26. The multi-domain molecule of claim 1, wherein the second binding domain comprises an amino acid sequence having at least 90% sequence identity to SEQ ID NO: 27.

27. A method for treating an autoimmune disease in a subject, the method comprising administering the multi-domain molecule of claim 1.

28. A multi-domain molecule comprising: (i) a first binding domain that binds to PD-1, wherein the first binding domain comprises a CDR1, a CDR2, and a CDR3 comprising the following sequences:

```
                                (SEQ ID NO: 1)
CDR1 - GFTFSSYA,

                                (SEQ ID NO: 2)
CDR2 - IASDGAST, and

                                (SEQ ID NO: 3)
CDR3 - CARGGYLTYDRY,
```

and (ii) a second binding domain that binds to CD1a, wherein the second binding domain comprises a CDR1, a CDR2, and a CDR3 comprising the following sequences:

```
                                (SEQ ID NO: 5)
CDR1 - GRAFRPHNVMA,

                                (SEQ ID NO: 8)
CDR2 - AARWSGIYYAESVKG ,
and

                               (SEQ ID NO: 11)
CDR3 - STAQDMTLALMSDYDY,
```

wherein the C-terminus of the first binding domain is linked to the N-terminus of the second binding domain.

29. The multi-domain molecule of claim 28, wherein the second binding domain comprises an amino acid sequence having at least 90% sequence identity to SEQ ID NO: 28.

30. A method for treating an autoimmune disease in a subject, the method comprising administering the multi-domain molecule of claim 28.

31. A nucleic acid encoding the multi-domain molecule of claim 28, wherein the first and second binding domains are encoded within a single open reading frame, or within two distinct open reading frames.

32. An expression vector comprising the nucleic acid of claim 31.

33. A cell comprising the expression vector of claim 32.

34. A purified and/or engineered cell presenting the multi-domain molecule of claim 28.

35. A pharmaceutical composition comprising the multi-domain molecule of claim 28, together with one or more pharmaceutically acceptable carriers or excipients.

36. A method of producing a multi-domain molecule, the method comprising a) maintaining a cell comprising the nucleic acid of claim 31 under optimal conditions for expression of the multi-domain molecule and b) isolating the multi-domain molecule.

37. A multi-domain molecule comprising:

(i) a first binding domain that binds to PD-1, wherein the first binding domain comprises a CDR1, a CDR2, and a CDR3 comprising the following sequences:

```
                                (SEQ ID NO: 1)
CDR1 - GFTFSSYA,

                                (SEQ ID NO: 2)
CDR2 - IASDGAST, and

                                (SEQ ID NO: 3)
CDR3 - CARGGYLTYDRY,
```

and (ii) a second binding domain that binds to CD1a, wherein the second binding domain comprises a CDR1, a CDR2, and a CDR3 comprising the following sequences:

```
                                (SEQ ID NO: 6)
CDR1 - GRTFSPSDLMG,

                                (SEQ ID NO: 9)
CDR2 - AIKWGPTYYSDSVKG, and

                               (SEQ ID NO: 12)
CDR3 - GSSTFSANYRDYEY,
```

wherein the C-terminus of the first binding domain is linked to the N-terminus of the second binding domain.

38. The multi-domain molecule of claim 37, wherein the second binding domain comprises an amino acid sequence having at least 90% sequence identity to SEQ ID NO: 27.

39. A method for treating an autoimmune disease in a subject, the method comprising administering the multi-domain molecule of claim 37.

40. A nucleic acid encoding the multi-domain molecule of claim 37, wherein the first and second binding domains are encoded within a single open reading frame, or within two distinct open reading frames.

41. An expression vector comprising the nucleic acid of claim 40.

42. A cell comprising the expression vector of claim 41.

43. A purified and/or engineered cell presenting the multi-domain molecule of claim 37.

44. A pharmaceutical composition comprising the multi-domain molecule of claim 37, together with one or more pharmaceutically acceptable carriers or excipients.

45. A method of producing a multi-domain molecule, the method comprising a) maintaining a cell comprising the nucleic acid of claim 40 under optimal conditions for expression of the multi-domain molecule and b) isolating the multi-domain molecule.

46. A single domain antibody that binds to CD1a, comprising a CDR1, CDR2, and CDR3, comprising the following amino acid sequences:

(a) CDR1 - GRTFNPGDLMG, (SEQ ID NO: 4)

CDR2 - AIKWGPTYYADSVKG, (SEQ ID NO: 7)
and

-continued

CDR3 - GSGTFSSNYRDFEY; (SEQ ID NO: 10)

(b) CDR1 - GRAFRPHNVMA, (SEQ ID NO: 5)

CDR2 - AARWSGIYYAESVKG, (SEQ ID NO: 8)
and

CDR3 - STAQDMTLALMSDYDY; (SEQ ID NO: 11)
or (c) CDR1 - GRTFSPSDLMG, (SEQ ID NO: 6)

CDR2 - AIKWGPTYYSDSVKG, (SEQ ID NO: 9)
and

CDR3 - GSSTFSANYRDYEY. (SEQ ID NO: 12)

* * * * *